US011918702B2

(12) United States Patent
Snoeck et al.

(10) Patent No.: US 11,918,702 B2
(45) Date of Patent: Mar. 5, 2024

(54) GENERATION OF LUNG BUD ORGANOIDS WITH BRANCHING STRUCTURES AND USES THEREOF FOR LUNG DISEASE MODELING

(71) Applicant: The Trustees of Columbia University in the City of New York, New York, NY (US)

(72) Inventors: Hans-Willem Snoeck, Brooklyn, NY (US); Ya-Wen Chen, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 482 days.

(21) Appl. No.: 16/495,557

(22) PCT Filed: Mar. 26, 2018

(86) PCT No.: PCT/US2018/024383
§ 371 (c)(1),
(2) Date: Sep. 19, 2019

(87) PCT Pub. No.: WO2018/176044
PCT Pub. Date: Sep. 27, 2018

(65) Prior Publication Data
US 2020/0093959 A1    Mar. 26, 2020

Related U.S. Application Data

(60) Provisional application No. 62/476,335, filed on Mar. 24, 2017.

(51) Int. Cl.
| | | |
|---|---|---|
| *C12Q 1/02* | (2006.01) | |
| *A61L 27/36* | (2006.01) | |
| *A61L 27/38* | (2006.01) | |
| *A61L 27/52* | (2006.01) | |
| *C12N 5/071* | (2010.01) | |
| *G01N 33/50* | (2006.01) | |

(52) U.S. Cl.
CPC ....... *A61L 27/3633* (2013.01); *A61L 27/3834* (2013.01); *A61L 27/3882* (2013.01); *A61L 27/3895* (2013.01); *A61L 27/52* (2013.01); *C12N 5/0689* (2013.01); *C12Q 1/025* (2013.01); *G01N 33/5082* (2013.01); *A61L 2430/22* (2013.01); *C12N 2501/117* (2013.01); *C12N 2501/119* (2013.01); *C12N 2501/385* (2013.01); *C12N 2501/415* (2013.01); *C12N 2503/04* (2013.01); *C12N 2506/02* (2013.01); *C12N 2506/45* (2013.01); *C12N 2513/00* (2013.01); *C12N 2533/90* (2013.01); *G01N 2500/10* (2013.01)

(58) Field of Classification Search
None
See application file for complete search history.

(56) References Cited

U.S. PATENT DOCUMENTS

| | | |
|---|---|---|
| 2015/0247124 A1 | 9/2015 | Snoeck et al. |
| 2015/0284689 A1 | 10/2015 | Nigam |
| 2015/0329829 A1* | 11/2015 | Shen ............... G01N 33/57434 435/405 |
| 2016/0168535 A1 | 6/2016 | Snoeck et al. |
| 2016/0237401 A1 | 8/2016 | Vallier et al. |

OTHER PUBLICATIONS

Huang et al., Nature Biotechnology, 2014, 32(1):84-91. (Year: 2014).*
Chen et al., Modeling human branching morphogenesis using human embryonic stem cells, The New York Stem Cell Foundation ( NYSCF) Conference, Oct. 2015. (Year: 2015).*
Varner et al., PNAS, 2015, 112(30):9230-9235. (Year: 2015).*
Noble, P.W., Barkauskas, C.E. & Jiang, D. Pulmonary fibrosis: patterns and perpetrators. J Clin Invest 122, 2756-2762 (2012).
Ryu, J.H. et al. Idiopathic pulmonary fibrosis: evolving concepts. Mayo Clinic proceedings 89, 1130-1142 (2014).
King, T.E., Jr. et al. A phase 3 trial of pirfenidone in patients with idiopathic pulmonary fibrosis. The New England Journal of Medicine 370, 2083-2092 (2014).
Richeldi, L. et al. Efficacy and safety of nintedanib in idiopathic pulmonary fibrosis. The New England Journal of Medicine 370, 2071-2082 (2014).
McCurry, K.R. et al. Lung transplantation in the United States, 1998-2007. Am J Transplant 9, 942-958 (2009).
Huang, S. et al. The in vitro Generation of Lung and Airway Progenitor Cells from Human Pluripotent Stem Cells. Nat Protoc. 2015; 10(3): 413-425.
Dye, B. Applying Principles of Developmental Biology to Generate Three-Dimensional Lung Organoids From Human Pluripotent Stem Cells. Dissertation. University of Michigan. Jun. 10, 2016, pp. 1-205.
Fitzgerald, M. et al. ABCA3 Inactivation in Mice Causes Respiratory Failure, Loss of Pulmonary Surfactant, and Depletion of Lung Phosphatidylglycerol. Journal of Lipid Research. (Dec. 1, 2006), 2007, vol. 48: 621-632.
Snoeck Laboratory. Modeling Human Lung Development and Disease. Oct. 17, 2016, pp. 1-3, downloaded from the internet<https://web.archive.org/web/20161017213202/http://www.snoecklabstemcells.org:80/human-lung-development> on Jun. 22, 2018.

(Continued)

*Primary Examiner* — Allison M Fox
(74) *Attorney, Agent, or Firm* — Leason Ellis LLP

(57) ABSTRACT

Described herein are new methods for making lung bud organoids (LBOs) that have the capacity of developing into branching airways and alveolar structures that a least partially recapitulate human lung development from mammalian, preferably human, pluripotent stem cells including embryonic stem cells (ESCs) and induced pluripotent stem cells (IPSC), either by culturing branched LBO in a 3D matrix or by transplanting the LBO under the kidney capsule of immune deficient mice. Branched LBOs contain pulmonary endoderm and mesoderm compatible with pulmonary mesenchyme, and undergo branching morphogenesis. Also described are LBOs harboring certain mutations that induce a fibrotic phenotype, and methods of making same. The mutated (B)LBOs can be used for screening agents that may treat pulmonary fibrosis.

14 Claims, 39 Drawing Sheets
Specification includes a Sequence Listing.

(56) References Cited

OTHER PUBLICATIONS

Firth, A. et al. Functional Gene Correction for Cystic Fibrosis in Lung Epithelial Cells Generated from Patient iPSCs. Cell Rep. 2015, 12(9), pp. 1385-1390.
Hynds, R. et al. The Relevance of Human Stem Cell-Derived Organoid Models for Epithelial Translational Medicine. Stem Cells. Dec. 3, 2012, 2013, 31(3), pp. 417-422.
Miller, A. et al. In vitro Induction and in vivo Engraftment of Lung Bud Tip Progenitor Cells Derived from Human Pluripotent Stem Cells. bioRxiv preprint. Feb. 15, 2017, pp. 1-63.
Giddings, A. et al. A Disease-Relevant High-Content Screening Assay to Identify Anti-Inflammatory Compounds for Use in Cystic Fibrosis. Journal of Biomolecular Screening. 2010, vol. 15, pp. 1204-1210.
Chen, Y. et al. A Three-Dimensional Model of Human Lung Development and Disease From Pluripotent Stem Cells. Nat Cell Biol. May 2017, vol. 19, pp. 542-549.
International Search Report and Written Opinion of PCT/US2018/024383 dated Jul. 17, 2018.
Dye B R et al.: "In vitro generation of human pluripotent stem cell derived lung organoids", ELI FE, vol. 4, E05098, Mar. 24, 2015 (Mar. 24, 2015).
Dye B R et al: "A bioengineered niche promotes in vivo engraftment and maturation of pluripotent stem cell derived human lung organoids", ELI FE, vol. 5, E19732, Sep. 28, 2016 (Sep. 28, 2016).
Tan Qi et al: "Human airway organoid engineering as a step toward lung regeneration and disease modeling ", Biomaterials, vol. 113, Jan. 2017 (Jan. 2017), pp. 118-132.
Extended European Search Report of corresponding application EP 18771973.7, dated Jan. 28, 2021.
Snoeck HW, Modeling human lung development and disease using pluripotent stem cells, Excellence Cluster Cardio-Pulmonary System (ECCPS) Symposium 2016, New Perspectives in Cardio-Pulmonary Research, Jun. 2016.
Chen et al., A three-dimensional model of human lung development and disease from pluripotent stem cells, Columbia University Department of Medicine Annual Research Day, 2016.
Chen et al., Three-dimensional model of human lung development from pluripotent stem cells, Columbia University Stem Cell Day, May 2016.
Chen et al., Modeling human branching morphogenesis and alveologenesis using human pluripotent stem cells, International Society for Stem Cell Research (ISSCR) annual meeting, Jun. 2016.
Chen et al., Modeling human branching morphogenesis using human embryonic stem cells in vivo, Columbia University Stem Cell Day, May 2015.
Chen et al., Modeling Human Branching Morphogenesis Using Humane Embryonic Stem Cells in Vivo, International Society for Stem Cell Research (ISSCR) annual meeting, Jun. 2015.
Chen et al., Modeling human branching morphogenesis in vivo, Columbia University Department of Medicine Annual Research Day, 2015.
Chen et al., Modeling human branching morphogenesis in vivo, Endoderm Lineages in Development and Disease, Keystone Symposia 2015 Conference, Feb. 2015.
Snoeck et al., Modeling, pathogenesis and treatment of idiopathic pulmonary fibrosis, NHLBI Progenitor Cell Translational Consortium (PCTC), Dec. 2016.
Chen et al., A three-dimensional model of human lung development and disease from pluripotent stem cells, Columbia University Medicine Grand Run, Mar. 2017.
Chen et al., Modeling human branching morphogenesis using human embryonic stem cells, Columbia University seminar, Jun. 2015.
Chen et al., Modeling distal lung development using human pluripotent stem cells, Columbia Center for Translational Immunology (CCTI) meeting, Oct. 2015.

* cited by examiner

FIG. 4A
FIG. 4B
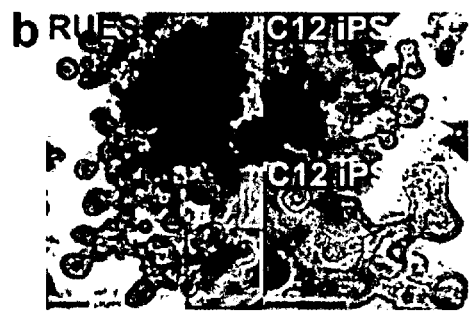
FIG. 4C
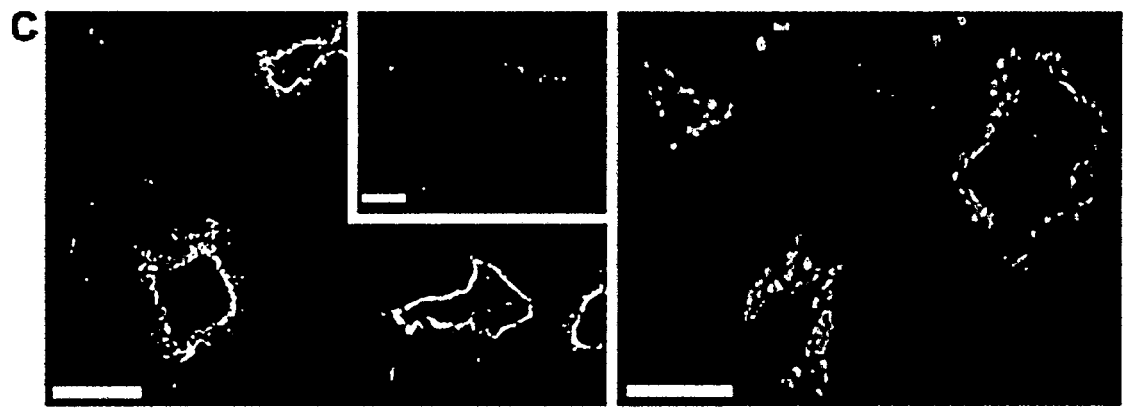
FIG. 4D
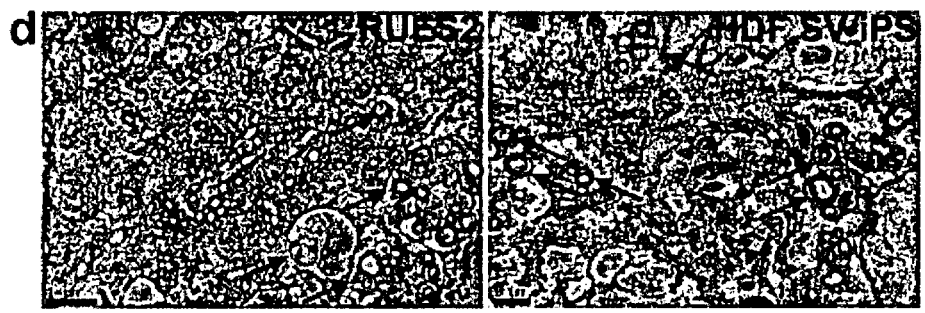

FIG. 7A
FIG. 7B
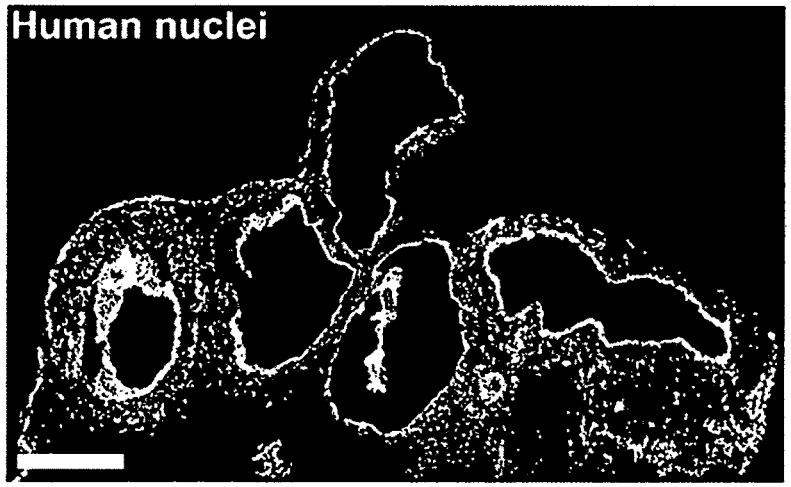
FIG. 7C
FIG. 7D

FIG. 10A

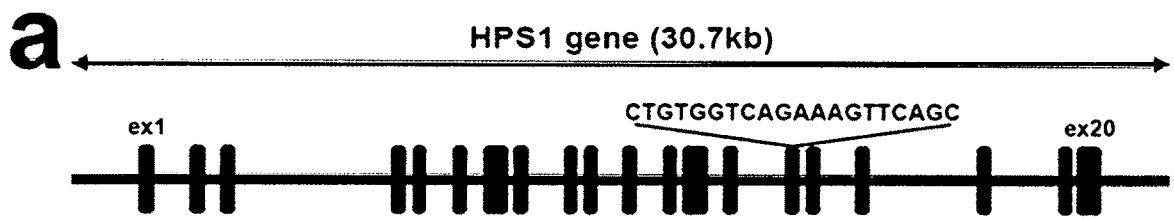

WT     21 AAGCTGAAGCGGCAGCTCTGCGCCATCTACCGGCTGAACTTTCTGACCACAGCCCCCA 78

C6-1   21 AAGCTGAAGCGGC-------------------GAACTTTCTGACCACAGCCCCCA 78

WT     21 AAGCTGAAGCGGCAGCTCTGCGCCATCTACCGGCTGAACTTTCTGACCACAGCCCCCA 78

C6-2   21 AAGCTGAAGCGGCAGC----------------------------------CCA 78

WT  ctgctccaggcatgtgggaagctgaagcggcagctctgcgccatctaccggctgaactttctgaccacagccccca gcaggggaggccacacctgccccagcacctgcaggaccaagtg
    L  L  Q  A  C  G  K  L  K  R  Q  L  C  A  I  Y  R  L  N  F  L  T  T  A  P  S  R  G  G  P  H  L  P  Q  H  L  Q  D  Q  V
    cagaggctcatgcgggagaagctgacggactggaaggacttcttgctggtgaagagcagg aggaacatcaccatggtg
    Q  R  L  M  R  E  K  L  T  D  H  K  D  F  L  L  V  K  S  R  R  N  I  T  M  V C6-1 ctgctccaggcatgtgggaagctgaagcggcgaactttctgac
     L  L  Q  A  C  G  K  L  K  R  R  T  F  -

C6-2 ctgctccaggcatgtgggaagctgaagcggcagcccccagcaggggaggcccacacctgc cccagcacctgcaggaccaagtgcagaggctcatgcgggagaagctgacggactggaagg
     L  L  Q  A  C  G  K  L  K  R  Q  P  P  A  G  E  A  H  T  C  P  S  T  C  R  T  K  C  R  G  S  C  G  R  S  -  R  T  G  R ——— exon15
——— exon16

Fig. 11: Schematic of lung development.

FIG. 13A

AP3B1 Exon 4

Lenght: 656bp

TGATCCTCCTGCCTCAGCCTCCTGTGTAGCTGGGA<u>CTAGAAGGATGTAGGCATGCCTGG</u>
CTTCTTTCTTTTATTTTTATCCCTCATTTGAAATATTTTACAATTAGTTAATATTC
TTATATGAGATCTGCTCAGGGATTTTTATTCCCTCAAGAGGAAGGACACTTTGATAG
GCTATTGCTATTGTGAACTGGACTATTAAAATGCTTACTTAAAAGCTTTCCTGTGTA
CTTATTATCCCACAAAAATATTATTTTATTTTACAATCTAACATGTGACCAGATTCAGTT
ATTTACTTGAGAAGAATTGAGCATGATTTTGGTATAGCAAATACTGAGTTTTAAATTTT
CACTCTGGTTATGAATAAATGATTTTTTTTAACAGATCAAGAAGTTGGTATATGTTTAC
CTGGTTCGATATGCTGAAGAACAGCAGGATCTTGCACTCCTGTCCATAAGCACTTTTCAG
CGAGCTCTGAAGGTAAATAATGGAGTGAGTGGCAAATATCCACTAAATAGCACCAGTAGTGTCTT
TGAAAGTGTGTCAGTTAAAGAAGTGGAGCGATAATCAGTACACTTAGAAAATAATTATACAA
GAAAGAGTTAAAAGCCTCCTATAGTGCCTACTCAGTACACTTAGTGTTTGTTTATATTCAATATAA
<u>CCAAGTGAAACTTGCTGTATATGTTACAGAG</u>TTCTGTATGTTTGTTTATATTCAATATAA

■ Genotyping Primer
□ Exon 4
■ gRNA

FIG. 13B

Sequencing

| HPS2-WT        | CAGCAGGATCTTGCACTCCTGTCC-ATAAGCACTTTTCAGCGAG |
| HPS2-clone-3-2 | CAGCAGGATCTTGC--------------------ACTTTTCAGCGAG |
| HPS2-clone-3-5 | CAGCAGGATCTTGCACTCCTGTCCCATAAGCACTTTTCAGCGAG |
| HPS2-clone-3-8 | CAGCAGGATCTTGCACTCCTGTC------GCACTTTTCAGCGAG |
|                | ************** ************ |

FIG. 14A

BLOC1S3 Exon2                                                   Lenght: 510bp

ACTCGGGGCCCCAGATCCTTGTTCGAGCTGGTCTTCAGTTTCCCATCTGTACGCTGAAGA
GCCTGGGGTCCAGTAACCCCATCACCCAGTTTACAGAGAAACTGAGGCCCAG
ACGGGGAGCAGCTGACACCAAGTCGTTAAGAGAATCAGCGAAGGGCTGGGAATCCAGGA
CCTGCCGCTTTTACCCACGGCGCCGGTCTCACGTGCAGTCCCTTCGCTCTTCTCCCC
TAGTTCGGTGCCATGGCGTCCCAGGGTCGTCGGGCGGGCGAGGCCCCTGCGGAGGCCGAGACG
GTGGTGCCGGGGGAGGCGACGGAGACGATTCCGAGCGCTCTGCGTCCTCGTCGGAGGAG
GAGGAGCTGTACCTGGGTCCTTCGGGCCGACTCGGAGACCGACTCGGAGCCGACTGAACCGACG
GCTGGGGAAGCCGCGGAGACCGACTCGGAGCCGACGCGCCG
CCGAGGGACCTGCCTCCACTCGTGTGCAGCGGGAATCGGCGAGGAGGCCTGGGGCACG

■ Genotyping Primer
☐ Exon 2
■ gRNA
■ ATG - start codon

FIG. 14B

Sequencing

| HPS8-WT         | CTGCGTCCTCGTCGGAGGAGGAGGAGCTGTACCTGGGTCCTTCGGGC |
| HPS8-clone-4-38 | CTGCGTCCTCGTCGG----------GCTGTACCTGGGTCCTTCGGGC |
|                 | *************** ******************             |

| HPS8-WT         | CTGCGTCCTCGTCGGAGGAGGAGGAGCTGTACCTGGGTCCTTCGGGC |
| HPS8-clone-4-11 | CTGCGTCCTCGTCGGT--TCGAGGAGCTGTACCTGGGTCCTTCGGGC |
|                 | ****************  : ***************             |

FIG. 15

SFTPC Exon 2

Lenght: 405bp

☐ Genotyping Primer
☐ Exon 2
☐ gRNA

CTCCTCAGCCCTTCCCTGTCCATCCATCGCATCGGCTGTCCAGCCCTAGGCAGCCGTGGG
AGGGTGTTCAGCTTGTATAGGGAGAAGAGGGACAGCCTCATGACCTCATGCCCTGTCTCC
TTGCCTGCCCACCGTGTCAGGACTACTCCGCAGCTCCGGGGCCGATTTGGCATTCCC
TGCTGCCCAGTGCACCTGAAACGCCTTCTTATCGTGGTGGTGGTCCTCATCGTC
GTGGTGATTGTGGGAGCCCTGCTCTCCACATGAGCCAGAAACACACGGAGATG
GTGAGAGGTGTGGATGCACAGCAGTGGGACATGGGACAGCAGGGCTAGGTG
GGATGGGCGATAGAGAAACTGTCCAAGGGAGTGAGGGGAGGAGGCAAGGGGCACAGCTA

FIG. 16 A

```
GTTCCCCCCAACCAGCCCGCCCGAGAGAGTGACTCTCACGAGAGCCGCGAGAGTCAGCTT
GGCCAATCCGTGCGGTCGGCGGCCGCTCCCTTTATAAGCCGACTCGCCCGGCAGCGCACC
GGGTTGCGGAGGGTGGGCCTGGGAGGGGTGGTGGCCATTTTTTGTCTAACCCTAACTGAG
AAGGGCGTAGGCGCCGTGCTTTTGCTCCCCGCGCGCTGTTTTTCTCGCTGACTTTCAGCG
GGCGGAAAAGCCTCGGCCTGCCGCCTTCCACCGTTCATTCTAGAGCAAACAAAAAATGTC
AGCTGCTGGCCCGTTCGCCCTCCCGGGGACCTGCGGCGGGTCGCCTGCCCAGCCCCGA
ACCCCGCCTGGAGGCCGCGGTCGGCCCGGGCTTCTCCGGAGGCACCCACTGCCACCGCG
AAGAGTTGGGCTCTGTCAGCCGCGGGTCTCTCGGGGGCGAGGGCGAGGTTCAGGCCTTTC
AGGCCGCAGGAAGAGGAACGGAGCGAGTCCCCGCGCGCGGCGCGATTCCCTGAGCTGTGG
GACGTGCACCCAGGACTCGGCTCACACATGCAGTTCGCTTTCCTGTTGGTGGGGGAACG
CCGATCGTGCGCATCCGTCACCCCTCGCCGGCAATGGGGCTTGTGAACCCCCAAACCTG
ACTGACTGGGCCAGTGTGCTGCAAATTGGCAGGAGACGTGAAGGCACCTCCAAAGTCGGC
CAAAATGAATGGGCAGTGAGCCGGGGTTGCCTGGAGCCGTTCCTGCGTGGGTTCTCCCGT
CTTCCGCTTTTTGTTGCCTTTTATGGTTGTATTACAACTTAGTTCCTGCTCTGCAGATTT
```

Lenght: 510bp

☐ Genotyping Primer
☐ Exon 2
☐ gRNAs 3 (upper) and 4 (lower)
■ telomere template sequence

FIG. 16B

```
TERC-WT            AAGGGCGTAGGCGCCGTGCTTTTGCTCCCCGCGCTGTTTTCTCGCTGACTTTCAGCG
TERC-clone-3-28    AAGGGCGTAGGCGCCGTGCTTTTGCTCCCCGCGCTGTTTTTCTCGCTGACT------
                   ******************************************* *******

TERC-WT            GGCGGAAAAGCCTCGGCCTGCCGCCTTCCACCGTTCATTCTAGAGCAAACAAAAATGTC
TERC-clone-3-28    ---------------------------------------TCATTCTAGAGCAAACAAAAATGTC
                                                          ******************

TERC-WT            AGCTGCTGGCCCGTTCGCCCCTCCCGGGGACCTGCGGCGGGTCGCCTGCCCAGCCCCCGA
TERC-clone-4-11    AGCTGCTGGCCCGTTCGCCCCT---------------------------------------
                   *********************

TERC-WT            ACCCCGCCTGGAGGCCGCGTCGGCCCGGGGCTTCTCCGGAGGCACCCACTGCCACCGCG
TERC-            ---------------------CCCGGGGCTTCTCCGGAGGCACCCACTGCCACCGCG
4-11                                  ********************************
```

GENERATION OF LUNG BUD ORGANOIDS WITH BRANCHING STRUCTURES AND USES THEREOF FOR LUNG DISEASE MODELING

CROSS REFERENCE TO RELATED APPLICATIONS

This application is a 371 national stage application of International Application No. PCT/US2018/024383 filed on Mar. 26, 2018, which claims priority to U.S. Provisional Application Ser. No. 62/476,335, filed on Mar. 24, 2017, the contents of each of which are incorporated herein by references in their entirety.

STATEMENT OF GOVERNMENTAL INTEREST

This invention was made with government support under grant HL134760 awarded by the NIH. The government has certain rights in the invention.

SEQUENCE LISTING

The application contains a Sequence Listing which has been submitted electronically in ASCII format and is hereby incorporated by reference in its entirety. Said ASCII copy, created on Sep. 18, 2019, is named 01001-006744-US1_ST25.txt and is 2,000 bytes in size.

BACKGROUND OF THE INVENTION

Idiopathic pulmonary fibrosis (IPF) is an intractable interstitial lung disease with a median survival of 3 to 4 years, characterized by fibroblastic foci and remodeling and obliteration of alveoli[1,2] The only definitive treatment is lung transplantation, an intervention hampered by low availability of donor organs, and severe surgical, medical and immunological complications.[3] Innovative approaches are therefore urgently needed. Developing such approaches requires sorely lacking insight into the pathogenesis of this devastating and increasingly prevalent disease and establishment of platforms for drug discovery.

BRIEF DESCRIPTION OF THE DRAWINGS

The present invention is illustrated by way of example, and not by way of limitation, in the figures.

(FIG. 1A) Development of adherent structures during ventralization of AFE between d6 and d8 (see protocol FIG. 6b), that could be expanded in suspension culture (d10, d20). Representative of >50 independent experiments (ESCs and iPSCs). Scale bars 250 µm. (FIG. 1B) Cellular expansion during the generation of LBOs. N=3 independent triplicate experiments in RUES2 ESCs. (FIG. 1C) Expression of EPCAM, KRT8, NKX2.1, FOXA1, and P63 in d25 LBOs. Representative of >10 independent experiments in ESCs and iPSCs. Scale bars 100 µm. (FIG. 1D) Staining of d25 LBO for ECADH and PDGFRA. Representative of 3 independent experiments in RUES2 ESCs. Scale bar 250 µm. (FIG. 1E) Expression of endodermal and mesodermal markers in the EPCAM$^+$ and EPCAM$^-$ fraction of d25 LBOs determined by RNAseq (3 independent biological replicates, RUES2 ESCs).

(FIG. 2A) Macroscopic aspect of growths 1.5 months after transplantation of $10^6$ LBO cells embedded in MATRIGEL® under the kidney capsule of NSG mice. Scale bar 1 cm. (FIG. 2B) HE stain of LBO-derived growth 1.5 months after transplantation. Scale bar 500 µm. (FIG. 2C) Immunofluorescence for indicated markers in LBO-derived growths 1.5 months after transplantation. Scale bars 100 µm. (FIG. 2D) HE staining of LBO-derived growths 5 months after transplantation. Scale bars 250 µm. (FIG. 2E) Immunofluorescence for indicated markers in LBO-derived growth 5 months after transplantation. Scale bars 250 µm. (FIG. 2F) Dot blots for proteins marked on the left in aspirates from tubules in LBO-derived growth 5 months after transplantation. (FIG. 2G) HE staining and immunofluorescence for indicated markers in LBO-derived growths 7 months after transplantation. Scale bars 100 µm. All panels used RUES2 ESCs, representative of 4 independent experiments.

(FIG. 3A) Bright field images of the development of an LBO into a branching structure after plating in MATRIGEL®. RUES2 ESCs. Representative of >50 independent experiments. Scale bars 500 µm. (FIG. 3B) Immunofluorescence staining for indicated markers in d70 RUES2-derived LBOs plated in MATRIGEL® at d25. Representative of 4 independent experiments. Scale bars 250 µm.

FIGS. 4A-4G. Long-term development of LBOs in vitro. (FIG. 4A) Macroscopic appearance of d170 RUES2 LBOs embedded in MATRIGEL® at d25. Representative of >50 independent experiments. Scale bar 5 mm (FIG. 4B) Bright field images of d170 RUES2 and C12 LBOs embedded in MATRIGEL® at d25. Representative of >50 independent experiments. Scale bars 500 µm. (FIG. 4C) Immunofluorescence for indicated markers in d170 RUES2 LBOs embedded in MATRIGEL® at d25. Representative of 3 independent experiments. Scale bars for MUC1+SFTPB and HT2-280 100 µm. Scale bar for SFTPC 10 µm. (FIG. 4D) Electron microscopy of d170 LBOs embedded in MATRIGEL® at d25 in RUES2 ESCs and HDF SV iPSCs. Arrows indicate LBs. Representative of 3 independent experiments. (FIG. 4E) Uptake of SFTPB-BODIPY (green) in d170 LBOs embedded in MATRIGEL® at d25. Representative of 4 independent experiments. Scale bars 100 µm. (FIG. 4F) Time-course of uptake of SFTPB-BODIPY in d170 LBOs embedded in MATRIGEL® at d25 (mean±s.e.m, n=4 independent experiments in RUES2 ESCs). (FIG. 4G) Comparison of genome-wide expression in d170 LBOs derived from hESCs and hiPSCs (12 biologically independent samples) with the KeyGenes database, showing the best match with second trimester human lung.

(FIG. 5A) Confocal images of whole mount d170 LBOs 1 and 2 days after infection with RSV and stained using anti-RSV (all antigens) antibody. Arrows: infected cells in the lumen. Representative of 3 independent experiments. Scale bars 100 µm. (FIG. 5B) Bright field images of d50 LBO-derived MATRIGEL® colonies from RUES2 and RUES2-HPS1 cells. Representative of six independent experiments. Scale bars 500 µm. (FIG. 5C) Fraction of EPCAM$^+$ and EPCAM$^-$ cells in d50 LBO-derived colonies in 3D MATRIGEL® cultures of RUES2 and RUES2-HPS1 cells. (n=6, mean±s.e.m of 3 technical replicates from two experiments; *P<0.0001; two-tailed Student's t-test). (FIG. 5D) Immunofluorescence staining for mesenchymal markers and ECM components in 3D MATRIGEL® cultures of RUES2 and RUES2-HPS1 cells. Representative of 3 independent experiments. Scale bars 500 µm.

(FIG. 6A) Published 2D directed differentiation protocol for the generation of lung and airway epithelial cells. (FIG. 6B)

Schematic overview of the protocol for generating and differentiating LBOs. (FIG. 6C) Unsupervised clustering of RNAseq data generation from EPCAM$^+$ and EPCAM$^-$ cells isolated from d25 RUES2 LBOs (3 independent biological replicates). (FIG. 6D) Expression SHH and of its transcriptional targets, GLI1, PTCH and HHIP, of genes expressed in AFE, in lung and airway, and in other AFE-derived lineages in d25LBOs (extracted from the RNAseq data shown in FIG. 6(c); n=3 independent experiments in RUES2 ESCs). (FIG. 6E) ISH for SHH in LBOs at d15, d20 and d25. Representative of 3 independent experiments, RUES2 ESCs. Scale bars 250 μm.

FIGS. 7A-7E. Potential of LBOs in vivo. (FIG. 7A) Staining of RUES2 ESC LBO-derived growths for human nuclei 1.5 months after transplantation under the kidney capsule of NSG mice. Scale bars 500 μm. (FIG. 7B) Staining of LBO-derived growths 5 months after transplantation for murine CD31 (mCD31). Scale bars 50 μm. (FIG. 7C) Staining of LBO-derived growths 5 months after transplantation for SMA and EPCAM. Scale bars 500 μm. (FIG. 7D) Hematoxyline-eosine stain of LBO-derived growths showing ciliated cells 5 months after transplantation under the kidney capsule of NSG mice. Scale bars 25 μm. (FIG. 7E) Hematoxyline-eosine stain of LBO-derived growths showing submucosal glands 5 months after transplantation under the kidney capsule of NSG mice. Scale bars 100 μm. All panels used RUES2 ESCs, representative of 4 independent experiments.

(FIG. 8A) Branching colonies in d70 cultures of LBOs derived from RUES2 and three different iPS lines plated at d25 in MATRIGEL® 3D culture in the presence of CHIR99021, BMP4, FGF7, FGF10, and RA. Representative of >10 independent experiments. Scale bar 100 μm. (FIG. 8B) Branching colonies 90 days after plating RUES2 LBOs in MATRIGEL® at 1 (top) or 4 LBOs (bottom) per 6.4 mm well. Scale bars 2.5 mm. All images are representative of >10 independent experiments. (FIG. 8C) Fraction of EPCAM$^-$ cells in LBOs (n=3 independent experiments, RUES2 ESCs). (FIG. 8D) Colonies from single cells of LBOs, and from EPCAM$^+$ and EPCAM$^-$ cells isolated from LBOs. Representative of 5 experiments. Scale bar 500 μm. (FIG. 8E) IF of colonies generated from single cells derived from LBOs in MATRIGEL® 3D culture. Representative of 5 experiments. Scale bars 500 μm, 25 μM for SFTPB and SFTPC.

(FIG. 9A) Morphology of d170 cultures of LBOs derived from three iPS lines plated at d25 in MATRIGEL® in the presence of CHIR99021, BMP4, FGF7, FGF10, and RA. Representative of >10 independent experiments. Scale bar 250 μm (FIG. 9B) Immunofluorescence images of a low magnification (tile scan) for indicated markers. Staining performed on serial sections of a d170 culture of LBOs derived from C12 iPS line plated at d25 in MATRIGEL® in the presence of CHIR99021, BMP4, FGF7, FGF10, and RA. Representative of 4 independent experiments. Scale bars 1 mm (FIG. 9C) Electron microscopy of d170 LBOs embedded in MATRIGEL® at d25 in HDF mRNA iPSCs. Arrows indicate LBs. Representative of 3 independent experiments. Scale bar 1 μm. (FIG. 9D) Hematoxylin-Eosin stain (left) and expression of SOX2 and SOX9 in week 14 distal human fetal lung (HFL). Note tubes that co-express SOX2 and SOX9 (arrows). Representative of 3 independent experiments. Scale bar 250 μm. (FIG. 9E) Hierarchical clustering of the genome-wide expression profile in d170 LBOs with genome-wide expression profiles of 2nd trimester human organs and tissues from the KeyGenes database.

FIGS. 10A-10H. Modeling of pulmonary fibrosis. (FIG. 10A) Schematic representation of the HPS1 gene, and location of sequence complementary to the gRNA (upper). Nucleotide sequence of wild type alleles in RUES2 and of both targeted alleles in RUES2-HPS1 cells in the region targeted by the gRNA (middle). Nucleotide and amino acid sequence of exons 15 and 16 of HPS1, showing deletions and premature stop codons in the targeted alleles of RUES2-HPS1 cells (lower). (FIG. 10B) Representative example of flow cytometric analysis of EPCAM$^+$ and EPCAM$^-$ cells in d50 LBO-derived colonies in 3D MATRIGEL® cultures of RUES2 and RUES2-HPS1 cells. (n=6, mean±s.e.m of 3 technical replicates from two experiments; *P<0.0001; two-tailed Student's t-test). (FIG. 10C) Tile scan images of immunofluorescence staining for EPCAM and PDGFRA of LBO-derived branching colonies in 3D MATRIGEL® cultures generated from parental RUES2 cells and from RUES2-HPS1 cells. Representative of five independent experiments. Scale bars 1 mm. (FIG. 10D) Representative example of the expression of the proliferation antigen Ki67 in EPCAM$^+$ and EPCAM$^-$ cells of d40 LBOs derived from parental RUES2 and mutant RUES2-HPS1 cells. Representative of three independent experiments. (FIG. 10E) Hydroxyproline content in LBO-derived colonies in 3D MATRIGEL® cultures of RUES2 and RUES2-HPS1 cells (mean±s.e.m, n=3 independent experiments; *P<0.05; two-tailed Student's t-test). (FIG. 10F) Quantification of collagens I and III and fibronectin in 3D MATRIGEL® cultures of RUES2 and RUES2-HPS1 cells using immunofluorescence intensity relative to DAPI (mean±s.e.m, n=3 independent experiments; *P<0.05 for fibronectin, *P<0.01 for collagens; two-tailed Student's t-test after normalizing RUES2 controls to 1 in each experiment). (FIG. 10G) LBOs at d25 of suspension culture after mixing ZsGreen$^+$ and mCherry$^+$ RUES2-derived cells at d4 or at d10 of the protocol shown in FIG. 6B. Representative of >5 independent experiments. (FIG. 10H) Fraction of EPCAM$^-$ cells derived from parental RUES2 or from mutant RUES2-HPS1 cells in d40 cultures after mixing of the cells at either d4 or d10 of the culture protocol (mean±s.e.m, n=3 independent experiments; *P<0.01 compared to parental RUES2 and to parental RUES2 mixed at d10 with RUES2-HPS1; one way ANOVA).

FIGS. 13A-13C. Targeted mutation of AP3B1. FIG. 13A shows the target AP3B1 (Exon 4) sequence that was mutated using Crispr/cas system. The darker gray boxes at the ends of the sequence represent the genotyping primer sequences and the medium gray sequence within the sequence represents the gRNA sequence. FIG. 13B shows resulting mutated sequences of select HPS2 clones. FIG. 13C represent a western blot showing that the mutated clones no longer produce HPS2.

FIGS. 14A-14C. Targeted mutation of BLOC1S3. FIG. 14A shows the target BLOC1S3 (Exon 2) sequence that was mutated using Crispr/cas system. The darker gray boxes at the ends of the sequence represent the genotyping primer sequences and the medium gray sequence within the sequence represents the gRNA sequence. FIG. 14B shows resulting mutated sequences of select HPS8 clones. FIG. 14C represent a western blot showing that the mutated clones no longer produce HPS8.

FIG. 15. shows the target SFTPC (Exon 2) sequence that was mutated using Crispr/cas system. The darker gray boxes at the ends of the sequence represent the genotyping primer sequences and the medium gray sequence within the sequence represents the gRNA sequence.

FIGS. 16A-16B. Targeted mutation of TERC. FIG. 16A shows the target TERC (Exon 1) sequence that was mutated using Crispr/cas system. The darker gray boxes at the ends of the sequence represent the genotyping primer sequences and the medium gray sequence within the sequence represents the gRNA sequence. The boxed sequence represents the telomere template sequence. FIG. 16B shows resulting mutated sequences of select TERC clones.

DETAILED DESCRIPTION

Figure 1A:
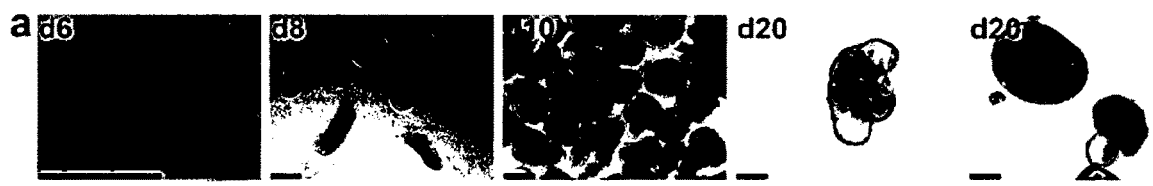
FIGS. 1A-1E. Generation of lung bud organoids.
Figure 1B:
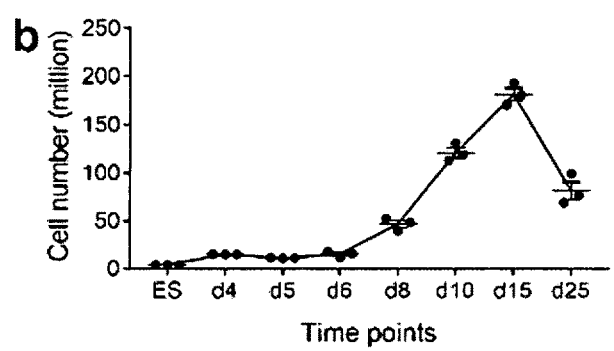

We have now developed new methods for making lung bud organoids (LBOs) that have the capacity of developing into branching airways and alveolar structures that at least partially recapitulate human lung development from mammalian, preferably human, pluripotent stem cells including embryonic stem cells (ESCs) and induced pluripotent stem cells (IPSC) either by culturing LBO in a 3D matrix (LBO-3D) or by xenotransplanting the LBO (LBO-xeno) such as under the kidney capsule of immune deficient mice. Branched LBOs (BLBOs) contain pulmonary endoderm and mesoderm compatible with pulmonary mesenchyme, and undergo branching morphogenesis. They develop predominantly into structures compatible with distal lung, i.e. alveolar structures containing alveolar epithelial cells, but also contain some more proximal, i.e. airway cells. Branched LBOs made by 3D culture are sometimes referred to as BLBO-3D, and those made in vivo by xenotransplantation are also referred to as BLBO-XENO.

As is shown in the results and explained in the Examples, development of LBO occurs in basically three stages:
Stage 1: suspension cultures of in vitro generated anterior foregut cells to form LBO that are spherical structures with folded epithelium (up to d25).
Stage 2: In 3D MATRIGEL® (e.g., a solubilized basement membrane preparation from the Engelbreth-Holm-Swarm (EHS) mouse sarcoma) culture, which starts at about d25, the unbranched LBO spheres start branching within one week. After xenotransplantation under the kidney capsule of immune deficient mice, branching takes longer and is observed about 2 months after grafting.
Stage 3: lastly, when cultured long-term as xenotransplant or 3D MATRIGEL® culture, the BLBOs begin to show dilated tips which have the morphogenesis of alveolar structures.

The longer the LBO are cultured (in either 3D or xenotransplants) the more developed is the branching morphogenesis. The LBO may be cultured in the 3D matrix for 20-270 days, or for at least 100 days. The xenotransplanted LBO may be cultured in vivo in the mouse for between about 30 days and 270 days. BLBO-3D cultures have been grown as long as 180 days and BLBO-xeno have been followed up to 7 months. There are more mature alveolar cells the longer the BLBO are grown and the organoids are larger, but the fibrosis phenotype in HPS1 cells (LBO-HPS1$^{DEL}$) is already obvious at d40.

Whether BLBO-3D or BLBO-xeno are used, drug screening will typically be done in vitro, using BLBO-3D followed by validation in vivo using BLBO-xeno.

Definitions

The term "human pluripotent stem cells (hPSCs)" as used herein refers to human pluripotent stem cells that may include embryonic stem cells (ESCs) and induced pluripotent stem cells (iPSCs). Derived from the inner cell mass of the blastocyst, ESCs can be maintained in a pluripotent state in vitro and have the potential to generate every cell type in the organism.[5] iPSCs are generated by reprogramming somatic cells to a pluripotent state similar to ESCs, and are therefore patient-specific. In a specific example, Embryonic stem cells or iPS cells are undifferentiated pluripotent stem cells, expressing OCT4, SOX2, NANOG, and SSEA4.

As used herein, "anterior foregut endoderm" (AFE) refers to endoderm that is anterior to the endoderm that gives rise to the liver. One of ordinary skill in the art will readily appreciate that "anterior foregut endoderm" thus includes, for example, pharyngeal endoderm or lung endoderm and other, more highly differentiated populations of endodermal cells. As embryonic tissues express characteristic sets of molecular markers. the various cell types encompassed by the term "anterior foregut endoderm" may exhibit different expression patterns of molecular markers. One of ordinary skill in the art will appreciate that "anterior foregut endoderm" gives rise to various tissues, e.g., tonsils, tympanic membrane, thyroid, parathyroid glands, thymus, trachea, esophagus, stomach, lung and larynx/pharynx. Anterior foregut endoderm expresses FOXA2, FOXA1, SOX2 and EPCAM and is negative for the distal endoderm marker CDX2.

As used herein, definitive endoderm (DE) is one of the three germlayers arising after gastrulation that give rise the intestinal tract, liver, pancreas, stomach and all other organs derived from the AFE, as listed above. DE expresses the markers: FOXA2, FOXA1, cKIT, CXCR4, EPCAM.

Figure 12:
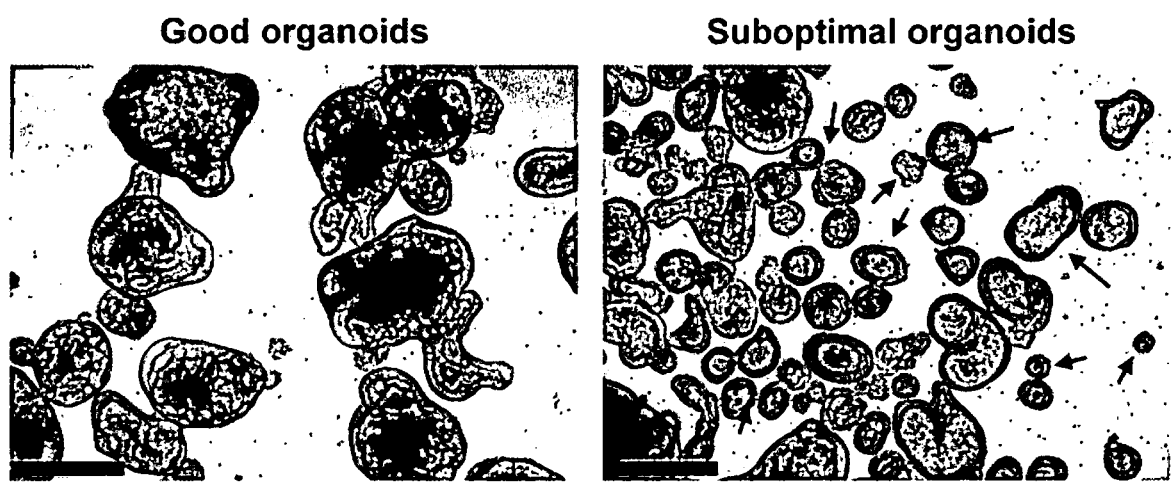
FIG. 12. Morphology of LBOs on d20. The left panel showed organoids with folding structures which have higher potential to generate branching structures in MATRIGEL®. The right panel showed suboptimal organoids (arrows) initiated with significantly lower cell number on d4 which have less potential to generate branching structures in MATRIGEL®. Representative images of organoids on d20 of RUES2, ESCs. Scale bars: 500 micrometer.
Figure 13C:
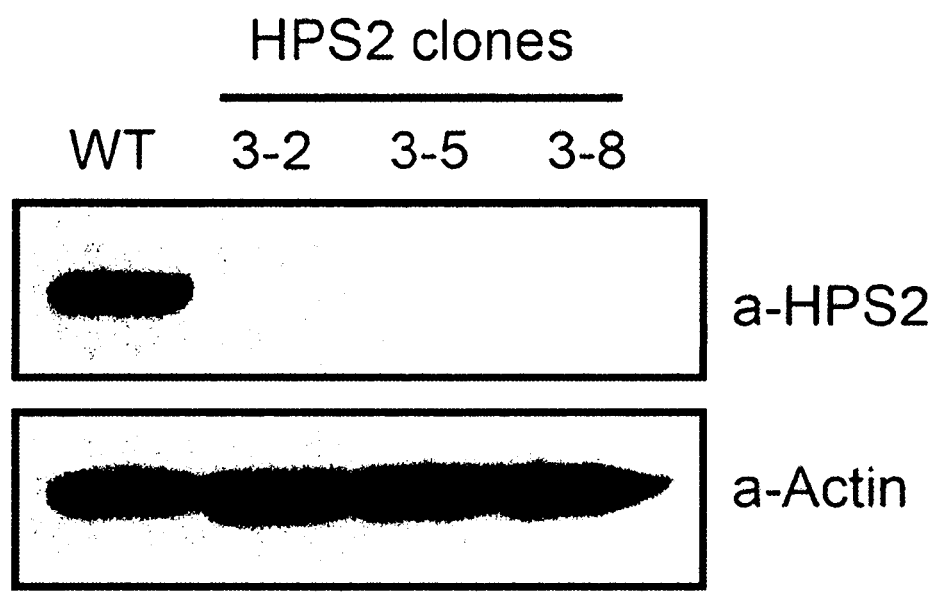
Figure 14C:
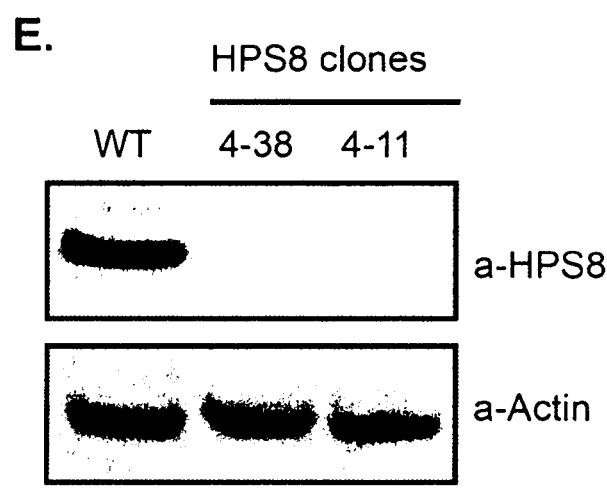

Lung bud organoid(s) (LBO(s)) are derived from human pluripotent stem cells in suspension and contain lung epithelial (expressing FOXA2, FOXA1, NKX2.1 and EPCAM) and mesenchymal progenitors (expressing PDGFRa, CD90, TBX4, HOXA5). Lung bud organoids will generate branching colonies after embedding in MATRIGEL®. LBOs are typically spheroids when generated from anterior foregut cells in suspension cultures, in vitro. LBOs typically form between d20-d25 and include folding structures inside organoids (see FIG. 12).

The term "branched LBO" (BLBO) as used herein refers to LBOs that possess structures relating to branching morphogenesis. As the BLBOs further develop they begin to show dilated tips which have the morphology of fetal alveolar structures.

The "term MATRIGEL® sandwich" as used herein refers to an arrangement of MATRIGEL® and LBOs that allows for 3-dimensional growth of LBOs into BLBOs. In one specific example, the arrangement involves a bottom portion of solidified MATRIGEL®, a mixed MATRIGEL®/LBO middle section and a top portion of solidified MATRIGEL® thereby resembling a sandwich configuration.

Embodiments of the Invention

Certain embodiments are directed to newly discovered lung bud organoids (LBOs) that possess features of lung branching morphogenesis. The LBOs disclosed herein are developed from pluripotent cells, such as embryonic stem (ES) cells or induced pluripotent cells (iPSCs), that are subjected to a series of different culture steps to orchestrate differentiation of the pluripotent cells into definitive endoderm (DE), anterior foregut epithelial (AFE) cells, and then ultimately into LBOs with folding structures (LBOfs). LBOfs (up to about 20-25 days in suspension culture), which express sonic hedgehog (SHH) on the tips of budding epithelial structures but lack branching structures. The LBOfs are then either xenotransplanted or embedded in a 3D MATRIGEL®. BLBO-3D have branching structures as described above that is less advanced morphologically than the branching observed in BLBO-xenotransplant that display branching airways and early alveolar structures, including type I alveolar epithelial cells and neuroepithelial bodies that are not observed in vitro in LGO-3D thus far. Both 3D and xenotransplant BLBOs contain mesoderm and pulmonary endoderm. Other embodiments are directed to methods of making these LBOs.

Other embodiments are directed to methods for making the LBOs and BLBOs and screening for a test agent that, for example can treat fibrosis modeled using LBOs or BLBOs having mutations such as HPS1, HPS2 SFTPC and TERC that are known to cause fibrosis. Cell lines with mutations of HPS3, 5, 8 and LYST, affect lysosome-related organelles but are not associated with clinical fibrosis; therefore these lines can be used as controls.

Use of CRISPR/Cas System to Generate or Correct Lung Disease Related Gene Mutations.

The term "CRISPR" as used herein as an abbreviation for Clustered Regularly Interspaced Short Palendromic Repeat, a region in bacterial genomes used in pathogen defense. The term "Cas" as used herein refers to an abbreviation for CRISPR Associated Protein; the Cas9 nuclease is the active enzyme for the Type II CRISPR system. The term "gRNA" as used herein refers to a guide RNA, that provides both targeting specificity and scaffolding/binding ability for Cas9 nuclease. The term "gRNA sequence" as used herein refers to the 20 nucleotides that precede the PAM sequence in the targeted genomic DNA. The term "PAM" as used herein refers to Protospacer Adjacent Motif, which is a required sequence that must immediately follow the gRNA sequence. Accordingly, the term "CRISPR/cas system" as used herein is refers a system that involves use of the RNA-guided nuclease, Cas, that is directed to a gRNA sequence by gRNA to edit a gene. The genetically corrected or mutated cell line is then developed into LBOs according to the techniques described herein.

BLBOs have also been generated from pulmonary RUES2 stem cells engineered with mutations made using CRISPR/Cas9 carrying a deletion of the HPS1 gene (hereafter "RUES2-HPS1$^{DEL}$ cells) (FIG. 10) which predisposes the cells with high penetrance to IPF.[22, 44] and therefore allowed recapitulation of fibrosis in vitro in hPSCs. Using genome-edited ESCs avoided issues of incomplete reprogramming and background genetic variation typically associated with iPSCs.[45] Mutated LBOs form with an abnormal morphology indicative of a fibrotic phenotype as is seen in subjects with HPS1 mutations having fibrosis.

Other mutated cells lines that were made to study lung diseases including fibrosis, surfactant secretion disease, e.g. ABCA3 mutation, or cystic fibrosis. Cell lines made with HPS 2, HPS 3, HPS 5, HPS8 and telomerase mutated pluripotent cells are described below. LBOs grown from these cell lines are also embodiments of the invention.

HPS1 (OMIM #604982): HPS1 is part of BLOC3, and this mutation is the most penetrant for PF (currently 80%).[21] Multiple mutations have been described, all of which eliminate BLOC3. There is a frame shift hot-spot at codons 321-322.[143, 144] We have already successfully targeted this region, and used this line to demonstrate that fibrosis can be elicited in vitro.

HPS2 (OMIM #608233): HPS2 mutation destabilizes the AP3 complex, and also predisposes to fibrosis. As multiple deletions and frame shifts in AP3B1 cause nonsense-mediated mRNA decay, thus deleting the entire protein and the AP3 complex,[59, 145] we introduced deletion in the 5' region. By light microscopic observation, the HPS2 mutated LBO-3D cultures appear fibrotic mimicking the expected result.

HPS8 (OMIM #614077): Mutation in BLOC1S3, part of the BLOC1 complex, causes a form of HPS that is not associated with IPF and serves as a control. The initial mutation described is a 1bp frameshift deletion that theoretically gives rise to abnormal 244 aa protein as nonsense-mediated mRNA decays was not observed.[146] Another human mutation however did show nonsense-mediated mRNA decay, with mRNA undetectable.[147] Deletion of the gene by targeting the 5' region for frameshift mutation has therefore been performed. By light microscopy, the LBO-3D organoids appear to develop dilated branch tips, which might be suggestive of abnormal surfactant secretion. All HPS genes play a role in the biogenesis of lysosome-related organelles, including lamellar bodies of type II alveolar epithelial cells, and HPS8 may have a surfactant secretion phenotype in vitro.

Telomerase (OMIM #614742): Mutations in telomerase components cause shortening of telomeres in iPS cells that correlate with clinical phenotype of the patients whose cells were reprogrammed[151, 152] Importantly, alternative lengthening of telomeres does not appear to occur in hPSCs.[151] Because IPF is the most common clinical manifestation of mutation in telomerase genes,[133] introduction of telomerase mutations into hESCs is a valid strategy to examine the effect of telomeropathy on ATII cell function. A broad variety of mutations in both hTERT and hTERC are associated with short telomere syndromes that are clinical indistinguishable, the main determinant of the clinical manifestations being actual telomere length.[133] We have introduced heterozygous and double heterozygous indels in the N-terminal region of hTERC. Telomere length was verified over successive passages by telomere FISH. Cells from early and late passages (>15), which show significantly shortened telomeres,[152] were used. TERC-deleted lines have been made. The form very small LBOs that appear fibrotic by light microscopy as was expected.

The following lines are also developed according to the teachings herein: HPS5 (OMIM #607521). HPS5 is not associated with interstitial lung disease and will serve as a control and similar to HPS3, encodes a protein of the BLOC2 complex. The only mutation known in humans is a homozygous 4-bp deletion (AGTT) at codons leu675 to va1676. The mutation resulted in a frameshift with truncation of the nonsense polypeptide at codon 682, causing loss of 40% of the protein at the C terminus.

HPS3 (OMIM #060118): HPS3 is not associated with interstitial lung disease, and will serve as a control. HPS3 is caused, among others, by a large deletion in the HPS3 gene, which is part of the BLOC2 complex. 57 As the corresponding mRNA and the BLOC2 complex are absent,[57] full deletion in the 5' region was performed.

LYST: (OMIM #606897): Multiple frame shift mutations have been described that give rise to severe childhood onset CHS with confirmed giant granules in white blood cells and melanocytes.[64, 148-150] We will create an indel at Lys633/Lys634, which results in a premature stop a codon 638.

SFTPC (OMIM #178620): We will introduce heterozygous T→A transversion in nucleotide 128 of exon 5, using a guide RNAs and a homologous single stranded 80 bp DNA segment containing the point mutation. This heterozygous mutation caused highly penetrant IPF in a Dutch family.[11] For SFTPC it is essential, though more challenging and less efficient, to introduce that specific mutation observed in patients, as proteotoxicity caused by an aberrantly folded protein, not absence of the protein, causes disease.[4, 5, 67]

Conversely, iPSCs such as the C12 line discussed above derived from patients harboring a lung disease related genetic mutation can be corrected, in vitro, using Crispr/cas system to produce a genetically corrected cell line. Production of LBOs using cells that have been genetically altered for the intended purpose of correcting a genetic defect provides a viable method of testing such genetic alterations for their capacity to correct the disease phenotype.

The term "lung-disease related mutation" as used herein relates to a gene mutation or polymorphism known to cause a lung disease phenotype. For example, certain lung diseases are caused by gene mutations in the following, non-exhaustive list of genes: HPS1, 2, 4, hTERT, hTERC, dyskerin, CFTR, DKC1, SFPTB, SFTPC, SFTPA1, SFTPA2, MUC5B, SHH, PTCH, SMO, ABCA3. The gene ID Nos for these genes is provided below:

| gene name | gene ID | alternative name |
|---|---|---|
| CFTR | 1080 | |
| HPS1 | 3257 | |
| HPS2 | 7031 | TFF1 |
| HPS4 | 89781 | |
| TERT | 7015 | |
| TERC | 7012 | |
| DKC1 | 1736 | |
| SFTPB | 6439 | |
| SFTPC | 6440 | |
| SFTPA1 | 653509 | |
| SFTPA2 | 729238 | |
| MUC5B | 727897 | |
| SHH | 6469 | |
| PTCH1 | 5727 | |
| SMO | 6608 | |
| ABCA3 | 21 | |

In addition, cystic fibrosis is associated with gene mutations in the cystic fibrosis transmembrane conductance regulator (CFTR) and polymorphisms associated sodium channel epithelial 1 alpha (SCNN1A) genes, and such mutations/polymorphisms are highly variable. With reference to the expressed proteins of such genes, the mutations include F508 in the a CFTR protein, G551 in a CFTR protein, G542 in a CFTR protein, N1303 in a CFTR protein, R117 in a CFTR protein, W1282 in a CFTR protein, R553 in a CFTR protein, c.3849+10 kb in a CFTR protein, c.2657+5 in a CFTR protein, c.3140-26 in a CFTR protein, and V114 in a SCNN1A protein. In addition, the publication entitled *Differentiation of Human Pluripotent Stem Cells into Functional Lung Alveolar Epithelial Cells* by Anjali Jacob, et al., Cell Stem Cell 21, 1-17, Oct. 5, 2017 uses such Crispr/cas system to correct the homozygous surfactant mutation (SFTPB121ins2) to restore surfactant processing in alveolar epithelial type 2 cells. Another publication entitled *Efficient Derivation of Functional Human Airway Epithelium from Pluripotent Stem Cells via Temporal Regulation of Wnt Signaling* by Katherine B. McCauley, et al., 2017, Cell Stem Cell 20, 844-857 uses CRISPR to correct a defect in forskolin-induced swelling that is rescued by gene editing to correct the disease mutation associated with a compound heterozygous CFTR genotype DF508/DF508.

Cells harboring mutated gene including, but not limited to, those described above can be subjected to a CRISPR/Cas system according to techniques known in the art (see, e.g., US Patent Pub. 20170022507) and described herein. Typically, the cells are subjected to the CRISPR/Cas induced genetic correction at a stage of growth and expansion such at a pluripotent stage. These cells would then be developed into LBOs as taught herein and observed for changes in phenotype and/or biomarker expression.

Overview

Central Role of Type II Alveolar Epithelial Cells in IPF and Familial PF.

Pulmonary fibrosis is the formation or development of excess fibrous connective tissue (fibrosis) in the lungs, also described as "scarring of the lung." Pulmonary fibrosis may be a secondary effect of other diseases. Most of these are classified as interstitial lung diseases. Examples include autoimmune disorders, viral infections or other microscopic injuries to the lung. However, pulmonary fibrosis can also appear without any known cause (termed "idiopathic"), and differs from other forms of fibrosis in that it is not responsive to any immune suppressive treatment.

Idiopathic pulmonary fibrosis (IPF) is an intractable interstitial lung disease of increasing frequency with a median survival of 3 to 4 years, characterized by fibroblastic foci and remodeling and obliteration of alveoli.[1, 2] The only definitive treatment is lung transplantation, an intervention hampered by low availability of donor organs, and severe surgical, medical and immunological complications.[3]

Role of ATII Cells in Hermansky-Pudlak Syndrome (HPS)

The notion that defects in ATII cells underlie IPF is further supported by the fact that a subset of patients with Hermansky-Pudlak Syndrome (HPS) shows a high incidence of IPF, also called HPS-associated interstitial pneumonia (HPSIP).[56] HPS is caused by abnormal biogenesis and trafficking of lysosome-related organelles (LROs) and characterized by pigmentation abnormalities and bleeding diathesis associated with dysfunction of melanosomes and platelet delta granules, respectively, which are both LROs. The lamellar bodies (LBs) of ATII cells, where surfactant is stored, secreted and recycled, are also LROs.[21, 22] The mutations causing HPS affect four distinct protein complexes: biogenesis of lysosome-related organelle complex (BLOC)1 (HPS7,8,9), BLOC2 (HPS3,5,6), BLOC3 (HPS1, 4) and AP3 (HPS2). While the function of these complexes is unclear, they are all involved in protein trafficking and biogenesis of LROs.[21, 22] Of the nine known mutations, three (HPS1 and HPS4, affecting BLOC3, and HPS2, disabling AP3) are associated with IPF after the 3$^{rd}$ decade of life that is clinically, prognostically, radiologically and histologically very similar to IPF.$_{21, 22}$ In HPS1, the incidence of IPF is >80%, making this the most penetrant IPF mutation.$_{21}$ Several mouse strains with spontaneous mutations phenocopy the pigmentation defects and platelet abnormalities of the various subgroups of human HPS, and were instrumental in identifying the culprit genes in humans.$_{57-62}$ Although none display spontaneous IPF, susceptibility to bleomycin-induced fibrosis segregates with incidence of IPF in human HPS subgroups.$_{19}$ In HPS2mt mice, transgenic correction in ATII cells rescued fibrosis susceptibility, demonstrating the critical role of ATII dysfunction in pathogenesis.$_{19}$ PF occurs in older ep/pe mice, which have mutations in HPS1 and HPS2, thus providing perhaps the best mouse model of IPF.$_{18, 63}$ Chediak-Higashi syndrome (CHS) is also a disease of LROs, caused by mutation in LYST in patients and in beige (be) mice,$_{64}$ where innate immunodeficiency and neurodegeneration are prime manifestations.$_4$ LYST is involved in vesicle fusion or fission, but its exact function is unknown.$_{65}$ In beige mice and in CHS patients, LBs are enlarged,$_{4, 19, 33, 34}$ similar to patients who died from HPSIP$_{66}$ and the ep/pe mouse, but CHS is not associated with PF.$^{18, 58}$ These findings indicate that not every ATII injury precipitates fibrosis.

Further supporting a role of ATII cells are increased apoptosis and lysosomal and ER stress observed in ATII cells of ep/pe mice, findings that were confirmed in a limited set of human HSPIP samples.$^{18}$ Similar types of stress have been observed in ATII cells in sporadic IPF, including unfolded protein response in the endoplasmic reticulum (UPRER, also associated with SFTPC mutation),$_{4, 5, 67}$ low autophagy,$_{6, 8, 9, 68}$ mitochondrial dysfunction,$_7$ and apoptosis. The role of ATII cells in IPF is most likely linked to their most specific function: production, secretion and recycling of surfactant. The lysosomal infrastructure is essential for cellular quality control mechanisms, including autophagy and mitophagy, in response to stress.$_{35-38}$ Isolation and maintenance of human ATII cells is challenging however. Importantly, features of ATII cells isolated from patients after diagnosis may not be informative for disease predisposition, as many observed changes may be secondary. Furthermore, it is believed that disease initiation occurs many years prior to clinical symptoms.$_{1, 2}$ ATII cells generated by directed differentiation of human pluripotent stem cells (hPSCs) will facilitate discovery of functional and transcriptomic commonalities induced in ATII cells by injury or mutations that lead to fibrosis. Derived from the inner cell mass of the blastocyst of mammals, embryonic stem cells (ESCs) can be maintained in a pluripotent state in vitro and give rise to every cell type in the organism.$_{80}$ Induced pluripotent stem cells (iPSCs) are generated by reprogramming of somatic cells, through transient expression of OCT4, KLF4, MYC and SOX2, to a pluripotent state similar or identical to ESCs.$_{80-89}$ CRIPSR/Ca9-mediated genome editing now allows engineering of desired mutations in hPSCs.$_{90-94}$ hPSC-derived ATII cells are in a pre-disease state, thus allowing the detection of pre-existing abnormalities.

There are no published studies on hPSC-based models for IPF. Mouse models have not been able to fundamentally elucidate pathogenesis of this highly prevalent and devastating disease. As the results presented here show, several technically and conceptually innovative and unique approaches have been combined, including the generation of distal lung cells and mesenchyme from hPSCs, the genome modification of hESCs to introduce mutations that are associated with IPF, and the use of mutations that affect ATII cells but are not associated with IPF as controls to search for functional or expression characteristics shared in cells with IPF-prone mutations to gain desperately needed insight into the pathogenesis of IPF.

Figure 11:
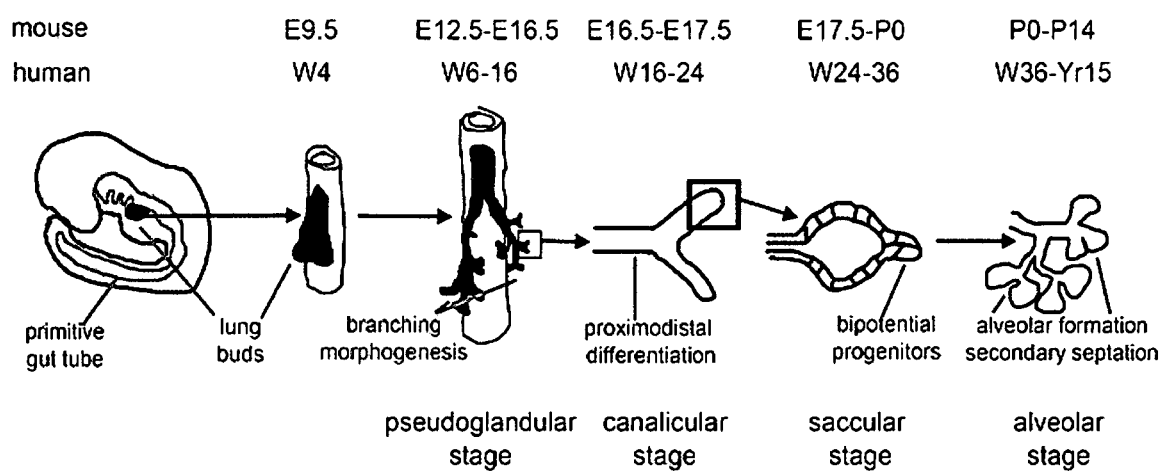
FIG. 11. Lung development. The respiratory system originates from buds that arise on the ventral aspect of the anterior foregut endoderm (AFE). These develop through a stereotyped branching process into proximal airways and distal alveolar progenitors (pseudoglandular stage). During the canalicular stage, cell cycle activity decreases, and specialization of the airway epithelium occurs in the stalks, with the emergence of basal, goblet, club, ciliated, and other cell types (FIG. 11). This stage is followed by the saccular stage, where the canaliculi widen into sacculations that will give rise to primitive alveoli.95-97 Expansion of alveolar number by further differentiation of immature saccules, alveolar maturation and secondary septation continue predominantly postnatally.98

The respiratory system originates from buds that arise on the ventral aspect of the anterior foregut endoderm (AFE) and develop through a stereotyped branching process into proximal airways and distal alveolar progenitors (pseudoglandular stage). During the canalicular stage, cell cycle activity decreases, and specialization of the airway epithelium occurs in the stalks, with the emergence of basal, goblet, club, ciliated, and other cell types. This stage is followed by the saccular stage, where the canaliculi widen into distal sacculations that will give rise to primitive alveoli$^{6,7}$. (FIG. 11)

Figure 6A:
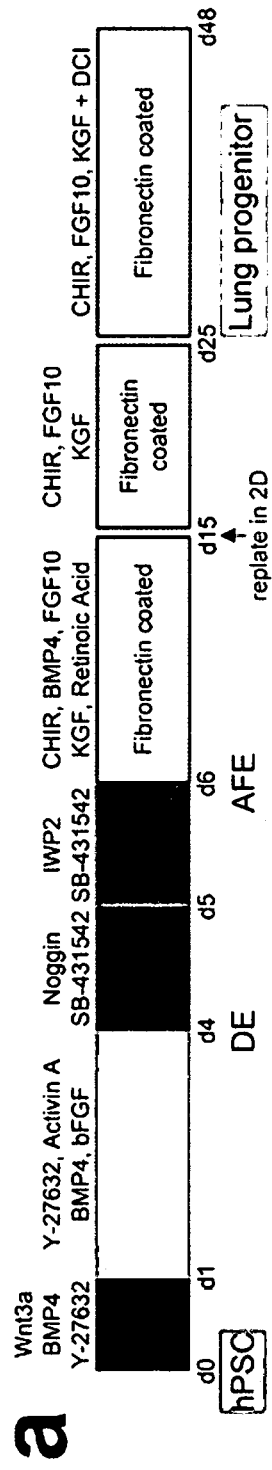
FIGS. 6A-6E: Characterization of lung bud organoids.

We previously reported a strategy to differentiate hPSCs (embryonic stem cells (ESCs) and reprogrammed induced pluripotent stem cells (iPSCs)) in 2D through sequential developmental steps from definitive endoderm (DE) to AFE, lung field progenitors, and, finally, lung and airway epithelial cells. These developments are disclosed in U.S. Pat. Nos. US20160168535 and US20150247124. (FIG. 6A)$^{10-12}$ As mentioned above, embodiments of new methods have been developed for making LBOs that contain pulmonary endoderm and mesoderm compatible with pulmonary mesenchyme, and undergo branching morphogenesis and distal lung development in 3D culture. Embodiments of new methods are also described to make LBO with the most advanced morphogenesis by xenotransplantation of LBO such as under the kidney capsule of immune deficient mice. LBOs that are xenotransplanted at least partially recapitulate human lung development and therefore can be used to model and assess factors that affect lung development including whether an IPF-like phenotype arises in vivo. In other embodiments, BLBOs-3D and BLBOs-xeno are made from RUES2-HPS1$^{DEL}$ cells with engineered mutations in HPS1 using CRISPR/Cas9 in hESCsh that predisposes with high penetrance to IPF.$_{22, 44}$; these mutant LBOs allowed recapitulation of fibrosis in vitro and are expected to do the same in vivo via xenotransplantation. Genome-edited ESCs avoid issues of incomplete reprogramming and background genetic variation associated with iPSCs.$_{45}$ Most efforts at disease modeling use iPS cells.$_{45, 134, 135}$ During iPS generation, the epigenetic signature of mature cells is erased, and pluripotency networks and epigenetic marks are established that maintain the cells in a pluripotent state corresponding to that of ESCs.$_{45, 136, 137}$ Although iPSCs are very close, if not identical to ESCs, incomplete reprogramming and the persistence of epigenetic memory, which may favor the differentiation of iPSCs into the cell type they were originally derived from, have been described, though the issue is debated.$_{45, 138, 139}$ Furthermore, genetic background is the most important contributing factor to variation among iPS lines,$_{45, 140}$ necessitating multiple clones from a sufficient number of patients to achieve statistical power. The availability of CRISPR/Cas9-mediated genome editing technology now allows introduction of patient mutations in ESCs.$_{91-93}$ This eliminates genetic background variation to a large extent, as well as bias and variability caused by incomplete reprogramming and epigenetic memory, if these would exist. The use of iPSCs is preferred in sporadic IPF however, where familial predisposition may be present but where associated mutations have not been identified, or where multiple loci may be involved.

Although one group reported generation of human lung organoids,[8,9] these small structures contained cells expressing markers of lung and airway[8] cells and had some airway potential after subcutaneous xenografting in mice[9], they do not satisfy the aforementioned criteria for organoids, as neither features of lung development, notably branching morphogenesis and proximodistal specification, nor function were observed. Thus, until now there have been no lung organoid cultures that could be used to model either normal or abnormal, such as fibrotic, lung.

Results

A. 3D Lung Development in the Presence of Mesoderm

As IPF is a fibrotic disease with a major mesenchymal component, we aimed for a model where mesenchyme was present. LBO were generated from human pluripotent stem cells in culture. The strategy described below can be applied to ES cells (for example RUES2 cells) or to iPS cells, generated, for example, using Sendai virus or modified mRNA from both healthy human dermal fibroblasts[7, 9] (passage 16-25) and IRF7-deficient C12 hiPSC lines.[28] The cells were maintained on mouse embryonic fibroblasts (MEFs) plated at 15,000-18,000 cells/cm$^2$.

Figure 6B:
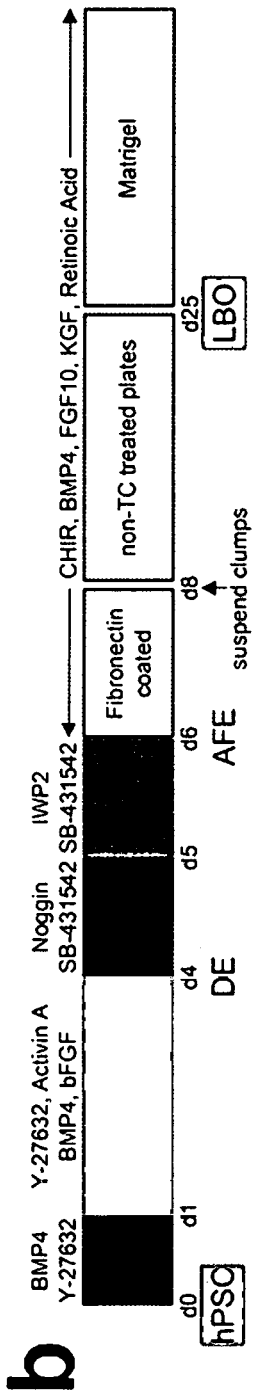

In the results described in FIGS. 1-4, experiments were done with normal RUES2 embryonic stem cells (ESCs), but similar data are obtained with iPSCs. Endoderm was induced by depleting mouse embryonic fibroblasts (mfe) and then culturing the hPSC in in embryoid body/primitive streak formation medium followed by a switch to endoderm induction medium. Anterior foregut endoderm was induced as previous described[9], and then the AFE was treated with ventralization media (Branching media) for 48 h and three-dimensional clump formation was observed. The clumps were then suspended by gently pipetting around the wells. Early during induction of a ventral lung fate from anterior foregut epithelium (AFE) in the presence of Ventralization media/Branching media, adherent structures formed that detached easily and expanded in suspension culture as clumps of cells (FIG. 1A-1B) in the presence of BMP4, FGF10, FGF7, retinoic acid (RA) and the GSK3β antagonist, CHIR99201 (FIG. 6B), which are factors shown previously to be required for lung development[6,7]. From 7.5×10$^5$ definitive endoderm (DE) cells 2490+129 clumps were generated (n=3; RUES2 ESCs). The suspended clump of AFE, called lung bud organoids (LBOs) hereafter, were maintained in non-tissue culture treated multiple-well plates submerged in Branching media and were fed every other day until d20-d25 at which time they were embedded in 100% MATRIGEL® or implanted under the kidney capsule of NOD.Cg-Prkdc$^{scid}$.Il2rg$^{tm1Wjl}$/SzJ (NSG) mice.

Figure 1C:
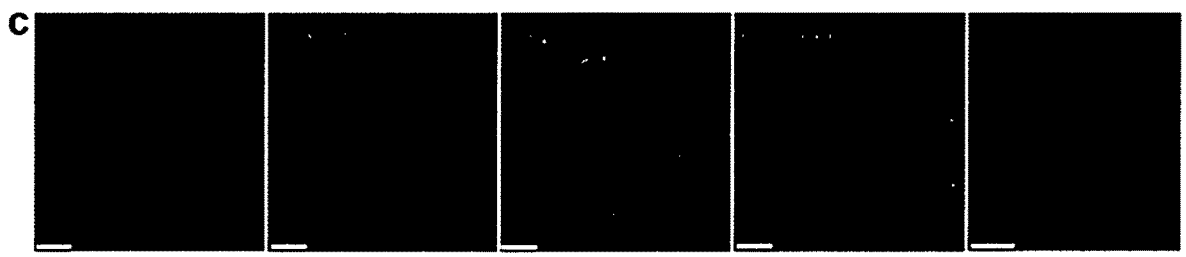
Figure 1D:
Figure 1E:
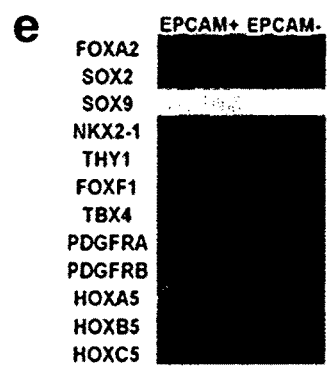
Figure 6C:
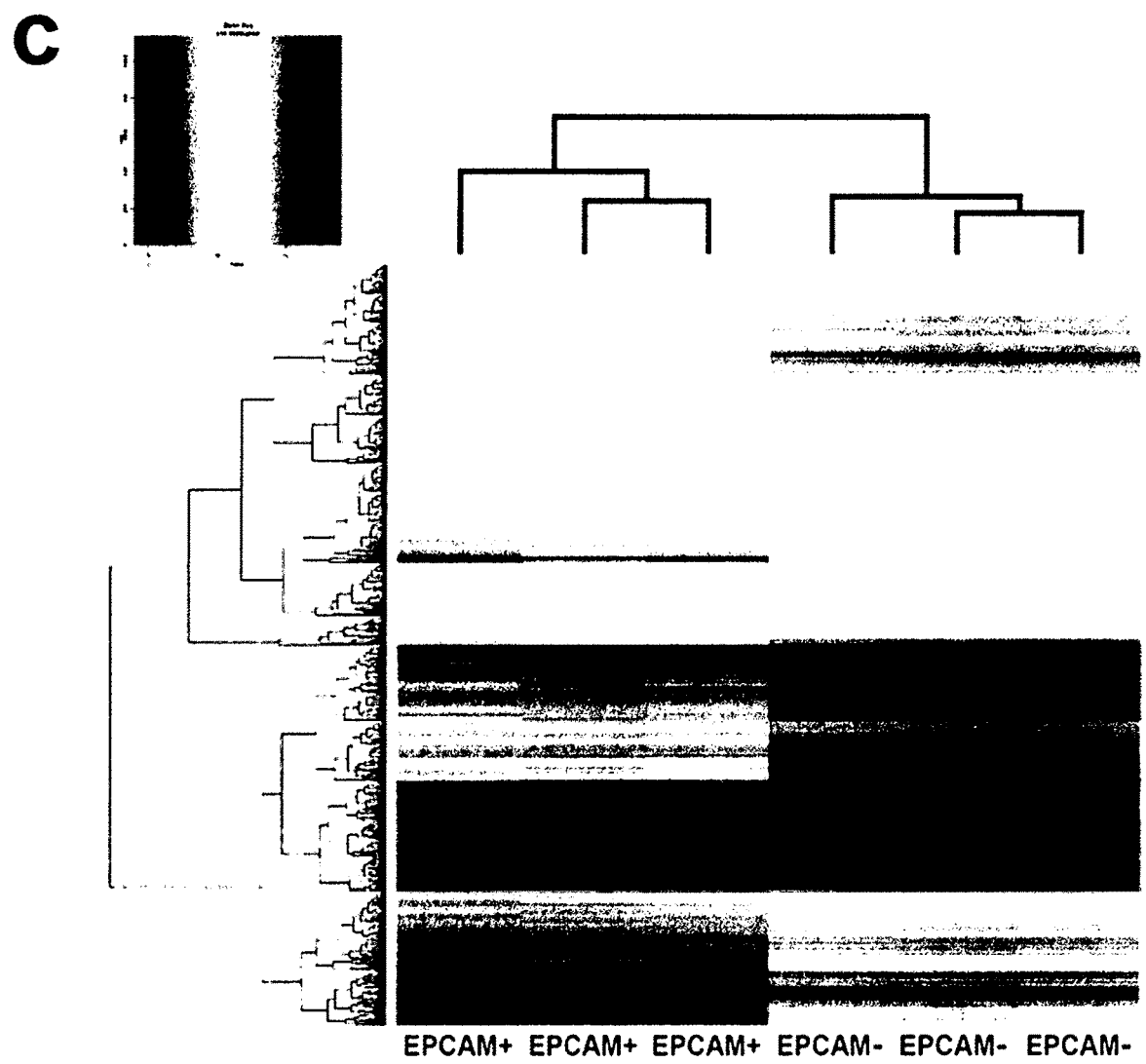
Figure 6D:
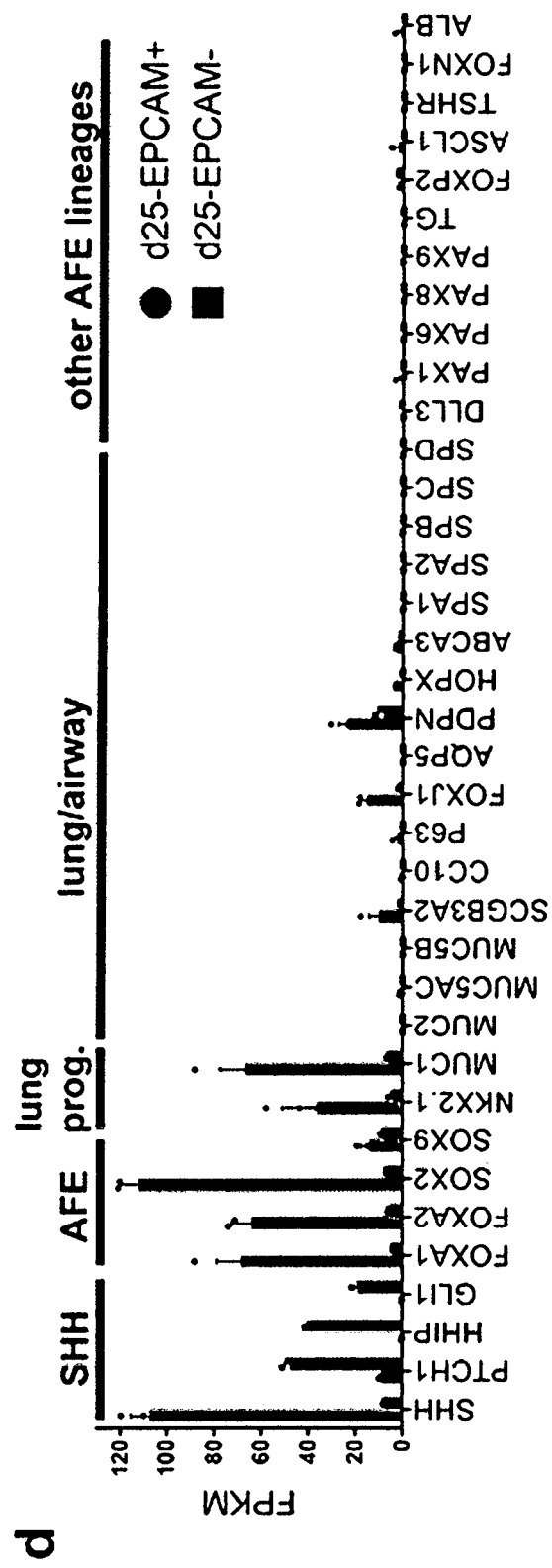
Figure 6E:
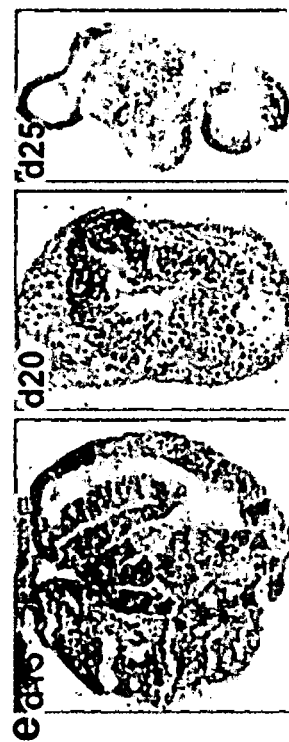

During the suspension culture phase of the LBOs, the structures formed folding sheets of EPCAM$^+$KRT8$^+$ECAD$^+$ FOXA1/2$^+$ AFE, cells (FOXA2: 89.07%±3.36%, EPCAM+: 92.08%±1.88%, n=3; RUES2 ESCs) (FIG. 1C). By d25 51.26+4.37% (n=3; RUES2 ESCs) of the cells expressed the lung marker NKX2.1±(FIG. 1C). Except for the epithelial progenitor marker, p63 (18.59%±1.49%, n=3; RUES2 ESCs, FIG. 1C), markers of mature lung and airway cells were absent (noECRt shown). The cells were surrounded by mesodermal PDGFRA$^+$ECAD$^-$ cells (FIG. 1D). RNAseq (FIG. 6C) confirmed strong enrichment of endoderm/lung genes (FOXA2, SOX2, NKX2.1) in EPCAM$^+$ cells (FIG. 1E). EPCAM$^-$ cells expressed mesodermal genes (FIG. 1e), some of which, such as TBX4 and HOX5 paralogs, are expressed in pulmonary mesoderm[13,14]. Genes expressed in mature lung and airway and in other AFE-derived lineages were nearly undetectable in the EPCAM fraction (FIG. 6D). Sonic Hedgehog (SHH) was expressed in endodermal cells, and its transcriptional targets[15], PTCH1, GLI1 and HHIP in mesoderm (FIG. 6D). In situ hybridization confirmed SHH expression in the endodermal fraction at d15. At d25, SHH was expressed most strongly in the tips of budding epithelial structures (FIG. 6E). These findings are consistent with early developing mouse lung, where SHH is expressed throughout the pulmonary endoderm initially, but becomes progressively limited to the branch tips during branching morphogenesis[15-17]. Because they contain multiple cell types that are spatially organized similar to developing lung buds in vivo, we call these structures lung bud organoids (LBOs).

B. In Vivo Potential of Human Lung Bud Organoids after Xenotransplantation.

Figure 2A:
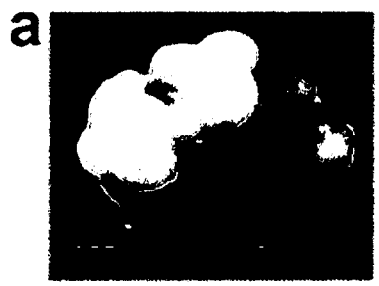
FIGS. 2A-2G. In vivo potential of LBOs.
Figure 2B:
Figure 2C:
Figure 2D:
Figure 2E:
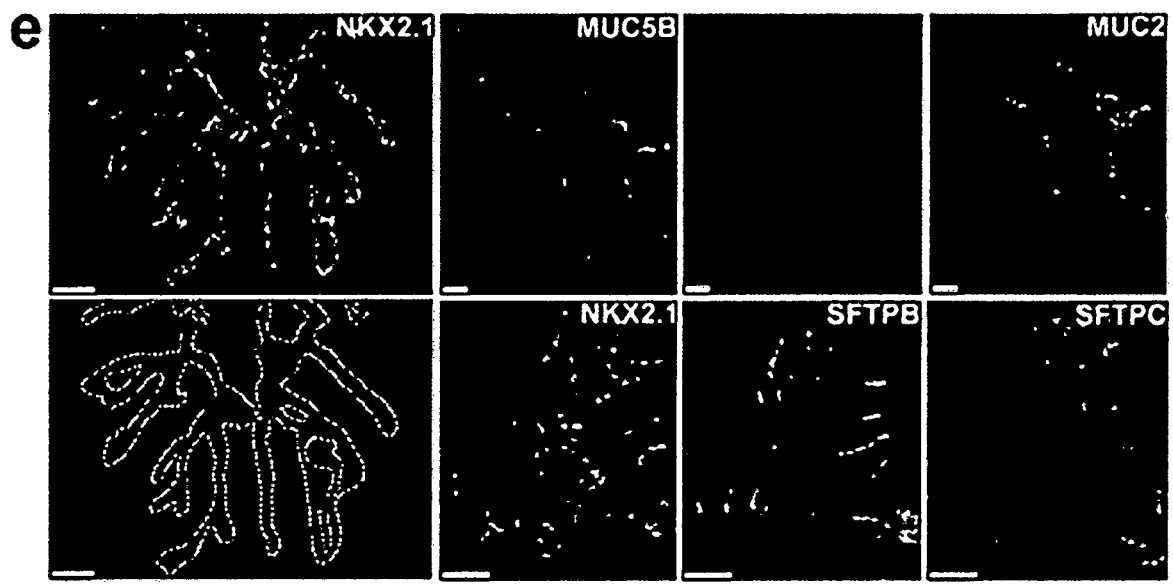
Figure 2F:
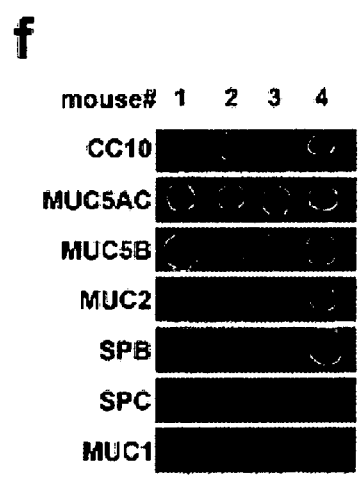
Figure 2G:
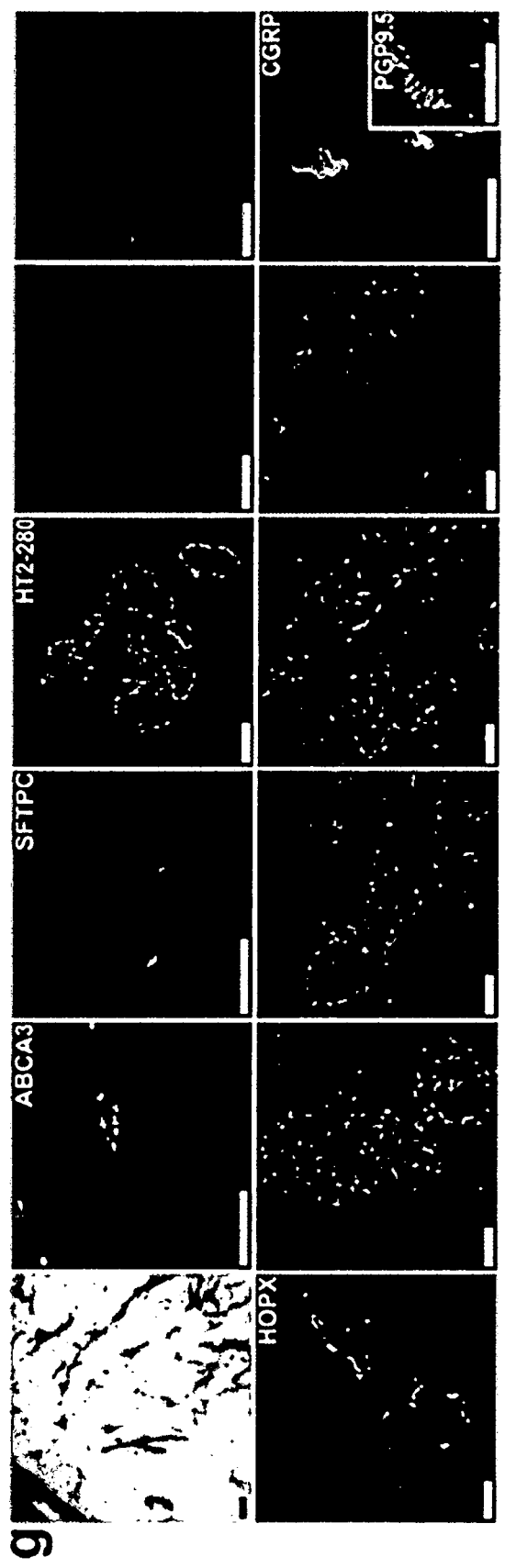
Figure 7E:

At about day 20-25, approximately one million d20-d25 LBO cells were mixed with 5 µl MATRIGEL® prior to surgery and implanted under the kidney of NOD.Cg-Prkdc$_{scid}$.Il2rg$^{tm1Wjl}$/SzJ (NSG) mice. When transplanted under the kidney capsule of immunodeficient NSG mice, LBO-xeno from human RUE2 cells produced growths (FIG. 2A) with abundant mesenchymal tissue, including smooth muscle, looser connective tissue and rare cartilage. The LBO-xeno contained tubular structures surrounded by mesenchymal tissue after about 1.5 months (FIG. 2B). The tubes were uniformly lined by a FOXA2$^+$NKX2.1$^+$SOX2$^+$ epithelium containing MUC5AC$^+$ (goblet) cells with p63$^+$ cells in the basal layer (FIG. 2C), which is compatible with airway epithelium. All cells were human (FIG. 7a), except for endothelial cells, which were of mouse origin (FIG. 7B). After 5 months, branching structures (FIG. 2D, FIG. 7C) surrounded by SMA mesodermal cells arose (FIG. 7C). All epithelial cells were NKX2.1$^+$ while SOX2, a proximal marker later in lung development[18,19], was excluded from the branch tips, which expressed SFTPB and SFTPC, markers of surfactant-producing type II alveolar epithelial (ATII) cells (FIG. 2E)[20]. The stalks and central tubules expressed the proximal (airway) markers FOXJ1 (ciliated cells), CC10 (club cells) and mucins (goblet cells) (FIG. 2E). Hematoxylin-eosin staining showed abundant multiciliated cells (FIG. 2D), while live imaging documented beating cilia. Furthermore, submucosal glands were observed near the larger tubular structures (FIG. 7E). Overall, morphology and expression pattern within the growths are consistent with proximodistal specification during lung branching morphogenesis[6,7]. The fluid in the tubular structures contained all tested secretory products of lung and airway but was negative for the cell surface mucin[21], MUC1, indicating detection of secreted proteins and not proteins associated with sloughed cells, and providing evidence for function (FIG. 2F). After 7 months, dome-shaped groups of CGRP$^+$ PGP9.5$^+$ cells, compatible with neuroepithelial bodies[22], were present in the airway-like structures (FIG. 2G). Furthermore, areas of the growths developed into a network of thin cell layers (FIG. 2G) containing cells expressing ATII cells markers (SFTPC, ABCA3, HT2-280)[23] and cells bearing type I alveolar epithelial cell (ATI) markers (HT1-56, HOPX, PDPN, CAV1, SCNN1A, AKAP5, CLIC5)[20], although other markers for mature ATI cells (RAGE, AQP5)[20] were not detected (FIG. 2G). An alveolar capillary network and bronchoalveolar ducts were not observed, however. We conclude that, although full phenotypic and architectural alveolar maturation was not achieved, possibly at least in part because of the ectopic location, LBOs recapitulate many essential features of lung development, including branching morphogenesis and proximodistal specification, after xenotransplantation.

Figure 3A:
FIGS. 3A-3B. LBO differentiation in MATRIGEL® at d70.
Figure 3B:
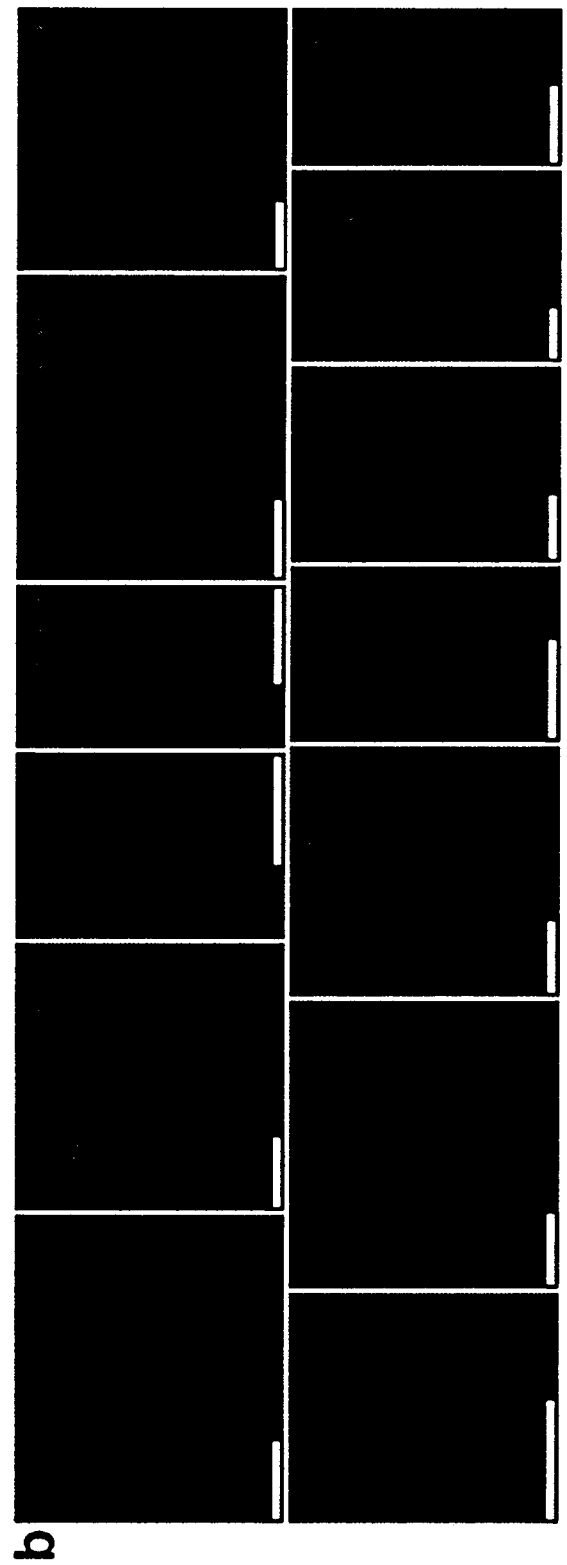
Figure 8A:
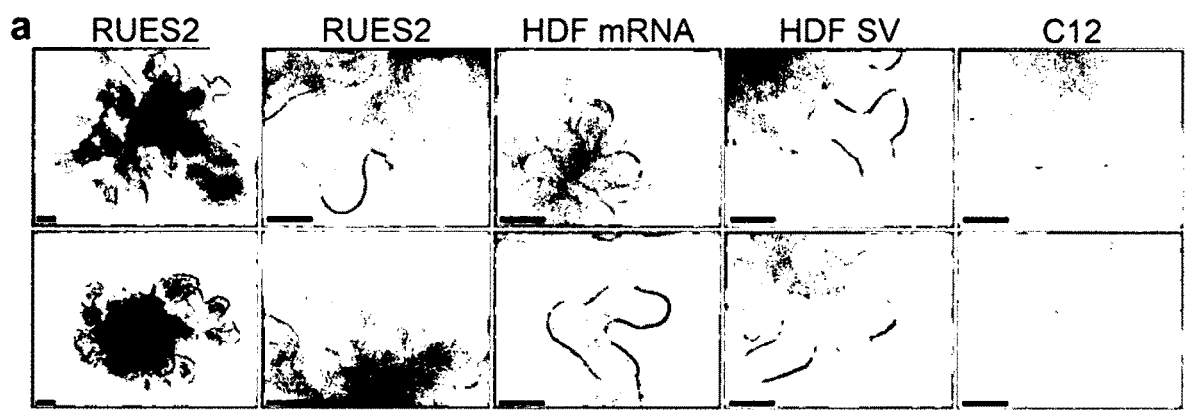
FIGS. 8A-8E. Branching in iPS and ES LBOs and mesoderm requirement for branching.
Figure 8B:
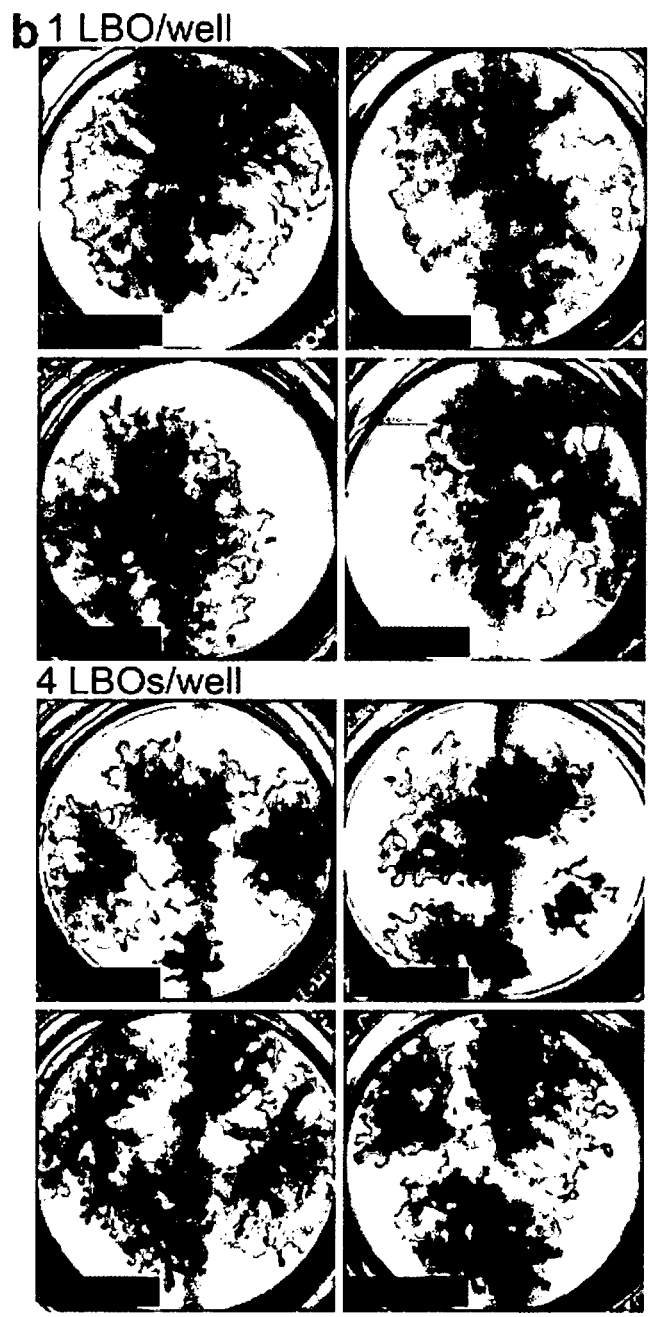

C. Long-Term BLBO-3D Development In Vitro and ATII Function: LBOs in 3D Matrix are Capable of Generating Branching Colonies, and Mesenchymal Cells are not Required for Branching in these Culture Conditions After embedding d25 LBOs from RUES2 in MATRIGEL® in the presence of CHIR99021, FGF10, FGF7, BMP4 and RA (see FIG. 6B), >95% yielded rapidly expanding branching structures (FIG. 3A for RUES2 and See also FIG. 8A for iPSCs, including C12, a line from a patient with mutations IRF7 that causes acute respiratory distress syndrome after influenza infection)[24]. The RUES2 cells express markers of pulmonary endoderm (FOXA2$^+$: 95.17%±1.54%, NKX2.1$^+$: 74.97%±4.37%, EPCAM$^+$: 96.83%±0.62%, SOX9$^+$: 92.42%±3.81% n=3 at d70; RUES2 ESCs) (FIG. 3B). Uniform luminal expression of MUC1 demonstrates polarization (FIG. 3B). Cells expressing the ATII markers SFTPC, SFTPB and ABCA3 were present in all structures (FIG. 3B). Airway goblet cells (MUCSB or MUC5AC) were rare while other airway cells (club cells (SCGB3A2), ciliated cells (FOXJ1) and basal cells (KRT5 and P63)) were not detected (not shown). While singly plated RUES2 LBOs branched randomly in every direction and filled a 6.4 mm well within 90 days, they formed branching trees that only occupied a section of the well when plated together in close proximity (FIG. 8B). These findings show that branching architecture of normal RUES2 cells can be manipulated in vitro, and that repulsive interactions between branching structures may play a role in determining their architecture.

Figure 8C:
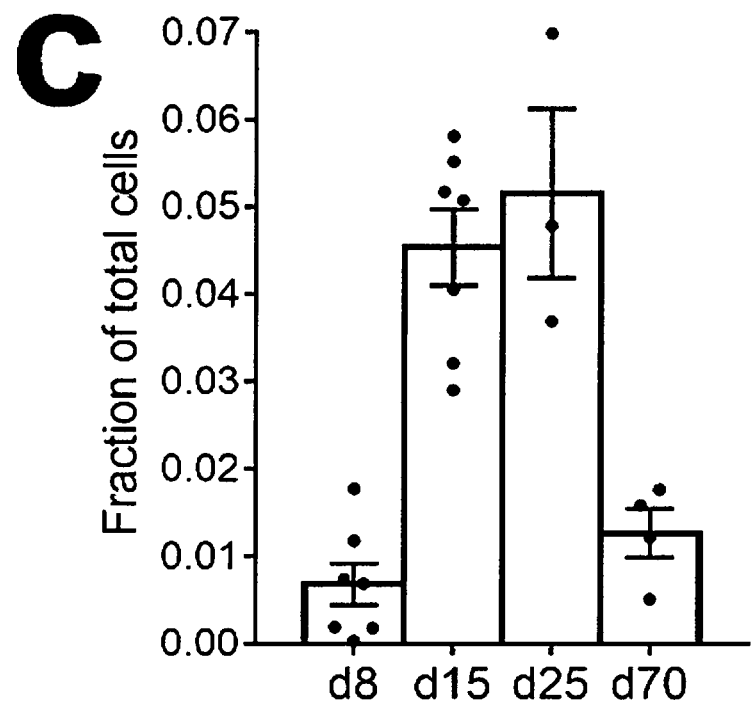
Figure 8D:
Figure 8E:
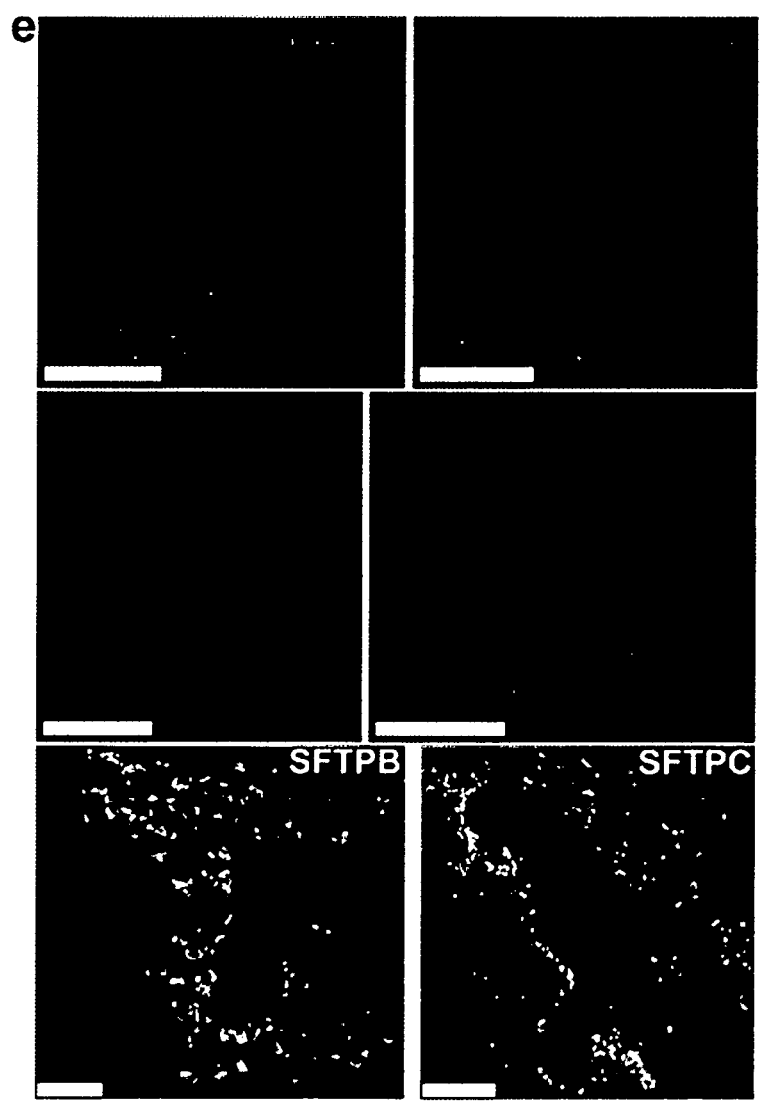

Mesenchymal cells in the RUES2 expressing VIMENTIN and CD90 were present surrounding the LBO-3D structures (FIG. 3B). Their proportion, as determined by flow cytometry for EPCAM$^-$ cells, declined during MATRIGEL® culture to less than 2% of the total population however (FIG. 8C). EPCAM$^+$, but not EPCAM$^-$ cells, purified from d25 LBOs yielded branching colonies after plating in MATRIGEL®, albeit with low cloning efficiency (0.30+0.0316%) (FIG. 8D). These branching colonies displayed a similar pattern of marker expression as MATRIGEL® colonies generated from intact LBOs (FIG. 8E). These findings indicate that rare progenitors in the LBOs are capable of generating branching colonies, and that mesenchymal cells are not required for branching in these culture conditions.

Figure 9A:
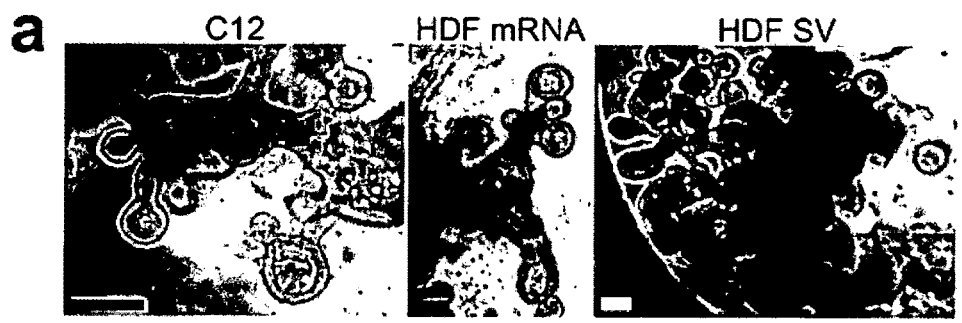
FIGS. 9A-9E. LBO maturation in MATRIGEL® at d170.
Figure 9B:
Figure 9C:
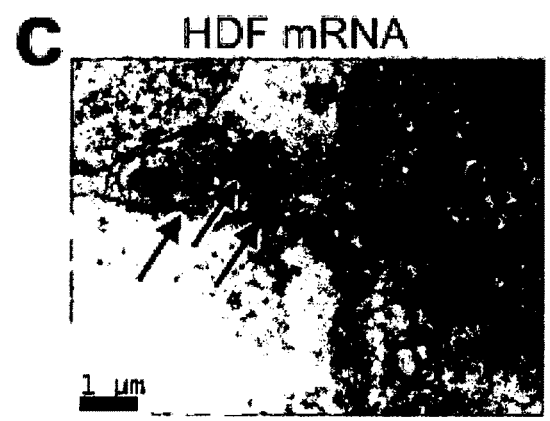

D. RUES2 LBOs In Vitro Recapitulate Human Lung Development Up to the Late Second Trimester of Human Gestation After >170 days of RUES2 LBO-3D culture, macroscopic tissue (FIG. 4A) consisting of branching tubules with dilated tips, reminiscent of saccules formed during the saccular stage of lung development, had developed (FIG. 4B, FIG. 9A), 84.86%+5.21% cells were NKX2.1$^+$, while most cells were SOX9$^+$ (76.75+6.89%) and a minority (23.78+5.21%) were SOX2$^+$ (FIG. 9B) (n=4, one ESC and three iPS lines). Most luminal cells expressed HT2-280, MUC1, SFTPB, SFTPC and ABCA3 (RUES2 FIG. 4C, iPSCs FIG. 9B), identifying these as ATII cells. Electron microscopy showed large numbers of lamellar bodies (LBs), the organelles where surfactant is stored[25] (FIG. 4D, FIG. 9C).

Figure 4E:
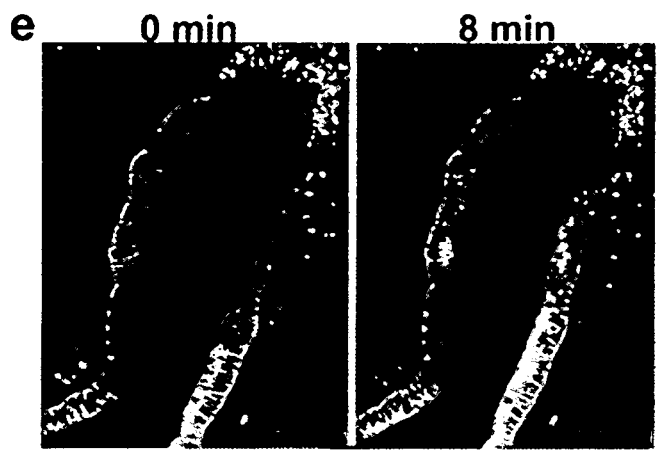
Figure 4F:
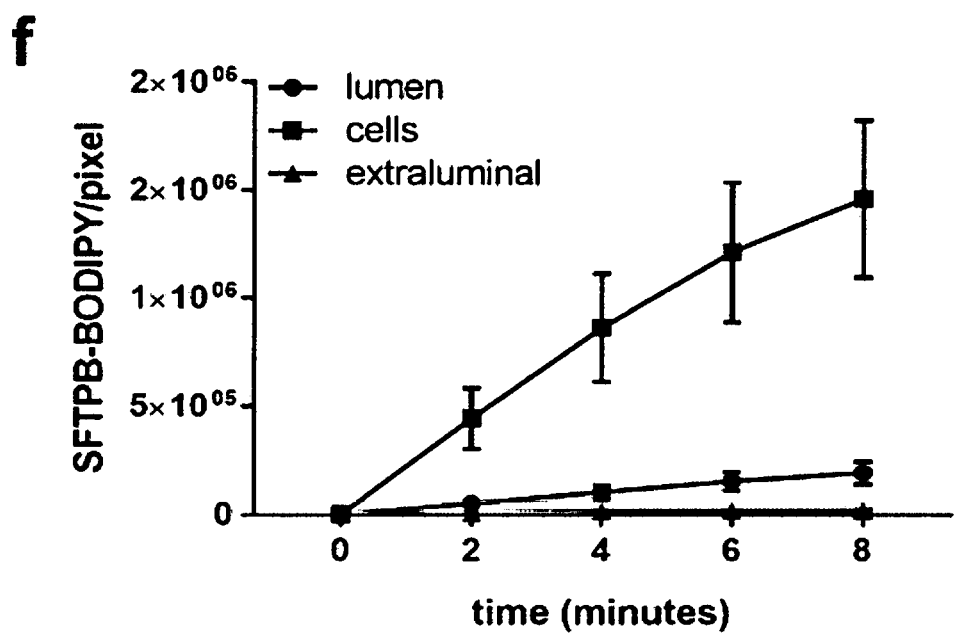

To examine ATII cell function, SFTPB covalently linked to the fluorescent lipid, BODIPY was added. Within minutes, SFTPB-BODIPY was taken up by the RUES2 LGO cells and secreted in the lumens (FIG. 4E, FIG. 4F). Although HOPX, a marker of ATI cells and of putative bipotential alveolar progenitors in the mouse,[20,26] was widely expressed (FIG. 9B), other ATI markers (AQP5, CLIC5, AKAP5, CAV1, AGER) were undetectable. SOX9, a marker for the distal tips that is downregulated as alveoli mature and becomes undetectable postnatally, was mostly expressed at the tips and outer edges of the branching structures in vitro, consistent with mouse development, where SOX9 is a distal lung marker[27-29] (FIG. 9B).

Figure 4G:
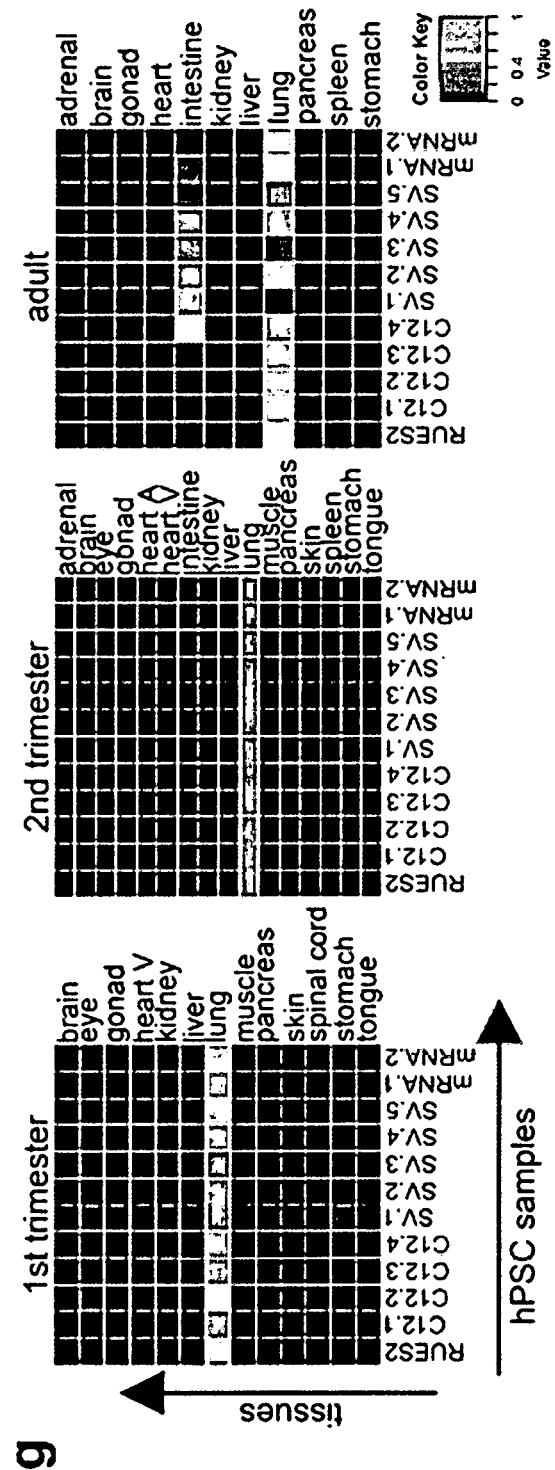
Figure 9D:
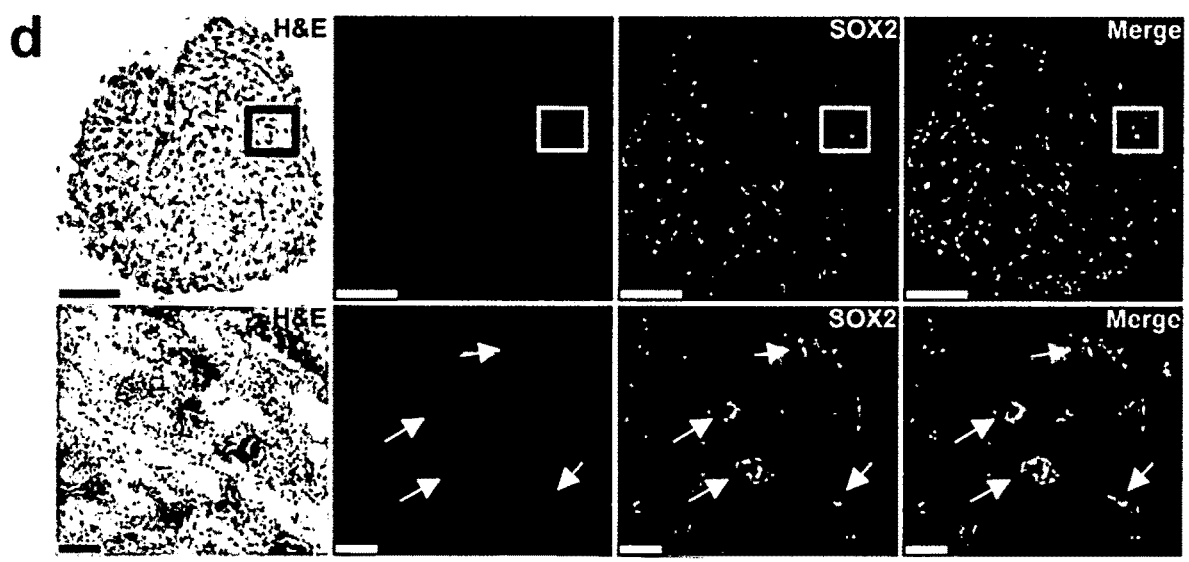
Figure 9E:
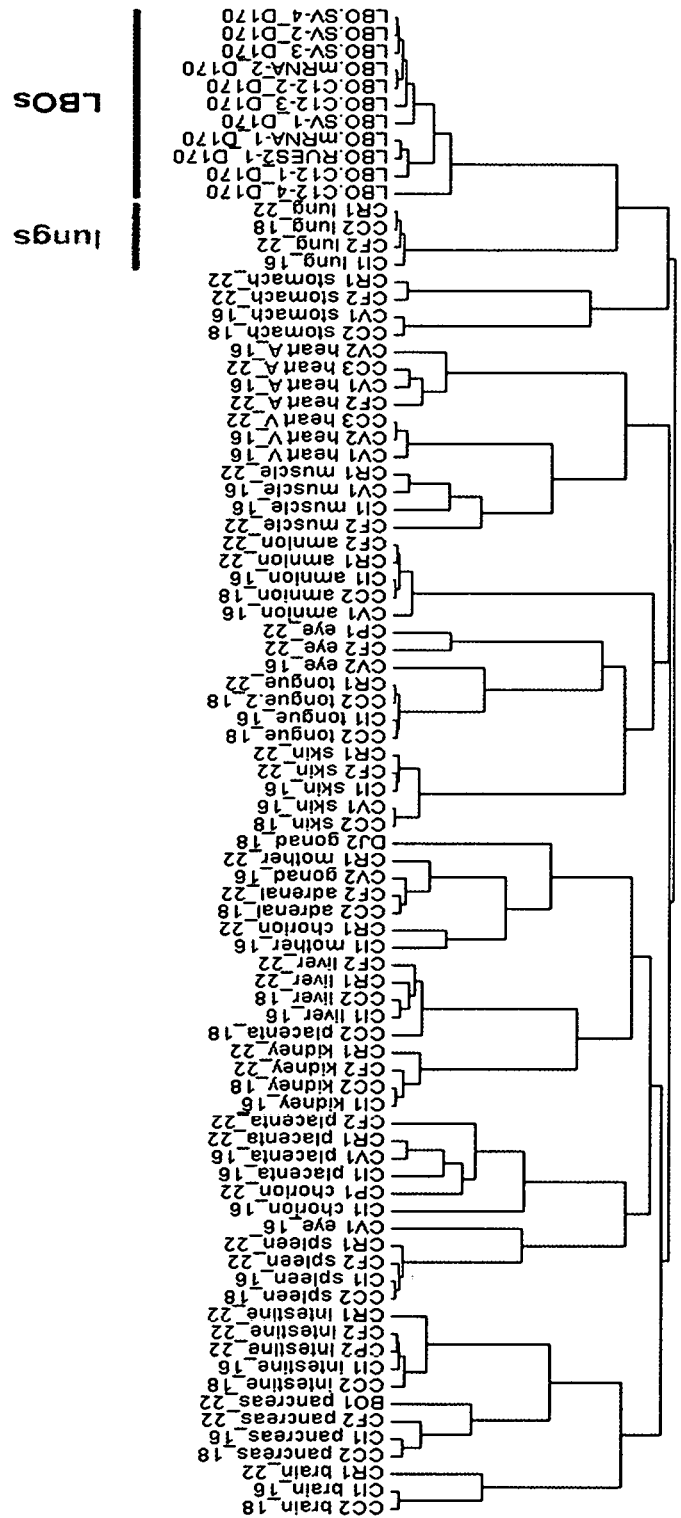

Expression of airway markers (MUC5AC, SCGB3A2) in the MATRIGEL® LBO-3D RUES2 colonies was confined to structures co-expressing SOX2 and SOX9 (FIG. 9B), and were therefore likely more proximal. While co-expression of SOX2 and SOX9 is unusual in the mouse[19], numerous larger SOX2$^+$SOX9$^+$ structures were identified in the human second trimester fetal distal lung (FIG. 9D), suggesting that LBO-3D recapitulate human lung development. The expression of SOX9, the formation of saccular structures expressing predominantly ATII markers and absence of mature ATI cells are consistent with the canalicular stage of lung development, which occurs at the end of gestation of mice, but during the late second trimester in humans. To further verify the developmental stage of d170 MATRIGEL® LBO-3D cultures, we performed RNAseq on 12 independent samples from RUES2 cells and from three iPSC lines. Cross-referencing with the KeyGenes database, which contains expression profiles of human organs during first and second trimesters of gestation and adulthood[30], showed the best match with second trimester fetal lung, without any match with other organs (FIG. 4G, FIG. 9E). Together, the structural, protein expression and transcriptomic data indicate that the d170 MATRIGEL® RUES2 LBO organoids reached the late second trimester of human gestation.

E. Potential Application of LBO-3D in Modeling Human Diseases

Figure 5A:
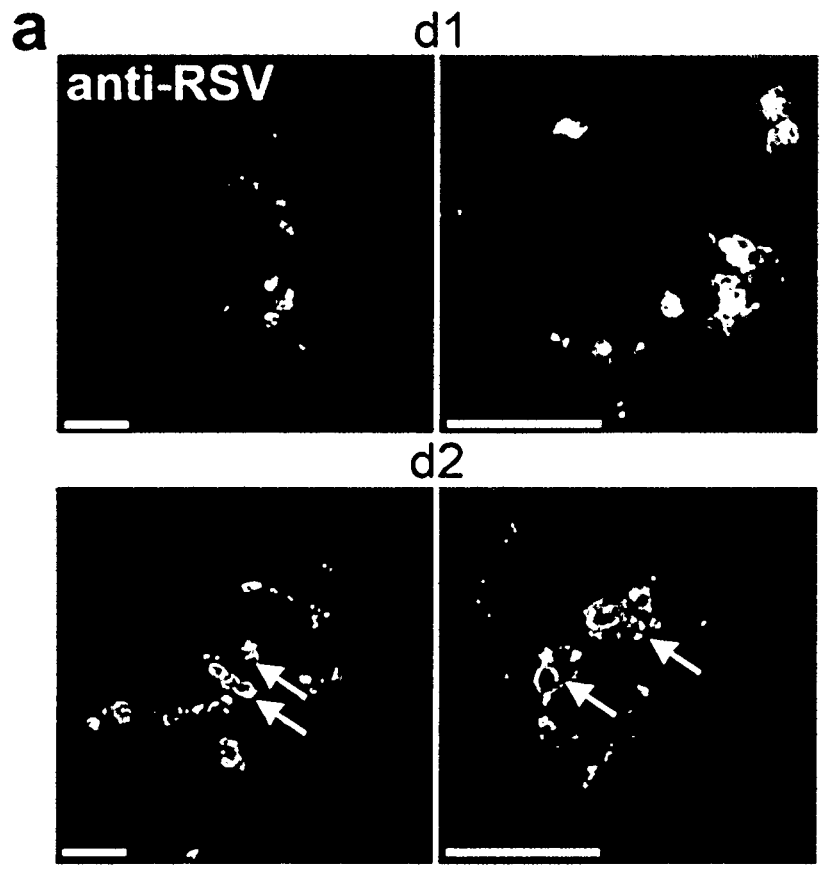
FIGS. 5A-5D. Potential application of LBOs in modeling human diseases.

1. LBO Model Reproduces the Morphological Features of RSV Infection in the Distal Lung We next explored whether select infectious and fibrotic lung disease could be recapitulated. We asked whether LBO-3D infected with respiratory syncytial virus (RSV) display features of human lung infection. RSV is a major cause of lower respiratory tract infection in infants, and causes bronchiolitis with obstruction of small airways[2,31]. There is no licensed vaccine or effective antiviral drug at this time, and immunity after infection is short-lived[32]. RSV tropism in humans includes ciliated cells and alveolar epithelial cells[2,3]. Previous studies in human airway epithelial cell lines showed that cells infected with RSV swell and detach from the epithelium[33], a finding consistent with obstruction of small airways by infected cells in archival pathology specimens and with the clinical syndrome of bronchiolitis[3]. At day 2 after infection of d170 MATRIGEL® LBO-3D cultures with RSV, confocal microscopy revealed shedding of swollen, infected cells into the lumen of the branching structures (FIG. 5A, arrows). No shedding was seen at day 1, despite evidence of viral infection. RSV infection in LBOs therefore recapitulates important features of infection in humans.

2. The RUES2-HPS1$^{DEL}$ LBO-Xeno Model Showed Accumulation of Mesenchymal Cells in HPS1-Mutant Cell Lines Made Using CRISPR-CAS9

RUES2 lines were transfected with CRIPSR/Cas9 constructs that had been screened in a neuroblastoma line for induction of appropriate mutations. Clones were picked and analyzed by PCR using primers spanning the CRISPR homology regions followed by plasmid cloning and sequencing to detect lines with the desired mutation or indel. In addition to classical approaches to verify deletion (PCR, sequencing), for HPS mutations absence of the involved complex was verified by WB (BLOC1-3 and AP3 complexes are ubiquitously expressed)$_{21, 60, 141}$ as it has been shown that each mutation destabilizes the entire complex to which the encoded protein belongs.[141, 142] The targeted sequences for mutation are provided in FIGS. 13-16.

F. RUES2 Cells (RUES2-HPS1$^{DEL}$) and Evidence of Fibrosis

Next, we attempted to model pulmonary fibrosis associated with some forms of Hermansky-Pudlak Syndrome (HPS)[5]. HPS is characterized by pigmentation and bleeding abnormalities caused by abnormal biogenesis and trafficking of lysosome-related organelles (LROs), which include platelet dense granules and melanosomes.[34] Some forms, in particular HPS1, are associated with early-onset and intractable pulmonary fibrosis (HPS interstitial pneumonia (Hermansky-Pudlak syndrome associated interstitial pneumonia or HPSIP)) that is clinically similar Idiopathic pulmonary fibrosis (IPF)[5], is characterized by fibrotic obliteration of alveoli and has a median survival of 3-4 years[35]. The fact that LBs of ATII cells are also LROs[34] potentially explains the association of IPF with some mutations causing HPS[5].

Figure 5B:
Figure 5C:
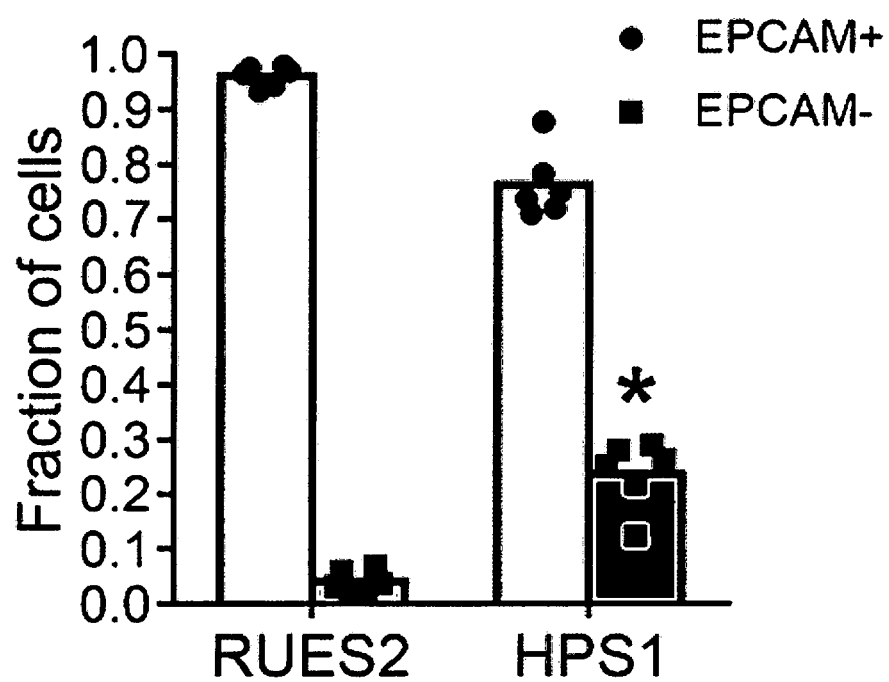
Figure 5D:
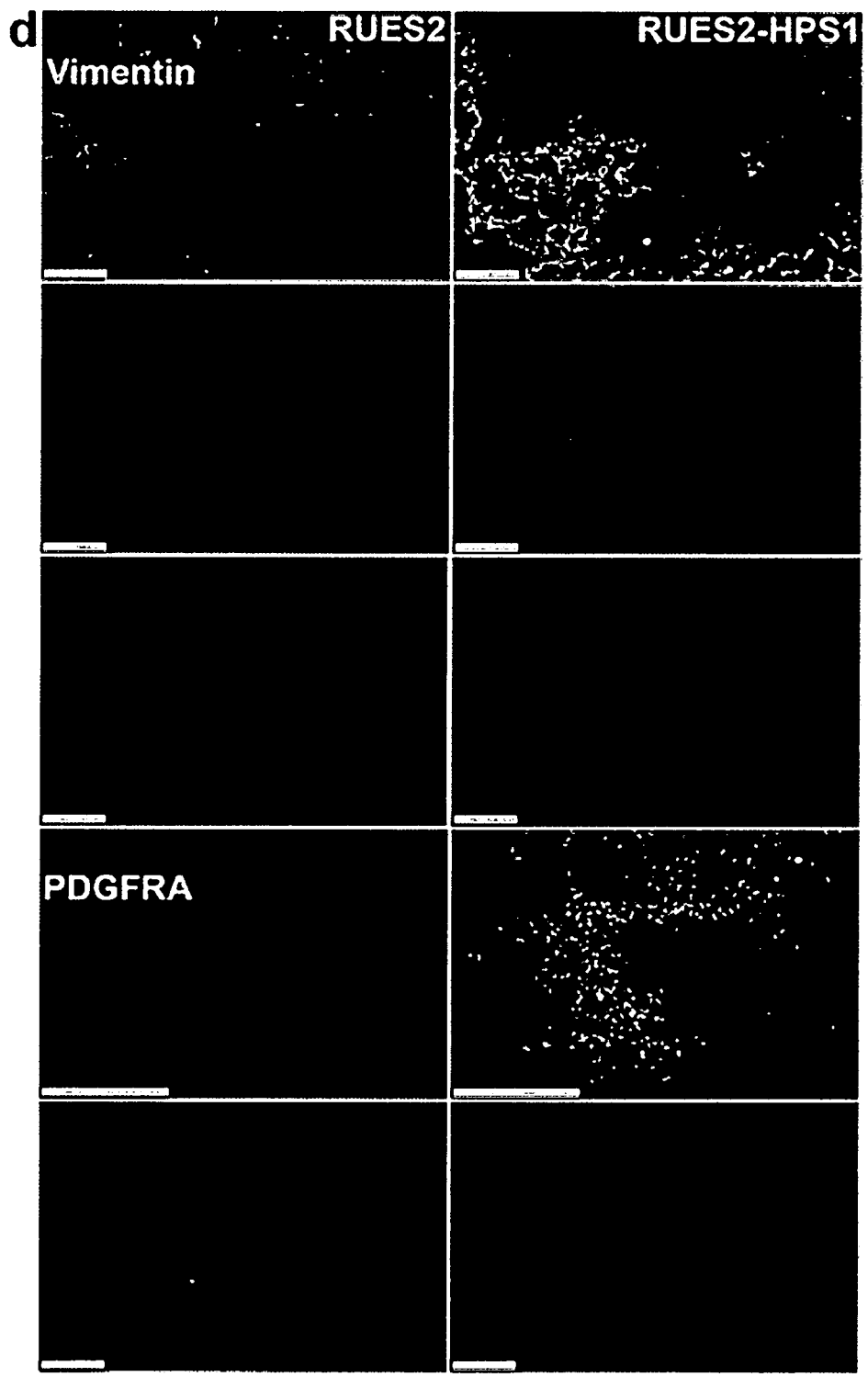
Figure 10B:
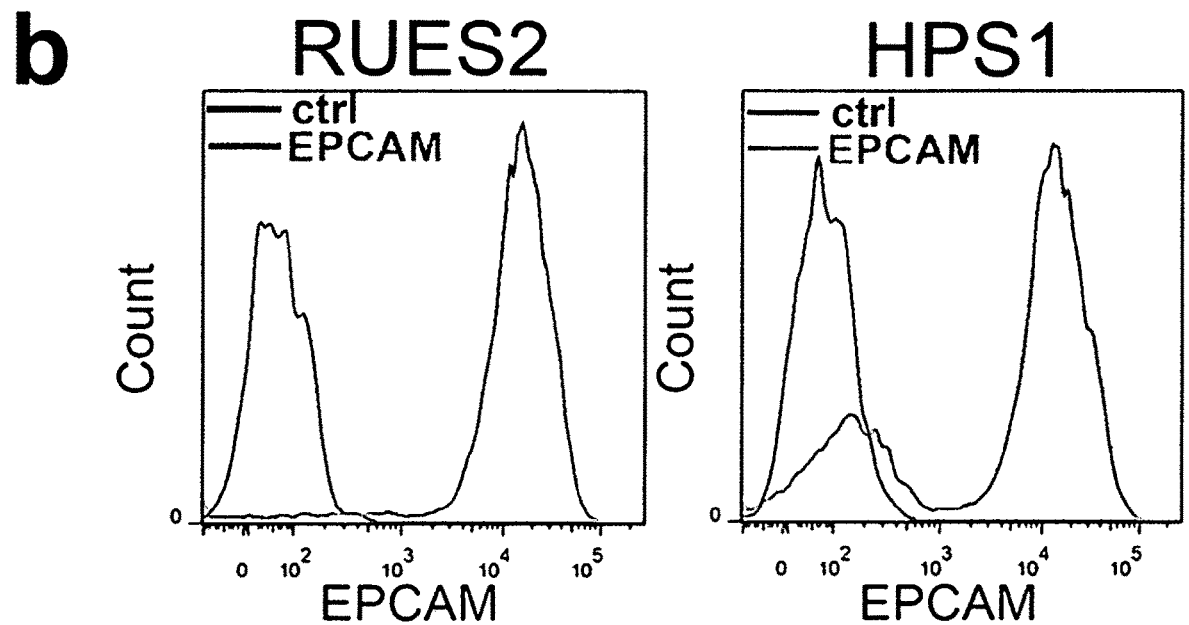
Figure 10C:
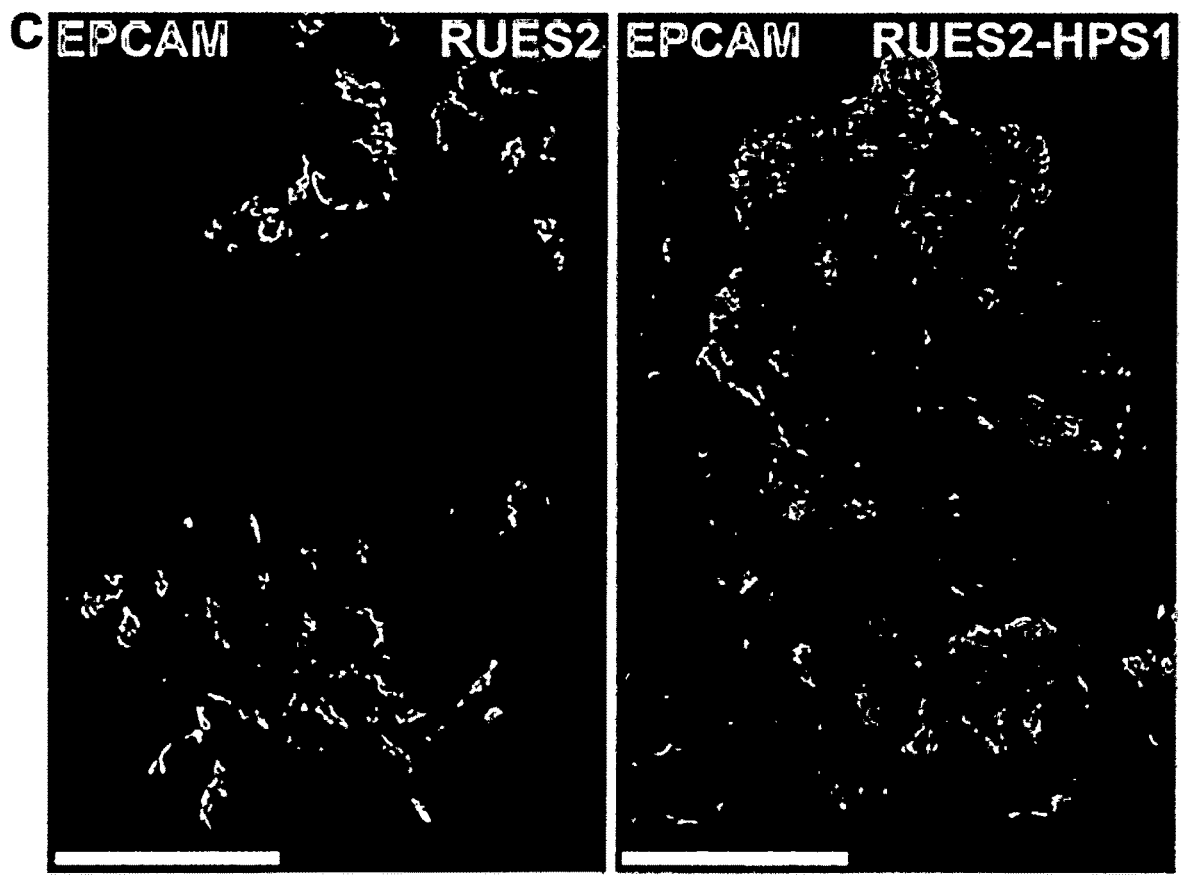
Figure 10D:
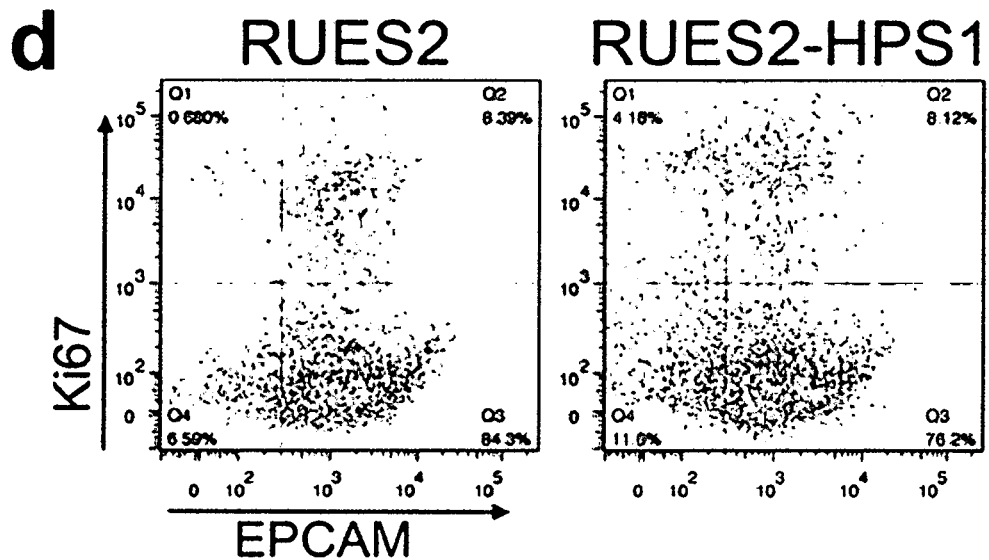
Figure 10E:
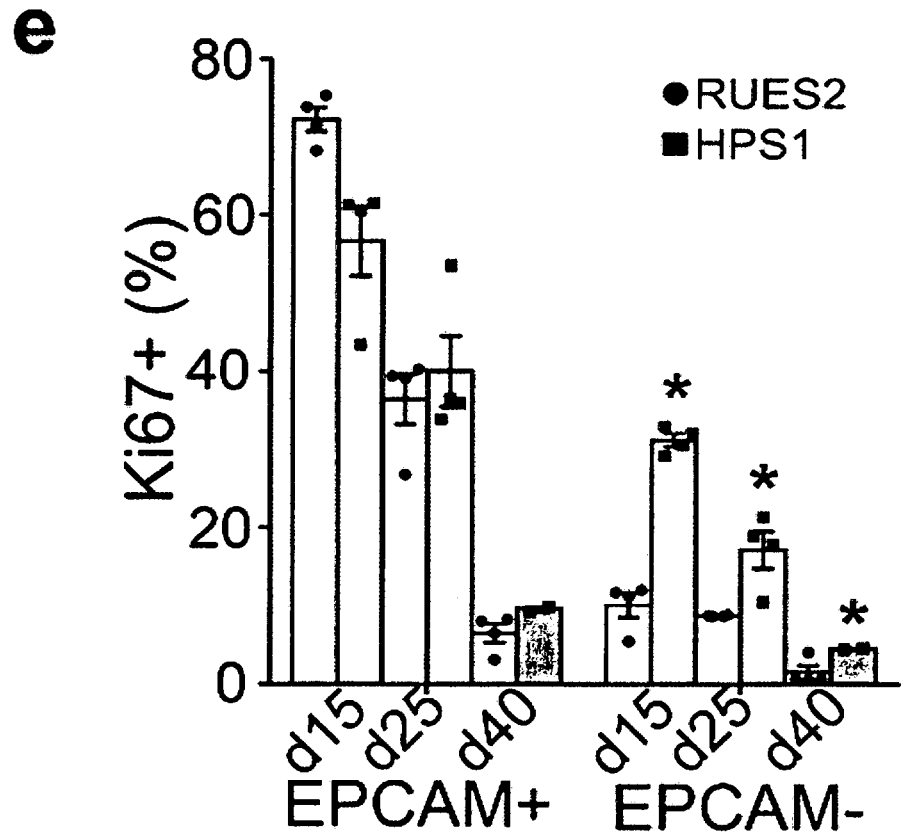
Figure 10F:
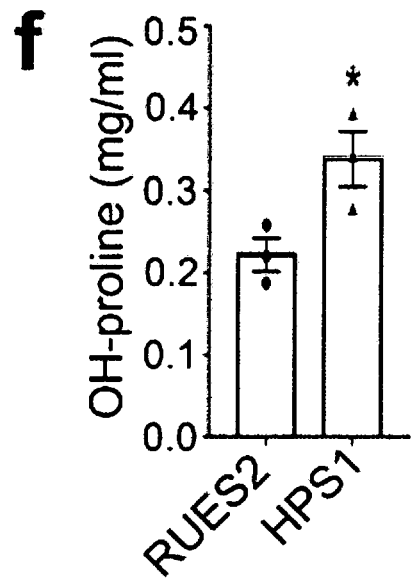
Figure 10G:
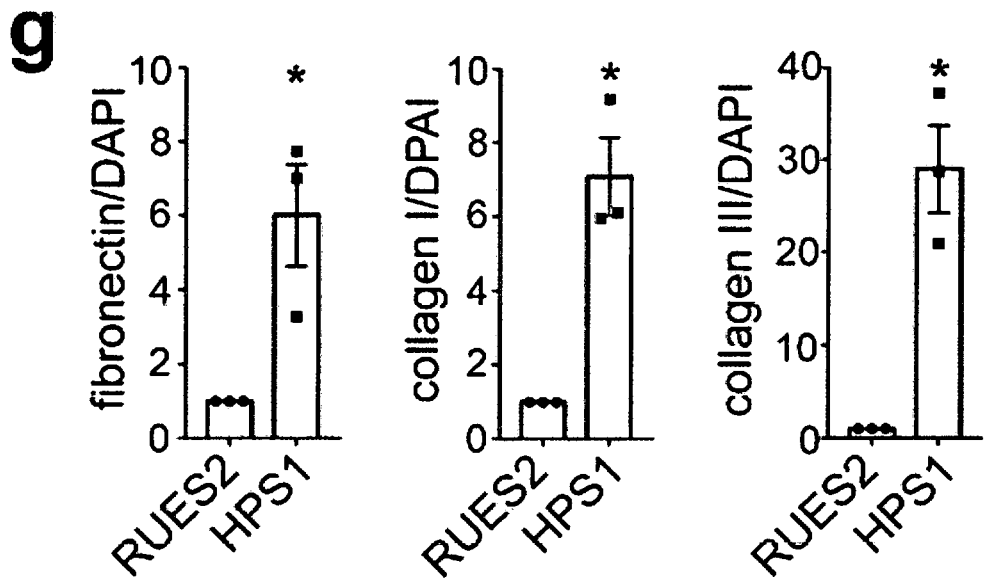
Figure 10H:
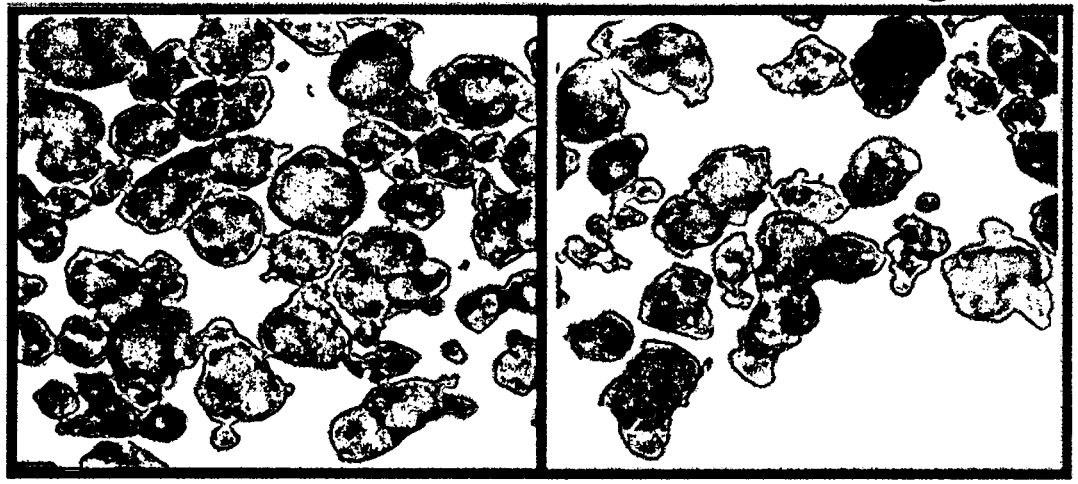
Figure 10I:
FIG. 10I is an photograph showing mutant epithelial cells and FIG. 10J is a graph showing that the HSP1 cells had a higher percentage of EPCAM– cells.
Figure 10J:
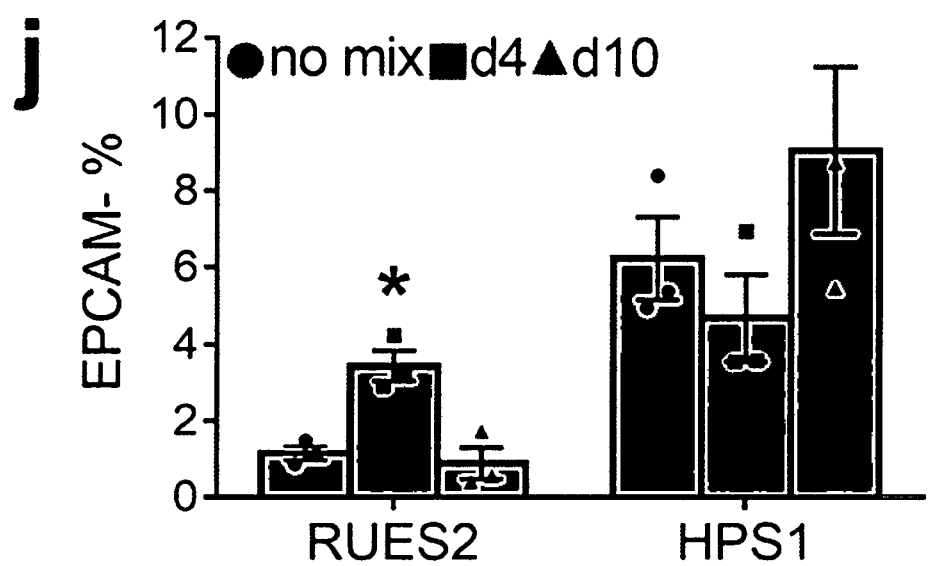

MATRIGEL® colonies derived from LBO-3D generation from RUES2 cells with CRISPR-CAS9-induced deletion of HPS1 (hereafter RUES2-HPS1$^{DEL}$) (FIG. 10A) exhibited less sharply defined branching structures in MATRIGEL® cultures than the LBOs from parental RUES2 line (FIG. 5B), with an increased fraction of EPCAM$^-$ mesenchymal cells (FIG. 5C, FIG. 10B), heterogeneously expressing the mesenchymal markers PDGFRA, PDGFRB, SMA, VIMENTIN and CD90 (FIG. 5D, low magnification tile scans in FIG. 10C). The EPCAM$^-$, but not the EPCAM$^+$ population, showed strongly enhanced proliferation in cultures of RUES2-HPS1$^{DEL}$ cells compared to parental cells (FIG. 10D, FIG. E), indicating that expansion of mesenchymal cells explains the increased fraction of EPCAM$^-$ cells. Surprisingly however, hyperproliferation of EPCAM$^-$ cells was already noticed in RUES2-HPS1$^{DEL}$ LBOs as early as d15 of suspension culture, even prior to detection of any ATII markers. Furthermore, increased hydroxyproline content (FIG. 10F) as well as enhanced extracellular matrix (ECM) autofluorescence (FIG. 10C) and immunofluorescent staining for collagens 1 and 3 and fibronectin (FIG. 5D, FIG. 10G) in RUES2-HPS1$^{DEL}$ cells indicated increased ECM deposition. Mixing experiments (FIG. 10H-FIG. J) were consistent with notion that the accumulation of mesenchymal cells was driven by mutant epithelial cells, and not a cell intrinsic property of mutant mesenchymal cells, a finding consistent with the notion that HPSIP[36] and potentially other forms of IPF[4] may be caused by epithelial injury. Together, these findings suggest that it is possible to model at least some fibrotic pulmonary disease using LBOs.

Information and data related to development of other cell lines harboring certain mutations (i.e., HPS2, HPS8, SFPTC and telomerase) is provided in Example 3 below. The techniques for making the each of the cell lines harboring the mutation are similar to that for the HPS1 cell line as set forth in Examples 1 and 3. The Sequences of each gene mutation are provided as well as the gRNA target sequence for insertion of each into the cell genome are provided in FIGS. 13-16. The LBOs harboring the HPS2 and telomerase demonstrate fibrotic abnormalities similar to that observed for HPS1-LBOs.

Discussion

LBOs and LBO-derived branching colonies in MATRIGEL® in vitro and growths after xenografting under the mouse kidney capsule, fulfill the definition of true organoids' and hence these colonies are properly named Lung Bud Organoids (LBOs). Previously reported "human lung organoids" were not organoids at all since they did not show branching either in vitro or after xenografting[8,9]. Furthermore, in contrast to the present LBOs, previously described lung organoids were generated in the presence of serum, but in the absence of BMP4, RA and Wnt agonism, which we have shown to be essential for lung specification in vitro[10]. Finally these structures did not develop in vivo after grafting under the kidney capsule of immunodeficient mice, but required preculture on a bioengineered scaffold to generate airway epithelial cells after subcutaneous transplantation[9]. By contrast, the morphological features of RSV infection in the distal lung, for which there is currently no model that reproduces human infection, were reproduced in LBO-3D model of RUES2 cells infected with RSV for the first time. The RUES2-HPS1$^{DEL}$ LBO-3D model also showed evidence of fibrosis (Hermansky-Pudlak syndrome associated interstitial pneumonia or HPSIP) in cells lacking HPS1, which is the mutation causing the most penetrant form of pulmonary fibrosis that is clinically, prognostically, radiologically and pathologically indistinguishable from IPF[4,5,36]. It is remarkable, however, that while the disease HPSIP typically arises in the 3$^{rd}$ to 4$^{th}$ decade of life, a fibrotic phenotype could be reproduced in vitro in the RUES2-HPS1$^{DEL}$ LBO model within 40 days of directed differentiation. Without being bound by theory, it is possible that stress of in vitro culture recapitulated the changes induced by senescence and led to the very rapid appearance of the phenotype, in particular since age and telomere dysfunction are prime risk factors for IPF[35,37]. The LBO model has limitations in that after 6 months of culture in MATRIGEL®, the organoids match the second trimester of human gestation in terms of structure, marker expression and genome-wide expression signature. These findings suggest that lung development as modeled in the LBO system keeps pace with human lung development in utero. Full, terminal maturation therefore remains a challenge in the organoid field[1]. A second limitation is that branching appears random, a finding consistent with an as yet unproven 'space-filling' model of branching morphogenesis[38]. However, it has been shown that LBO-3D branching could be directed by plating several LBOs in close proximity to each other in MATRIGEL®, in which case the organoids branch away from each other, suggesting that branching can be manipulated in vitro. A third limitation is that the exact nature and patterning of the mesenchyme present in the LBOs is unclear. In vivo xenografting revealed that LBO-xeno-associated mesodermal cells do not have the potential to generate endothelial cells, bone or skeletal muscle, suggesting that the mesenchyme is specified to some extent. The various mesenchymal lineages in the lung and their ontogeny are still poorly characterized.[6] Pulmonary vasculature is likely not derived from pulmonary mesenchyme however. Proximal pulmonary vessels are derived from a common cardiopulmonary mesenchymal progenitor, while the development origin of the alveolar capillary network likely arises from VE-cadherin$^+$ progenitors arising in preexisting trunk vessels.[6,39] A fourth limitation is that the in vitro cultures are strongly biased towards distal lung, and, although some areas co-expressing SOX2 and SOX9 expressed more proximal markers for goblet cells and club cell precursors, mature club cells, ciliated cells or basal cells were not observed. We could also not achieve induction of ATI markers in vitro, although ATI potential is present after engraftment in vivo.

Taken together, this work indicates that, despite certain limitations, LBOs (both 3D and xeno) will be a useful tool for the study of human lung development, modeling lung disease and screening drugs for their effect on normal LBO and on LBO that model lung diseases such as RSV infection and fibrosis.

Drug Screening

The present invention provides a method for screening for a test agent that, inter alia, prevents or reduces the formation of collagen in spheres of lung and airway cells, as described herein. However it is not limited to preventing or reducing collagen as fibronectin and any other extracellular matrix protein, as well as all types of mesenchymal cells (fibroblast, lipofibroblast, myofibroblasts, etc.) can also be reduced.

Another screening embodiment identifies test agents that increase or decrease surfactant production in a population of cells made by the present methods.

Examples of the agents include protein, peptide, nonpeptidic compound, synthesis compound, fermentation product, cell extract, plant extract, animal tissue extract and the like. a nucleic acid, a peptide, a protein, a nonpeptidic compound, a synthetic compound, a fermentation product, a cell extract, a cell culture supernatant, a plant extract, a mammalian tissue extract, a plasma, or the like. The test substance may be a novel substance or a known substance. The test substance may be in the form of a salt and such a salt may be a salt with a physiologically acceptable acid or base. These substances may be novel or known. In addition, compound library produced using a combinatorial chemistry technique, random peptide library produced by solid phase synthesis or phage display, and the like are also preferable examples of the test substances.

As used herein, the term "test agent" is very broad (as described below), and can refer to pharmaceutical or non-pharmaceutical compounds or substrates which are assessed for the ability to block collagen formation in spheres of lung and airway cells as described herein, or that prevent the collapse of collagen-expression spheres.

In one embodiment, BLBOs are treated with a small molecular weight test reagent that can transport through the cell membrane. The amount of such agent may be determined by one skill in the art, but may generally be between about 0.01 micromolar (0.01 μM) to 1 mM. The duration of contact of the cultured spheres or other test cells with the test compound can be varied. Determination of the ability of the compound to reduce or prevent fibrosis in BLBO may be done at any time as long as it is after the start of the administration of the test substance.

Libraries screened using the methods of the present invention can comprise a variety of types of compounds. In some embodiments, the compounds are peptide molecules. In a non-limiting example, peptide molecules can exist in a phage display library. In other embodiments, types of compounds include, but are not limited to, peptide analogs including peptides comprising non-naturally occurring amino acids, e.g., D-amino acids, phosphorous analogs of amino acids, such as Act-amino phosphoric acids, or amino acids having non-peptide linkages, nucleic acid analogs such as phosphorothioates and PNAs, hormones, antigens, synthetic or naturally occurring drugs, opiates, dopamine, serotonin, catecholamines, thrombin, acetylcholine, prostaglandins, organic molecules, pheromones, adenosine, sucrose, glucose, lactose and galactose. Libraries of polypeptides or proteins can also be used.

In an embodiment, the combinatorial libraries are small organic molecule libraries, such as, but not limited to, benzodiazepines, isoprenoids, thiazolidinones, metathiazanones, pyrrolidines, morpholino compounds, and diazepindiones. In another embodiment, the combinatorial libraries comprise peptoids; random bio-oligomers; benzodiazepines; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; or carbohydrate libraries. Combinatorial libraries are themselves commercially available (see, e.g., Advanced ChemTech Europe Ltd., Cambridgeshire, UK; ASINEX, Moscow Russia; BioFocus plc, Sittingbourne, UK; Bionet Research (A division of Key Organics Limited), Camelford, UK; ChemBridge Corporation, San Diego, Calif.; ChemDiv Inc, San Diego, Calif.; ChemRx Advanced Technologies, South San Francisco, Calif.; ComGenex Inc., Budapest, Hungary; Evotec OAI Ltd, Abingdon, UK; IF LAB Ltd., Kiev, Ukraine; Maybridge plc, Cornwall, UK; PharmaCore, Inc., North. Carolina; SIDDCO Inc, Tucson, Ariz.; TimTec Inc, Newark, Del.; Tripos Receptor Research Ltd, Bude, UK; Toslab, Ekaterinburg, Russia).

In one embodiment, the combinatorial compound library for the methods of the present invention may be synthesized.

Exemplary synthetic low molecular weight biologically active molecules contemplated for use herein include MaxiVerse™ from Molecular Diversity Libraries (MolBio), LOPAC1280 (from Sigma), MyriaScreen Diversity Collection of drug-like screening compounds (from Sigma), compound libraries available on the world-wide web from biofocus.com/offerings/compound-libraries.htm?gclid=CMXYzorejp4CFSZdagodh-ktmsw, and the like, as well as combinations of any two or more thereof.

Exemplary antibodies contemplated for use herein include any antibody (or fragment thereof) that can functionally interact with human cell types, whether said antibody is monoclonal or polyclonal. Exemplary antibodies include antibodies of the immunoglobulin subtype, Fab fragments, and the like, e.g., antibodies: which recognize cell surface markers unique to the target LBOs; that recognize any cell surface protein(s) the expression of which is induced by exposure to multi-factorial media, or that inhibit known cell signaling pathways; or which activate known cell signaling pathways, and the like, as well as combinations of any two or more thereof.

Exemplary nucleic acids contemplated for use herein include oligonucleotides, DNA molecules, RNA molecules, and the like, as well as combinations of any two or more thereof.

Exemplary DNA molecules contemplated for use herein include DNA-plasmids/vectors encoding Zinc-finger nucleases, Zinc-finger transcription factors, cDNA over-expression libraries, and the like, as well as combinations of any two or more thereof.

Exemplary RNA molecules contemplated for use herein include siRNA (see, for example, sigmaaldrich.com/life-science/functional-genomics-and-mai/sima.html on the world-wide web), shRNA (see, for example, (sigmaaldrich.com/life-science/functional-genomics-and-mai.html and openbiosystems.com/RNAi/shrnaLibraries/ as available on the world-wide web), microRNA (see, for example, mirbase.org/index.shtml as available on the world-wide web), and the like, as well as combinations of any two or more thereof. As readily recognized by those of skill in the art, RNA molecules can be spotted onto an array either directly (e.g., using siRNA or microRNA), or as a virus containing a viral expression vector containing the RNA molecule of interest (e.g., microRNA or shRNA).

The screening methods of the present invention for screening a library of test compounds preferably comprise contacting a test compound with a target LBOs, preferably under physiologic conditions.

Formation of Lung Tissue with Branching Morphogenesis

Lung bud organoids are produced according to the techniques of as described in Example 2 below. The protocol involves three stages. First, human pluripotent cells, such as induced pluripotent stem cells or embryonic stem cells, are subjected to Embryoid bodies/primitive streak formation media under conditions to induce differentiation of the pluripotent cells to definitive endoderm (DE). This first stage typically takes 4 days (d0-d4) and forms embryoid bodies having endoderm as determined through expression of CXCR4 and c-kit. Second, (d5-d6) embryoid bodies are subjected to Anteriorization media under conditions for the embryoid bodies to form anterior foregut patterning. Third, (d6-d20-25) cells are then subjected to ventralization media/branching media under conditions that induce ventralization and ultimate production of lung bud organoids (LBOs). LBO formation is determined by sonic hedgehog (SHH) expression on the tips of budding epithelial structures (See FIG. 6E).

Upon production of LBOs between d20-d25 of the culture process, organoids that have folding structures are then selected and embedded into MATRIGEL® in a sandwich configuration. Folding structures includes folding sheets of EPCAM$^+$KRT8$^+$ECAD$^+$FOXA1/2$^+$ AFE cells (FOXA2: 89.07%±3.36%, EPCAM+: 92.08%±1.88%, n=3; RUES2 ESCs) (FIG. 1C). Forming the sandwich involves adding a first amount of MATRIGEL® in a well or other suitable container and allowed to solidify to form the bottom portion of the sandwich. The selected organoids having folding structures are mixed with MATRIGEL® and placed on top of the bottom portion and allowed to solidify to form the center cell layer. Another amount of MATRIGEL® without cells is placed on top of the embedded cell layer and allowed to solidify to form the top portion of the sandwich. Ventralization media/Branching media is placed in the well and replenished periodically. Generation of branching buds from organoids occurs one week after embedding into MATRIGEL®. Extensive branching organoids is observed 2-3 weeks post embedding.

As an alternative to MATRIGEL® discussed above, other gel matrices can be implemented such as that described in Gjorevsky et al, Nature. 2016 Nov. 24; 539(7630):560-564. doi: 10.1038/nature20168 and DiMarco et al., Biomater Sci. 2015 Oct. 15; 3(10):1376-85.

EXAMPLES

Example 1: Methods

Reagents
Reagents used are listed in Table 1 below.
Human Samples
The use of human fetal tissues procured by the Human Studies Core at Columbia Center for Translational Immunology was approved by the Columbia University Medical Center (CUMC) Human research review committee and the experiments were performed in accordance with the approved protocols.
Media
hPSC maintenance media consisted of DMEM/F12 (1:1) supplemented with 20% knockout serum replacement, 0.1 mM β-mercaptoethanol, 1 ml Primocin, 5 ml Non-essential amino acids, 5 ml GlutaMax, and 20 ng/ml FGF-2. Serum-free differentiation (SFD) media consisted of IMDM/Ham's F12 (3:1) supplemented with N2, B27, 0.05% bovine serum albumin, 1% penicillin-streptomycin, 50 µg/ml ascorbic acid, 2 mM Glutamax, 0.4 µM monothioglycerol and different growth factor cocktails as indicated in Table 2.

hPSCs Maintenance
Rockefeller University Embryonic Stem Cell Line 2 (RUES2, NIH approval number NIHhESC-09-0013, Registration number 0013, passage 17-28), Sendai Virus and modified mRNA generated hiPSC lines from healthy human dermal fibroblasts[7,9] (passage 16-25) and IRF7-deficient C12 hiPSC lines[28] were maintained on mouse embryonic fibroblasts (MEFs) plated at 15,000-18,000 cells/cm$^2$. Cells were cultured in hPSC maintenance media and medium was changed daily. hPSCs were passaged with Accutase/EDTA washed and replated at a dilution of 1:48. Cultures were maintained in a humidified 5% $CO_2$ atmosphere at 37° C. Lines are karyotyped and verified for *Mycoplasma* contamination using PCR every 6 months.
Endoderm Induction
Induction of endoderm was carried as previous described[9]. Briefly, MEFs were depleted by passaging onto MATRIGEL® for 24 h supplied with hPSC maintenance media and maintained in a humidified 5% $CO_2$ atmosphere at 37° C. After MEF depletion, primitive streak and embryoid body induction was performed in embryoid bodies/primitive streak formation media (Table 2) in low attachment plates for 12-16 h followed by switching to endoderm induction media (Table 2) for 36-40 h. Embryoid bodies were fed every day and maintained in a humidified 5% $CO_2$/5% $O_2$ atmosphere at 37° C. Endoderm yield was determined by the expression of CXCR4 and c-KIT. For iPS lines, endodermal cells were purified using human CD184 (CXCR4) MicroBead kit. Cells used in all experiments had >90% endoderm yield.
Anterior Foregut Endoderm Induction
Anterior foregut endoderm was induced as previous described[9]. On day 4, embryoid bodies were dissociated with 0.05% Trypsin/EDTA and plated on fibronectin-coated multiple well plates with a density at 80,000-105,000 cells/cm$^2$. Cells were incubated in Anteriorization media-1 for 24 h followed by switching to Anteriorization media-2 for another 24 h.
Formation of Lung Bud Organoids
At the end of anterior foregut endoderm induction, cells were treated with Ventralization media (Branching media) for 48 h and three-dimensional clump formation was observed. The clumps were then suspended by gently pipetting around the wells. The suspended clumps are called lung bud organoids (LBOs) hereafter. LBOs were maintained in non-tissue culture treated multiple-well plates submerged in Branching media and were fed every other day until d20-d25.
Branching Morphogenesis in MATRIGEL®
The d20-d25 LBOs were embedded in 100% MATRIGEL® in 24-well transwell inserts and incubated in incubator until the MATRIGEL® solidified. Branching media were added to the well, after which the transwell was inserted, branching media added into the transwell insert as well. Media were changed every other day. A step-by-step protocol describing the generation of LBOs and LBO-derived branching colonies in MATRIGEL® can be found in Example 2.
Immunofluorescence Staining
LBOs and branching MATRIGEL® cultures were freshly embedded in Optimal Cutting Temperature (OCT). Samples were sectioned between 5-8 µm, and then air dried for 2 hours. The sections were fixed with 4% paraformaldehyde for 20 minutes at room temperature (RT) and washed with DPBS for 5 minutes. The sections were permeabilized with 0.3% Triton X-100/PBS for 30 minutes followed by blocking in 5% donkey serum for 1 hour. Primary antibodies (Table 3) were incubated at 4° C. overnight. The next day, sections were washed with DPBS 3×5 minutes followed by secondary antibody (Table 3) incubation for 2 hours at RT, washed 3×10 minutes with DPBS then mounted with DAPI contained fluorescent mounting medium. For 3D imaging, D25 LBOs were stained as described above, but were stained as intact organoids.

Isolation of EPCAM+ and EPCAM− Population from LBOs

LBOs were dissociated by 0.05% Trypsin/EDTA. The cells were stained with APC-conjugated EPCAM for 20 minutes at 4° C. EPCAM+ and EPCAM− cells were isolated by Fluorescence activated cell sorting (FACS) using a BD Influx Cell Sorter (San Jose, CA).

RNAseq

Total RNA from LBOs was purified using Direct-zol™ RNA MicroPrep kit. RNA concentration and RNA integrity number (RIN) were determined using an Agilent microfluidic RNA 6000 Nano Chip kit (Agilent Technologies, Santa Clara, CA) on the 2100 Bioanalyzer (Agilent Technologies, Santa Clara, CA). Those samples with RIN greater than 9 were used for RNAseq. Poly-A-pull-down was used to enrich mRNAs from total RNA samples. Libraries were prepared using Illumina TruSeq RNA prep kit (Illumina, San Diego, CA). Libraries were then sequenced using the Illumina HiSeq2000 (Illumina, San Diego, CA) at the Columbia Genome Center. Samples were multiplexed in each lane, yielding a targeted number of single-end/pair-end 100 bp reads for each sample, as a fraction of 180 million reads for the whole lane. RTA (Illumina, San Diego, CA) was used for base calling and bcl2fastq (version 1.8.4) for converting BCL to fastq format, coupled with adaptor trimming Reads were mapped to a reference genome (NCBI/build37.2) using Tophat (version 2.0.4) with 4 mismatches and 10 maximum multiple hits. To tackle the mapping of reads that are from exon-exon junctions, Tophat infers novel exon-exon junctions ab initio, and combines them with junctions from known mRNA sequences as the reference annotation. We estimated the relative abundance of genes and splice isoforms using cufflinks (version 2.0.2) with default settings. We tested for differentially expressed genes under various conditions using DEseq, an R package based on a negative binomial distribution that models the number reads from RNAseq experiments and tests for differential expression.

In Situ Hybridization

In situ hybridization was performed on frozen sections (5-8 um) using digoxigenin (DIG)-UTP-labeled SHH riboprobes. Briefly, human adult lung tissue cDNA was used as template to generate SHH PCR products containing either T7 or T3 promoter sequences (Forward: AATTAACCCT-CACTAAAGGGACAGCTCGGAAGTCATCAGTT (SEQ ID NO: 1); Reverse: TAATACGACTCACTATAGGGG CCTCTGAGTGGTGGCCATCTT (SEQ ID NO: 2)). The PCR products were used as templates to generate SHH riboprobes using T7 MAXlscript kit (Ambion) followed by RNeasy micro kit (Qiagen) to clean up the riboprobes. Different stages of the LBOs freshly embedded in OCT. Samples were sectioned between 5-8 μm followed by fixation with 4% paraformaldehyde for 20 minutes RT. The sections were washed with DEPC-DPBS for 3×5 minutes and acetylated in acetylation buffer (584 μl of triethanolamine/50 ml of DEPC-H2O/125 μl acetic anhydride) for 10 minutes. Permeabilization was carried in 0.1% Triton X-100/PBS for 30 minutes at RT followed by washed with DEPC-DPBS 3×5 minutes. The sections were incubated with hybridization buffer (5% dextran sulfate/4×SSC/50% formamide/1×Denhardt's/5% fish sperm DNA) for at least 2 hours at RT then overnight with 200 ng/ml of DIG-labeled SHH probe in hybridization buffer at 72° C. The next day, sections were incubated with 0.2×SSC pre-warmed to 72° C. for 2 hours followed by cool down to RT for 30 minutes. The sections were washed with fresh 0.2×SSC for 5 minutes then PBS for another 5 minutes. The sections were incubated with blocking solution (2% sheep serum/TBST) for 1 hour followed by anti-DIG-AP Ig overnight at 4° C. The sections were washed with TBST 3×10 minutes and rinsed in color reaction buffer (100 mM Tris, pH 9.5/0.1% Tween-20/100 mM NaCl/50 mM $MgCl_2$) for 10 minutes. Color was developed by incubating the section with BM-purple.

Mouse Kidney Capsule Transplantation

The NOD.Cg-Prkdc$^{scid}$.Il2rg$^{tm1Wjl}$/SzJ (NSG) mice were housed in a specific pathogen-free mouse facility. All the mice used at 10-13 weeks of age and not selected for gender. The experiment was set up to use 5-7 mice per time point. No statistical method was used to predetermine sample size. The experiments were not randomized Experiments and animal care were performed in accordance with the protocols approved by The Columbia University Institutional Animal Care And Use Committee. One million of d20-d25 LBO cells were mixed with 5 μl MATRIGEL® prior to surgery and implanted under the kidney capsule. Outgrowths were excised, embedded freshly in OCT for immunofluorescence or fixed in 4% paraformaldehyde for paraffin embedding. Histology was analyzed using hematoxylin/ eosin staining.

Dot Blots

Three microliter of fluid aspirated from the tubular structures of 5 month grafts was deposited onto a nitrocellulose blotting membrane (GE Healthcare Life Sciences). The dot-blot membrane was air-dried for 5 minutes, and blocked in 5% milk/PBS for 1 hour and then probed with the indicated primary antibodies (Table 3) overnight at 4° C. HRP-conjugated secondary antibodies was applied to the membranes followed by signal detection with ECL Western Blotting Detection Reagents and exposure to X-ray film.

Imaging

Samples were imaged using motorized Leica DMI6000 B (Leica Microsystems, Buffalo Grove, IL) or DMi8 (Leica Microsystems, Buffalo Grove, IL) inverted microscopes or 2-photon confocal laser scanning microscope Leica TCS SP8 (Leica Microsystems, Buffalo Grove, IL). Macroscopic images (FIG. 3A and FIG. 5A) were taken using iPhone 6 (Model: MG5A2LL/A, Apple, Cupertino, CA).

Uptake of SPB-BODIPY in Live LBOs and Quantification d170 LBOs were stained with CellMask™ Deep Red Plasma membrane Stain for 10 minutes and washed for 5 times followed by imaging prior loading SPB-BODIPY to obtained background fluorescence levels (0 min). The cultures then were loaded with 20 ng/ml purified human SPB-BODIPY protein (10 ng in total per culture) directly on top of the MATRIGEL®. Images were taken every 2 minutes using a 2-photon confocal laser scanning microscope (Leica TCS SP8) and the fluorescent intensities were quantified using Leica Application Suite X. The background fluorescence values were subtracted from all measurements before statistical analysis.

Quantification of Immunofluorescence

Images for each nuclear marker were quantified using ImageJ. Briefly, images were converted to 8-bit images and the threshold was adjusted to correspond with the nuclear stain, which allows for measurement of total area. The total area was analyzed by the "Analyze Particles" function of ImageJ. Percentage of positive cells were calculated by dividing the total area of positive cells over the total area of DAPI. For extracellular matrix quantification, fluorescence intensity was quantified using Leica Application Suite X.

The values were normalized to the RUES2 control for each individual experiment before statistical analysis.

Transmission Electron Microscopy

Transmission Electron Microscopy (TEM) was performed at the NYU Langone Medical Center Microscopy Core. LBOs were fixed with 2.5% glutaraldehyde in 0.1M sodium cacodylate buffer (pH7.2) for 2 hours and post-fixed with 1% osmium tetroxide for 1.5 hours at room temperature, then processed in a standard manner and embedded in EMbed 812 (Electron Microscopy Sciences, Hatfield, PA). Semi-thin sections were cut at 1 mm and stained with 1% Toluidine Blue to evaluate the quality of preservation and find the area of interest. Ultrathin sections (60 nm) were cut, mounted on copper grids and stained with uranyl acetate and lead citrate by standard methods. Stained grids were examined under Philips CM-12 electron microscope and photographed with a Gatan (4 k×2.7 k) digital camera (Gatan, Inc., Pleasanton, CA).

Respiratory Syncytial Virus Preparation and Infection

Recombinant red fluorescent protein (RFP)-expressing RSV A2 (rrRSV) was generated from the full-length RSV plasmid[1], MP224 by replacing the enhanced green fluorescent protein gene with the wild-type Discosoma RFP gene from pDsRed. For cell maintenance, HEp-2 cells (ATCC no. CCL-23) and Vero cells (ATCC no. CCL-81) were grown in monolayer culture and maintained in DMEM supplemented with 10% fetal calf serum (FCS) and 2 mM L-glutamine in a humidified atmosphere with 5% $CO_2$ at 37° C. Viral stocks were prepared in HEp-2 cells (ATCC no. CCL-23). Briefly, HEp-2 cells were grown overnight, washed with OptiMEM, and inoculated with rrRSV. After a 2.5-h adsorption period the cells were incubated for 3 days in DMEM supplemented with 1% FCS. Virus was harvested by one freeze-thaw cycle followed by a clarifying centrifugation at 3,500 r.p.m. and stored at −80° C. Viral titers were determined by plaque assay in Vero cells using a 2% methyl cellulose overlay, 5% (v/v) formaldehyde fixation, and crystal violet staining (0.015% w/v) at 5 days. For RSV infection of d170 LBOs, $10^7$ plaque-forming units (PFU) of RSV in 1 ml was directly added onto each MATRIGEL® culture in wells and incubated for 3 hrs at 37° C. The RSV inocula were then removed and the cultures were washed with SFD media 5 times for 5 minutes and maintained in branching media. The cultures were collected at indicated time points for whole mount staining using anti-RSV (all antigens) antibody (Meridian Life Science, B65890G). Images were taking using inverted microscopes or 2-photon confocal laser scanning microscope Leica TCS SP8 (Leica Microsystems, Buffalo Grove, IL).

Data Availability

The RNA sequencing data sets that support the findings of this study are available from the Sequence Read Archive (SRA). The SRA accession number for d25 LBOs sequencing is SRP073749 and SRR4295269 for d170 LBOs.

Statistics and Reproducibility

Statistical analysis was done using unpaired two-tailed Student's t-test or one-way ANOVA where appropriate using Prism 7. Results were shown mean±s.e.m., p values <0.05 were considered statistically significant. N-value refers to biologically independent replicates, unless noted otherwise. The investigators were not blinded to allocation during experiments and outcome assessment in animal studies, as no statistics were performed.

ADDITIONAL REFERENCES FOR EXAMPLE 1

1. Hallak L K, Spillmann D, Collins P L, Peeples M E. Glycosaminoglycan sulfation requirements for respiratory syncytial virus infection. J Virol 2000; 74:10508-10513.

Example 2: Detailed Protocol for Generation of Three-Dimensional Lung Bud Organoid and its Derived Branching Colonies This protocol describes the directed differentiation of human pluripotent stem cells (hPSCs) into three-dimensional lung bud organoids (LBOs) capable of branching morphogenesis. Based on the 2D protocol previously published by our group[1-3], we have designed a 3D system, in which hPSCs are sequentially differentiated into definitive endoderm (DE), to anterior foregut endoderm (AFE) and, ventral AFE in adherent 2D culture, followed by suspension culture to allow for LBO formation. When plated in MATRIGEL® at d25, the LBOs underwent extensive outward branching and eventually formed dilated tips, reminiscent of saccules formed during the saccular stage of lung development. These cultures can be used to study human lung development and branching morphogenesis.

Organoids are structures comprised of multiple cell types that are spatially organized similarly to an organ and recapitulate at least some specific organ functions[4]. Several types of organoids have been described, derived both from adult tissue and from pluripotent stem cells. This technology will likely have a major impact on the study of developmental biology, organ physiology and function, and disease modeling[5,6]. However, a true human lung organoid model has not yet been realized. The respiratory system consists of a complex branched system of progressively smaller airways that terminate in alveoli where gas exchange takes place[7,8]. Generation of human lung organoids has previously been reported[9,10]. However, the organoids described did not show branching morphogenesis or proximodistal specification, while function was not documented. The lung bud organoid (LBO) model described in the current protocol displays branching morphogenesis, proximodistal specification and evidence of early alveologenesis both in vivo and in vitro. Their development reaches a stage equivalent to the second trimester of human development. LBO-derived branching structures in MATRIGEL® contain type 2 alveolar epithelial cells (AT2) with abundant lamellar bodies and are capable of uptake and release of surfactant protein in vitro. Furthermore, secretion of mucins and surfactant proteins, as well as ciliary movement, were demonstrated after xenografting. The LBOs generated by this protocol therefore fulfill the definition of true organoids, and will be useful for studying human lung development and potentially for modeling human lung disease.

Reagents:

| | Name, | Catalog number, | Manufacturer |
|---|---|---|---|
| 1. | 0.05% Trypsin/EDTA, | 25300120, | Gibco |
| 2. | 10 cm² tissue-culture dish, | 353003, | BD Falcon |
| 3. | 15 ml tube, | 352097, | BD Falcon |
| 4. | 24-well transwell insert, | 8770, | BD Falcon |
| 5. | 50 ml tube, | 352098, | BD Falcon |
| 6. | 7.5% Bovine serum albumin, | 15260037, | Gibco |
| 7. | Accutase/EDTA, | AT104, | Innovative Cell Technologies |

-continued

| Name, | Catalog number, | Manufacturer |
|---|---|---|
| 8. Activin A, | 338-AC, | R&D System |
| 9. All-trans Retinoic acid, | 0695, | R&D System |
| 10. Ascorbic acid, | A4544, | Sigma |
| 11. B27, | 17504044, | Gibco |
| 12. β-mercaptoethanol, | M6250, | Sigma |
| 13. BMP4, | 214-BP, | R&D System |
| 14. CHIR 99021, | 4423, | R&D System |
| 15. c-KIT-PE, | 313204, | Biolegend |
| 16. CXCR4-APC, | 306510, | Biolegend |
| 17. FGF10, | 345-FG, | R&D System |
| 18. FGF2, | 233-FB, | R&D System |
| 19. FGF7, | 251-KG, | R&D System |
| 20. Fibronectin, | 1918-FN, | R&D System |
| 21. Glutamax, | 35050061, | Gibco |
| 22. Growth factor reduced matrigel, | 354230, | Corning |
| 23. Ham's F12, | 10-080-CV, | Cellgro |
| 24. Iscove's Modified Dulbecco's Medium (IMDM), | 10-016-CV, | Cellgro |
| 25. IWP2, | 3533, | R&D System |
| 26. knockout serum replacement, | 10828028, | Gibco |
| 27. low-adherin plate, | 3471, | costar |
| 28. MEM Non-Essential Amino Acids Solution, | 11140050, | Gibco |
| 29. Monothioglycerol, | M6145, | Sigma |
| 30. Mouse embryonic fibroblasts, | GSC-6201G, | GlobalStem |
| 31. N2, | 17502048, | Gibco |
| 32. Noggin, | 6057-NG, | R&D System |
| 33. Non-tissue culture-treated plate, | 351146, | BD Falcon |
| 34. Penicillin-streptomycin, | 30-002-CI, | Cellgro |
| 35. Primocin, | ant-pm-2, | InvivoGen |
| 36. SB 431542, | 1614, | R&D System |
| 37. Y-27632, | 1254, | R&D System |

| Media | Base media | Components | |
|---|---|---|---|
| Stop media | | IMDM | 500 ml |
| | | FBS | 25 ml |
| | | GultaMax | 5 ml |
| | | Penicillin-streptomycin | 5 ml |
| hPSC maintenance media | | DMEM/F12 | 400 ml |
| | | Knockout serum | 100 ml |
| | | β-mercaptoethanol | 0.1 mM |
| | | Primocin | 1 ml |
| | | FGF2 | 20 ng/ml |
| | | GlutaMax | 5 ml |
| Serum-free differentiation (SFD) media | | IMDM | 750 ml |
| | | Ham's F-12 | 250 ml |
| | | N2 | 5 ml |
| | | B27 | 10 ml |
| | | 7.5% BSA | 7.5 ml |
| | | Penicillin-streptomycin | 1% |
| | | GultaMax | 10 ml |
| | | Ascorbic acid | 50 μg/ml |
| | | Monothioglycerol | 0.4 μM |
| Embryoid bodies/primitive streak formation media | SFD | Y-27632 | 10 μM |
| | | BMP4 | 3 ng/ml |
| Endoderm induction media | SFD | Y-27632 | 10 μM |
| | | BMP4 | 0.5 ng/ml |
| | | FGF2 | 2.5 ng/ml |
| | | Activin A | 100 ng/ml |
| Anteriorization media-1 | SFD | Noggin | 100 ng/ml |
| | | SB431542 | 10 μM |
| Anteriorization media-2 | SFD | SB431542 | 10 μM |
| | | IWP2 | 1 μM |
| Ventralization media/Branching media | SFD | CHIR99021 | 3 μM |
| | | FGF10 | 10 ng/ml |
| | | FGF7 | 10 ng/ml |
| | | BMP4 | 10 ng/ml |
| | | all-trans Retinoic acid | 50 nM |

Equipment:
Normoxic incubator (95% air/5% $CO_2$)
Low oxygen incubator (5% $O_2$/5% $CO_2$)
Centrifuge
Hemocytometer
Picking hood
Procedure:
*MEF Depletion on MATRIGEL® (d-1)*
1. Thaw MATRIGEL® on ice and leave the ice bucket with the MATRIGEL® at 4° C. overnight.
2. Dilute MATRIGEL® in cold IMDM (1:30).
3. Add 6 ml of diluted MATRIGEL® solution to each 10 $cm_2$ tissue culture-treated dishes and let them sit for at least 3 hours at room temperature or overnight at 4° C.
4. To make one 6-well plate embryoid bodies (EBs), dissociate two confluent wells (from a 6-well plate) of human pluripotent stem cells (hPSCs) using 1 ml/well Accutase and incubate in a normoxic incubator for 2-3 minutes.
5. Aspirate the Accutase.
6. Neutralize the enzyme by stop media.
7. Pellet the dissociated cells by centrifugation at 1,400 r.p.m. for 4 minutes.
8. Aspirate enzyme and stop media as much as possible.
9. Re-suspend the cells with 10-12 ml hPSC maintenance media.
10. Plate the cells in a MATRIGEL®-coated dish (see step 3) after aspiration of the supernatant from the dish.
11. Incubate the cells in a normoxic incubator overnight.
Endoderm Induction (d0-d4)
1. On d0, remove the hPSC maintenance media from the MATRIGEL®-coated dish and add 3 ml trypsin. Incubate the dish for 1-1.5 minutes in a normoxic incubator.
2. Aspirate trypsin solution and stop the remaining enzyme by adding 10 ml stop media.
3. Collect the detached cells and pellet by centrifugation at 1,400 r.p.m. for 4 minutes.
4. Aspirate the enzyme and stop media.
5. Re-suspend the cells with 12 ml Embryoid bodies/primitive streak formation media and distribute to a 6-well low-attachment plate (2 ml/well).
6. Place the low-attachment plate in a low oxygen incubator to allow embryoid body (EB) formation.
7. After 12-16 hours, collect all EBs in a 15-ml tube and centrifuge at 800 r.p.m. for 1 minute.
8. Aspirate the Embryoid bodies/primitive streak formation media.
9. Gently re-suspend the EBs with 12 ml Endoderm induction media and distribute them equally back to the low-attachment plate (2 ml/well).
10. Return the plate back to a low oxygen incubator.
11. On d2, add 1 ml fresh Endoderm induction media to each well.
12. On d3, add 2 ml fresh Endoderm induction media to each well.
13. On d4.1-d4.3, check endoderm yield by flow cytometric analysis of CXCR4 and c-kit expression. If the endoderm yield is >90%, continue the differentiation.
Anteriorization (d5-d6)
1. Prepare fibronectin-coated 6-well plates by diluting fibronectin to 0.2% (vol/vol, 1:500, 4 μg/ml) in DPBS. Add 2 ml fibronectin/DPBS solution to each well and incubate the plates in a normoxic incubator for at least 30 minutes or 4° C. overnight.
2. Dissociate the EBs into single cells with trypsin (3 ml of trypsin per 6-well plate of EBs for a maximum 4-minute digestion).
3. Neutralize the enzyme by stop media.

4. Count the cells using a hemocytometer.
5. Pellet the dissociated cells by centrifugation at 1,400 r.p.m. for 4 minutes.
6. Aspirate the stop media.
7. Re-suspend the cells with Anteriorization media-1 at $7.5\times10^{\wedge5\wedge}$ cells/2 ml.
8. Add 2 ml of cell mixture to each well (6-well plate, fibronectin-coated, see step 1).
9. Incubate the plates in a normoxic incubator.
10. After 24 hours (±1 hour), replace the Anteriorization media-1 with Anteriorization media-2 (2 ml/well).
11. Return the plates back to a normoxic incubator.

Ventralization and Lung Bud Organoid (LBO) Formation (d6-d25)
1. After 24 hours (±1 hour), replace the Anteriorization media-2 with Ventralization media/Branching media (2 ml/well).
2. Return the plates back to a normoxic incubator.
3. Forty-eight hours later, aspirate all the Ventralization media/Branching media and add 2 ml fresh Ventralization media/Branching media to each well.
4. Suspend the organoids by gently pipetting up and down throughout the well with P1000 tips.
5. Transfer the suspended organoids to non-tissue culture-treated plates.
6. Return the plates back to a normoxic incubator.
7. Feed the organoids every other day by tilting the plate and allowing the organoids to sink to the bottom edge. Remove the old media while avoiding touching the organoids. Add 2 ml fresh Ventralization media/Branching media to each well.

Branching Organoid (d20-End of Experiment)
1. Between d20-d25, select the organoids with folding structures under picking hood.
2. Put the desired number of organoids per insert into each well (96-well U-bottom plate containing 100 µl of fresh Ventralization media/Branching media per well). Typically, one to four organoids are plated per insert (24-well insert).
3. Place 24-well inserts into non-tissue culture treated plates.
4. Lay 50 µl of 100% cold MATRIGEL® into the bottom of each insert.
5. Wait 5 minutes or until the MATRIGEL® has solidified.
6. Remove the Ventralization media/Branching media one well at a time.
7. Mix the organoids with 30 µl of 100% cold MATRIGEL® gently to avoid creating bubbles.
8. Immediately put the organoid-MATRIGEL® mixture in the center of an insert.
9. Wait for 5 minutes for the MATRIGEL® to solidify to secure the organoids in the center of the insert.
10. Add another 50 µl of 100% cold MATRIGEL® to the insert to create a MATRIGEL® sandwich.
11. Put the plates in a normoxic incubator for 10 minutes to make sure all MATRIGEL® has solidified.
12. Add 500 µl of Ventralization media/Branching media to the insert and another 500 µl of Ventralization media/Branching media into the wells.
13. Incubate the cultures in a normoxic incubator and replace the media every 2-3 days.

Timing:
Hands-on Time for Each Step:
MEF depletion on MATRIGEL® (d-1): 20 minutes
Endoderm induction (d0-d4): 2 hours
Anteriorization (d5-d6): 1 hour
Ventralization and Lung Bud Organoid (LBO) formation: 30 minutes plus suspension of organoids: 5 minutes/plate
Branching organoid: Roughly 2 hours to finish embedding 24 inserts and supplying them with media.

Expected Results:
Using this differentiation protocol, adherent clumps that will become organoids will form 2 days after switching to the Ventralization media/Branching media (d8 of the protocol). Folding structures within suspended organoids arise as early as d10-d12. Generation of branching buds from organoids occurs one week after embedding into MATRIGEL®. Extensive branching organoids is observed 2-3 weeks post embedding. Different cell lines behave differently during early organoid formation. Several iPS lines tended not to have obvious adherent clumps on d8, prior to organoid suspension. However, they formed organoids after suspension and they did branch in MATRIGEL®.

ADDITIONAL REFERENCES FOR EXAMPLE 2

1 Green, M. D. et al. Generation of anterior foregut endoderm from human embryonic and induced pluripotent stem cells. *Nat Biotechnol* 29, 267-272, doi:10.1038/nbt.1788 (2011).
2 Huang, S. X. et al. The in vitro generation of lung and airway progenitor cells from human pluripotent stem cells. *Nat Protoc* 10, 413-425, doi:10.1038/nprot.2015.023 (2015).
3 Huang, S. X. et al. Efficient generation of lung and airway epithelial cells from human pluripotent stem cells. *Nat Biotechnol* 32, 84-91, doi:10.1038/nbt.2754 (2014).
4 Lancaster, M. A. & Knoblich, J. A. Organogenesis in a dish: modeling development and disease using organoid technologies. *Science* 345, 1247125, doi:10.1126/science.1247125 (2014).
5 Fatehullah, A., Tan, S. H. & Barker, N. Organoids as an in vitro model of human development and disease. *Nat Cell Biol* 18, 246-254, doi:10.1038/ncb3312 (2016).
6 Clevers, H. Modeling Development and Disease with Organoids. *Cell* 165, 1586-1597, doi:10.1016/j.cell.2016.05.082 (2016).
7 Herriges, M. & Morrisey, E. E. Lung development: orchestrating the generation and regeneration of a complex organ. *Development* 141, 502-513, doi:10.1242/dev.098186 (2014).
8 Morrisey, E. E. & Hogan, B. L. Preparing for the first breath: genetic and cellular mechanisms in lung development. *Dev Cell* 18, 8-23, doi:10.1016/j.devcel.2009.12.010 (2010).
9 Dye, B. R. et al. A bioengineered niche promotes in vivo engraftment and maturation of pluripotent stem cell derived human lung organoids. *Elife* 5, doi:10.7554/eLife.19732 (2016).
10 Dye, B. R. et al. In vitro generation of human pluripotent stem cell derived lung organoids. *Elife* 4, doi:10.7554/eLife.05098 (2015).

Example 3: Generation and Characterization of RUES2-HPS1 Line

The RUES2-HPS1 line was generated at the Stem Cell Core Facility at Columbia University Medical Center. Briefly, RUES2 cells (passage 25) were cultured in six-well plates coated with MATRIGEL® to 70-80% confluence. Cells were electroporated with 7.5 µg of HPS1 guide RNA plasmid (pX330, Addgene Plasmid #42230) plus 2.5 µg of Cas9mCherry per well of a 6-well plate using Nucleofector 4D. Cas9mCherry-derived mCherry was used as a fluorescent marker to sort transfected cells. Twenty-four hours posttransfection, cells were sorted using FACS with a Bio-Rad S3e cell sorter and seeded at ~2,000 cells/6 cm dish on MEF feeders. Colonies were picked 7-10 days post sorting. Genomic DNAs from individual clones were isolated and genotyping was done using HPS1-specific PCR primers (HPS1-F-1 (GTAGAGGCAGCAGATCCAAGAGG (SEQ ID NO: 3)) and HPS1-R-1 (GAACAAGGTGGTC-CACACA (SEQ ID NO: 4)). 420 bp band to be expected). The PCR products were cloned into a plasmid for proper sequence using In-Fusion reaction (Clontech, Mountain View, CA). Sequencing revealed premature stop codons in each allele (FIG. 10). The above techniques were implemented to produce cell lines harboring mutations in HPS2 (FIG. 13, AP3B1, Exon 4)), HPS8 (FIG. 14, BLOC1S3 Exon2), SFPTC (FIG. 15, SFTPC Exon 2) or telomerase (FIG. 16, TERC, Exon 1) genes. In view of the teachings herein, those skilled in the art will appreciate that many other cell lines harboring a desired mutation can be produced and then grown into an LBO for further research, evaluation, and screening.

Hydroxyproline Content

Hydroxyproline content was measured followed manufacture's protocol (Sigma, MAK008-1KT). Briefly, samples from RUES2 or RUES2-HPS1 cultures were homogenized by tissue glass Teflon dounce homogenizer (10 mg samples in 100 μl of water) and transferred to a pressure-tight vial followed by adding 100 μl of concentrated hydrochloric acid (~12M) per 10 mg of sample. The mixtures were hydrolyzed at 120° C. for 3 hours. Samples were dried in a 96 well plate at 60° C. followed by Chloramine T/Oxidation Buffer Mixture for 5 mins at RT and DMAB reagent for another 90 mins at 60° C. Hydroxyproline content were measured at 560 nm. The same amount of MATRIGEL® was used as control.

Comparative Analysis Using KeyGenes

RNAseq data obtained from d170 LBOs from RUES2, C12, HDF SV and HDF mRNA lines was compared to different first and second trimesters and adult organs, including the lungs, using KeyGenes. Hierarchical clustering of 12 samples of the d170 LBOs and 75 samples from 19 organs from second trimester was performed using Cluster 3.0 and viewed by TreeView. The 87 classifier genes were calculated by KeyGenes.

TABLE 1

Reagents

| Name | Catalog Number | Vendor | Location |
| --- | --- | --- | --- |
| Agilent RNA 6000 Nano Kit | 5067-1511 | Agilent Technologies | Santa Clara, CA |
| T7 MAXIscript kit | AM1314 | Ambion | Waltham, MA |
| 20X SSC Buffer | AM9763 | Ambion | Waltham, MA |
| formamide | AB00600-00100 | American Bioanalytical | Natick, MA |
| APC BrdU Flow Kit | 552598 | BD Bioscience | San Jose, CA |
| 24-well transwell insert | 8770 | BD Falcon | Tewksbury, MA |
| CXCR4 | 306510 | Biolegend | San Diego, CA |
| c-KIT | 313204 | Biolegend | San Diego, CA |
| EPCAM-APC | 324208 | Biolegend | San Diego, CA |
| dextran sulfate | 40400040-2 | Bioworld | Dublin, OH |
| Dulbecco's Modified Eagle Medium | 10-013-CV | Cellgro | Manassas, VA |
| Ham's F12 | 10-080-CV | Cellgro | Manassas, VA |
| Iscove's Modified Dulbecco's Medium | 10-016-CV | Cellgro | Manassas, VA |
| DMEM/F12 | 10-092-CV | Cellgro | Manassas, VA |
| Penicillin-streptomycin | 30-002-CI | Cellgro | Manassas, VA |
| DPBS | 21-031-CM | Cellgro | Manassas, VA |
| Growth factor reduced matrigel | 354230 | Corning | Corning, NY |
| low-adherin plate | 3471 | costar | Tewksbury, MA |
| 16% Paraformaldehyde | 15710 | Electron Microscopy Sciences | Hatfield, PA |
| donkey serum | S30-100ML | EMD Millipore | Billerica, MA |
| Triton χ-100 | BP151 | Fisher Scientific | Hampton, NH |
| nitrocellulose blotting membrane | 10600062 | GE Healthcare Life Sciences | Pittsburgh, PA |
| knockout serum replacement | 10828028 | Gibco | Grand Island, NY |
| N2 | 17502048 | Gibco | Grand Island, NY |
| B27 | 17504044 | Gibco | Grand Island, NY |
| 7.5% Bovine serum albumin | 15260037 | Gibco | Grand Island, NY |
| Glutamax | 35050061 | Gibco | Grand Island, NY |
| 0.05% Trypsin/EDTA | 25300120 | Gibco | Grand Island, NY |
| 0.25% Trypsin/EDTA | 25200056 | Gibco | Grand Island, NY |
| Mouse embryonic fibroblasts | GSC-6201G | GlobalStem | Rockville, MD |
| Fluorescent mounting medium with DAPI | E19-18 | IHC World | Ellicott City, MD |
| Accutase/EDTA | AT104 | Innovative Cell Technologies | San Diego, CA |
| UltraPure ™ Salmon Sperm DNA Solution | 15632011 | Invitrogen | Waltham, MA |

TABLE 1-continued

| Reagents | | | |
|---|---|---|---|
| Name | Catalog Number | Vendor | Location |
| Primocin | ant-pm-2 | InvivoGen | San Diego, CA |
| CXCR4 MicroBead kit | 130-100-070 | Miltenyi Biotec | San Diego, CA |
| Sheep Serum | 092936149 | MP Biomedicals | Santa Ana, CA |
| RNeasy micro kit | 74004 | Qiagen | Valencia, CA |
| fibronectin | 1918-FN | R&D System | St. Louis, MO |
| BMP4 | 314-BP | R&D System | St. Louis, MO |
| FGF2 | 233-FB | R&D System | St. Louis, MO |
| Activin A | 338-AC | R&D System | St. Louis, MO |
| FGF10 | 345-FG | R&D System | St. Louis, MO |
| FGF7 | 251-KG | R&D System | St. Louis, MO |
| all-trans Retinoic acid | 0695 | R&D System | St. Louis, MO |
| Noggin | 6057-NG | R&D System | St. Louis, MO |
| SB 431542 | 1614 | R&D System | St. Louis, MO |
| IWP2 | 3533 | R&D System | St. Louis, MO |
| Digoxigenin-11-UTP | 11209256910 | Sigma | St. Louis, MO |
| triethanolamine | 90279 | Sigma | St. Louis, MO |
| Denhardt's Solution 50x | D2532 | Sigma | St. Louis, MO |
| Anti-digoxigenin AP-conjugate | 50-100-3276 | Sigma | St. Louis, MO |
| BM-purple | 50-100-3285 | Sigma | St. Louis, MO |
| b-mercaptoethanol | M6250 | Sigma-Aldrich | St. Louis, MO |
| Ascorbic acid | A4544 | Sigma-Aldrich | St. Louis, MO |
| Monothioglycerol | M6145 | Sigma-Aldrich | St. Louis, MO |
| NSG mice | 005557 | The Jacoson Laboratory | Bar Harbor, ME |
| OCT | 4583 | Tissue-Tek | Torrance, CA |
| Y-27632 | 1254 | Tocris | Bristol, BS, UK |
| CHIR 99021 | 4423 | Tocris | Bristol, BS, UK |
| Dexamethasone | 1126 | Tocris | Bristol, BS, UK |
| 8-bromo-cAMP | 1140 | Tocris | Bristol, BS, UK |
| Direct-zol RNA MicroPrep kit | R2062 | Zymo Research | Irvine, CA |
| Hydroxyproline assay kit | MAK008-1KT | Sigma-Aldrich | St. Louis, MO |
| fetal bovine serum | 10082-147 | Gibco | Grand Island, NY |
| pDsRed | 632412 | Clontech | Palo Alto, CA |
| OptiMEM | 11058-021 | Gibco | Grand Island, NY |
| methyl cellulose | HSC001 | R&D System | St. Louis, MO |
| crystal violet | HT90132 | Sigma-Aldrich | St. Louis, MO |
| L-glutamine | 25030-081 | Gibco | Grand Island, NY |
| CellMaskTM Deep Red Plasma membrane Stain | C10046 | ThermoFisher | Waltham, MA |
| MEM Non-Essential Amino Acids Solution (100X) | 11140050 | Gibco | Grand Island, NY |

TABLE 2

| Culture media | | |
|---|---|---|
| Time | Basal media: SFD | Working concentration |
| d −1 | MEF depletion | |
|  | Endoderm induction | |
| d 0 | Embryoid bodies/primitive streak formation media | |
|  | Y-27632 | 10 µM |
|  | BMP4 | 3 ng/ml |
| d 1-d 4 | Endoderm induction media | |
|  | Y-27632 | 10 µM |
|  | BMP4 | 0.5 ng/ml |
|  | FGF2 | 2.5 ng/ml |
|  | Activin A | 100 ng/ml |
| d 4 | Anteriorization media-1 | |
|  | Noggin | 100 ng/ml |
|  | SB431542 | 10 µM |
| d 5 | Anteriorization media-2 | |
|  | SB431542 | 10 µM |
|  | IWP2 | 1 µM |
| d 6- | Ventralization media/ Branching media | |
|  | CHIR99021 | 3 µM |
|  | FGF10 | 10 ng/ml |
|  | FGF7 | 10 ng/ml |
|  | BMP4 | 10 ng/ml |
|  | all-trans Retinoic acid | 50 nM |

TABLE 3

| Name | Host species | Clone number | Manufacturer | Catalog number | Dilution factor |
|---|---|---|---|---|---|
| Antibodies used for immunofluorscent staining | | | | | |
| EPCAM | mouse | 9C4 | Biolegend | 324202 | 1:500 |
| EPCAM | rabbit | D1B3 | Cell Signaling | 2626 | 1:1500 |
| EPCAM | goat | | R&D systems | AF960 | 10 µg/ml |
| Keratin 8 | mouse | A-9 | Santa Cruz | sc-374275 | 1:500 |
| NKK2.1 (TTF1) | mouse | 8G7G3/1 | Life Technologies | 180221 | 1:100 |
| NKK2.1 (TTF1) | rabbit | | Seven Hills | WRAB-1231 | 1:1000 |
| F0XA1 (HNF-3α) | mouse | Q-6 | Santa Cruz | sc-101058 | 1:50 |
| F0XA2 (HNF-3β) | goat | M-20 | Santa Cruz | sc-6554 | 1:50 |
| F0XA2 (HNF-3β) | rabbit | | Seven Hills | WRAB-1200 | 1:2000 |
| P63 | mouse | 4A4 | Santa Cruz | sc-8431 | 1:100 |
| P63α | rabbit | H-129 | Santa Cruz | sc-8344 | 1:100 |
| PDGFRa | rabbit | D13C6 | Cell Signaling | 5241 | 1:800 |
| E-cadherin | Rat | DECMA-1 | Biolegend | 147303 | 1:200 |
| SOX2 | goat | Y-17 | Santa Cruz | sc-17320 | 1:100 |
| SOX2 | rabbit | | Seven Hills | WRAB-1236 | 1:2000 |
| SOX9 | rabbit | | Millipore | AB5535 | 1:1000 |
| THY1 (CD90) | mouse | 5E10 | Biolegend | 328102 | 1:50 |
| MUC1 | armenian hamster | MH1 (CT2) | NeoMarkers | HM-1630-P | 1:100 |
| MUC2 | rabbit | H-300 | Santa Cruz | sc-15334 | 1:100 |
| MUC5AC | mouse | 45M1 | Abcam | ab79082 | 1:100 |
| MUC5B | rabbit | H-300 | Santa Cruz | sc-20119 | 1:100 |
| FOXJ1 | mouse | 2A5 | eBioscience | 14-9965-82 | 1:100 |
| SFTPB | rabbit | | Seven Hills | WRAB-48604 | 1:1000 |
| SFTPC | rabbit | | Seven Hills | WRAB-76694 | 1:1000 |
| ABCA3 | rabbit | | Seven Hills | WRAB-70565 | 1:1000 |
| HOPX | rabbit | FL-73 | Santa Cruz | sc-30216 | 1:250 |
| Caveolin 1 | rabbit | D46G3 | Cell Signaling | 3267 | 1:400 |
| PDPN | rabbit | FL-162 | Santa Cruz | sc-134482 | 1:100 |
| Vimentin | rabbit | D21H3 | Cell Signaling | 5741 | 1:100 |
| Collagen IV | mouse | COL-94 | Abcam | ab6311 | 1:500 |
| Human nuclei | mouse | 235-1 | Millipore | MAB1281 | 1:200 |
| hCD31 | mouse | WM59 | Biolegend | 303102 | 1:200 |
| mCD31 | rat | MEC 13.3 | BD Biosciences | 550274 | 1:100 |
| SMA | rabbit | E184 | Abcam | ab32575 | 1:500 |
| SCGB3A2 | goat | K-12 | Santa Cruz | sc-48320 | 1:50 |
| Ki67 | mouse | B56 | BD Biosciences | 550609 | 1:200 |
| CC10 | goat | C-20 | Santa Cruz | sc-9770 | 1:100 |
| CC10 | goat | S-20 | Santa Cruz | sc-9773 | 1:100 |
| AQP5 | goat | G-19 | Santa Cruz | sc-9890 | 1:100 |
| NGFR | mouse | ME20.4 | Millipore | 05-446 | 1:100 |
| CLIC5 | rabbit | | ThermoFisher | PA5-14533 | 1:100 |
| AKAP5 | rabbit | | ThermoFisher | PA5-38594 | 1:100 |
| SCNN1A | rabbit | | ThermoFisher | PA5-29136 | 1:100 |
| HI1-56 | mouse | | Terrace Biotech | TB-29AHT1-56 | 1:150 |
| HT2-280 | mouse | | Terrace Biotech | TB-27AHT2-280 | 1:150 |
| CGRP | mouse | CD8 | Sigma | C9487 | 1:100 |
| PGP9.5 | mouse | 31A3 | Abcam | ab20559 | 1:200 |
| Collagen I | rabbit | | Abcam | ab34710 | 1:1000 |
| Collagen III | rabbit | | Abcam | ab7778 | 1"200 |
| Vimentin-Alexa Fluor 488 | rabbit | D21H3 | Cell Signaling | 9854 | 1:800 |
| PDGFRb | rabbit | 28E1 | Cell Signaling | 3169 | 1:100 |
| Fibronectin | mouse | IST-9 | Abcam | ab6328 | 1:200 |
| K167-488 | mouse | | Biolegend | 350508 | 1:50 |

TABLE 3-continued

Antibodies and dilutions

| Name | Host species | Clone number | Manufacturer | Catalog number | Dilution factor |
|---|---|---|---|---|---|
| RSV antigen | goat | | Meridian Life Science | B65860G | 1:200 |
| CellMaskTM Deep Red Plasma membrane Stain | | | ThermoFisher | C10046 | 1:1000 |

Antibodies used for Western Blot

| | | | | | |
|---|---|---|---|---|---|
| CC10 | goat | C-20 | Santa Cruz | sc-9770 | 1:100 |
| MUC5AC | mouse | 45M1 | Abcam | ab79082 | 1:100 |
| MUC5B | rabbit | H-300 | Santa Cruz | sc-20119 | 1:100 |
| MUC2 | rabbit | H-300 | Santa Cruz | sc-15334 | 1:100 |
| SFTPB | rabbit | | Seven Hills | WRAB-48604 | 1:1000 |
| SFTPC | rabbit | | Seven Hills | WRAB-76694 | 1:1000 |
| MUC1 | armenian hamster | MH1 (CT2) | NeoMarkers | HM-1630-P | 1:100 |

REFERENCES

References in superscript are listed in Reference List 1, and references in subscript are listed in Reference List 2.

REFERENCE LIST 1

1 Lancaster, M. A. & Knoblich, J. A. Organogenesis in a dish: modeling development and disease using organoid technologies. *Science* 345, 1247125, doi:10.1126/science.1247125 (2014).
2 Collins, P. L., Fearns, R. & Graham, B. S. Respiratory syncytial virus: virology, reverse genetics, and pathogenesis of disease. *Current topics in microbiology and immunology* 372, 3-38, doi:10.1007/978-3-642-38919-1_1 (2013).
3 Johnson, J. E., Gonzales, R. A., Olson, S. J., Wright, P. F. & Graham, B. S. The histopathology of fatal untreated human respiratory syncytial virus infection. *Mod Pathol* 20, 108-119, doi:10.1038/modpathol.3800725 (2007).
4 Mulugeta, S., Nureki, S. & Beers, M. F. Lost after translation: insights from pulmonary surfactant for understanding the role of alveolar epithelial dysfunction and cellular quality control in fibrotic lung disease. *American journal of physiology. Lung cellular and molecular physiology* 309, L507-525, doi:10.1152/ajplung.00139.2015 (2015).
5 Vicary, G. W., Vergne, Y., Santiago-Cornier, A., Young, L. R. & Roman, J. Pulmonary Fibrosis in Hermansky-Pudlak Syndrome. *Ann Am Thorac Soc*, doi:10.1513/AnnalsATS.201603-186FR (2016).
6 Herriges, M. & Morrisey, E. E. Lung development: orchestrating the generation and regeneration of a complex organ. *Development* 141, 502-513, doi:10.1242/dev.098186 (2014).
7 Morrisey, E. E. & Hogan, B. L. Preparing for the first breath: genetic and cellular mechanisms in lung development. *Dev Cell* 18, 8-23, doi:S1534-5807(09)00527-9 [pii] 10.1016/j.devcel.2009.12.010 (2010).
8 Dye, B. R. et al. In vitro generation of human pluripotent stem cell derived lung organoids. *eLife* 4, doi:10.7554/eLife.05098 (2015).
9 Dye, B. R. et al. A bioengineered niche promotes in vivo engraftment and maturation of pluripotent stem cell derived human lung organoids. *eLife* 5, doi:10.7554/eLife.19732 (2016).
10 Huang, S. X. et al. Efficient generation of lung and airway epithelial cells from human pluripotent stem cells. *Nature biotechnology* 32, 84-91, doi:10.1038/nbt.2754 (2014).
11 Green, M. D. et al. Generation of anterior foregut endoderm from human embryonic and induced pluripotent stem cells. *Nature biotechnology* 29, 267-272, doi:10.1038/nbt.1788 (2011).
12 Huang, S. X. et al. The in vitro generation of lung and airway progenitor cells from human pluripotent stem cells. *Nature protocols* 10, 413-425, doi:10.1038/nprot.2015.023 (2015).
13 Kumar, M. E. et al. Mesenchymal cells. Defining a mesenchymal progenitor niche at single-cell resolution. *Science* 346, 1258810, doi:10.1126/science.1258810 (2014).
14 Hrycaj, S. M. et al. Hox5 Genes Regulate the Wnt2/2b-Bmp4-Signaling Axis during Lung Development. *Cell reports* 12, 903-912, doi:10.1016/j.celrep.2015.07.020 (2015).
15 Liu, L. et al. Hedgehog signaling in neonatal and adult lung. *American journal of respiratory cell and molecular biology* 48, 703-710, doi:10.1165/remb.2012-0347OC (2013).
16 Bellusci, S. et al. Involvement of Sonic hedgehog (Shh) in mouse embryonic lung growth and morphogenesis. *Development* 124, 53-63 (1997).
17 Pepicelli, C. V., Lewis, P. M. & McMahon, A. P. Sonic hedgehog regulates branching morphogenesis in the mammalian lung. *Current biology: CB* 8, 1083-1086 (1998).
18 Que, J. et al. Multiple dose-dependent roles for Sox2 in the patterning and differentiation of anterior foregut endoderm. *Development* 134, 2521-2531, doi:10.1242/dev.003855 (2007).
19 Alanis, D. M., Chang, D. R., Akiyama, H., Krasnow, M. A. & Chen, J. Two nested developmental waves demarcate a compartment boundary in the mouse lung. *Nature communications* 5, 3923, doi:10.1038/ncomms4923 (2014).
20 Treutlein, B. et al. Reconstructing lineage hierarchies of the distal lung epithelium using single-cell RNA-seq. *Nature* 509, 371-375, doi:10.1038/nature13173 (2014).
21 Sakurai, J. et al. Differential expression of the glycosylated forms of MUC1 during lung development. *Eur J Histochem* 51, 95-102 (2007).

22 Cutz, E., Pan, J., Yeger, H., Domnik, N. J. & Fisher, J. T. Recent advances and contraversies on the role of pulmonary neuroepithelial bodies as airway sensors. *Seminars in cell & developmental biology* 24, 40-50, doi:10.1016/j.semcdb.2012.09.003 (2013).

23 Ban, N. et al. ABCA3 as a lipid transporter in pulmonary surfactant biogenesis. *The Journal of biological chemistry* 282, 9628-9634, doi:10.1074/jbc.M611767200 (2007).

24 Ciancanelli, M. J. et al. Life-threatening influenza and impaired interferon amplification in human IRF7 deficiency. *Science*, doi:10.1126/science.aaa1578 (2015).

25 Whitsett, J. A., Wert, S. E. & Weaver, T. E. Diseases of pulmonary surfactant homeostasis. *Annual review of pathology* 10, 371-393, doi:10.1146/annurev-pathol-012513-104644 (2015).

26 Jain, R. et al. Plasticity of Hopx(+) type I alveolar cells to regenerate type II cells in the lung. *Nature communications* 6, 6727, doi:10.1038/ncomms7727 (2015).

27 Liu, Y. & Hogan, B. L. Differential gene expression in the distal tip endoderm of the embryonic mouse lung. *Gene expression patterns*: GEP 2, 229-233 (2002).

28 Rockich, B. E. et al. Sox9 plays multiple roles in the lung epithelium during branching morphogenesis. *Proc Natl Acad Sci USA* 110, E4456-4464, doi:10.1073/pnas.1311847110 (2013).

29 Perl, A. K., Kist, R., Shan, Z., Scherer, G. & Whitsett, J. A. Normal lung development and function after Sox9 inactivation in the respiratory epithelium. *Genesis* 41, 23-32, doi:10.1002/gene.20093 (2005).

30 Roost, M. S. et al. KeyGenes, a Tool to Probe Tissue Differentiation Using a Human Fetal Transcriptional Atlas. *Stem cell reports* 4, 1112-1124, doi:10.1016/j.stemcr.2015.05.002 (2015).

31 Florin, T. A., Hint, A. C. & Zorc, J. J. Viral bronchiolitis. *Lancet*, doi:10.1016/S0140-6736(16)30951-5 (2016).

32 Simoes, E. A. et al. Challenges and opportunities in developing respiratory syncytial virus therapeutics. *The Journal of infectious diseases* 211 Suppl 1, S1-S20, doi:10.1093/infdis/jiu828 (2015).

33 Liesman, R. M. et al. RSV-encoded NS2 promotes epithelial cell shedding and distal airway obstruction. *J Clin Invest* 124, 2219-2233, doi:10.1172/JCI72948 (2014).

34 Huizing, M., Helip-Wooley, A., Westbroek, W., Gunay-Aygun, M. & Gahl, W. A. Disorders of lysosome-related organelle biogenesis: clinical and molecular genetics. *Annu Rev Genomics Hum Genet* 9, 359-386, doi:10.1146/annurev.genom.9.081307.164303 (2008).

35 Ryu, J. H. et al. Idiopathic pulmonary fibrosis: evolving concepts. *Mayo Clinic proceedings* 89, 1130-1142, doi:10.1016/j.mayocp.2014.03.016 (2014).

36 Young, L. R. et al. The alveolar epithelium determines susceptibility to lung fibrosis in Hermansky-Pudlak syndrome. *Am J Respir Crit Care Med* 186, 1014-1024, doi:10.1164/rccm.201207-1206OC (2012).

37 Armanios, M. Telomerase and idiopathic pulmonary fibrosis. *Mutation research* 730, 52-58, doi:10.1016/j.mrfmmm 2011.10.013 (2012).

38 Short, K., Hodson, M. & Smyth, I. Spatial mapping and quantification of developmental branching morphogenesis. *Development* 140, 471-478, doi:10.1242/dev.088500 (2013).

39 Peng, T. et al. Coordination of heart and lung co-development by a multipotent cardiopulmonary progenitor. *Nature* 500, 589-592, doi:10.1038/nature12358 (2013).

REFERENCE LIST 2

1. Noble, P. W., Barkauskas, C. E. & Jiang, D. Pulmonary fibrosis: patterns and perpetrators. J Clin Invest 122, 2756-2762 (2012).
2. Ryu, J. H. et al. Idiopathic pulmonary fibrosis: evolving concepts. Mayo Clinic proceedings 89, 1130-1142 (2014).
3. McCurry, K. R. et al. Lung transplantation in the United States, 1998-2007. Am J Transplant 9, 942-958 (2009).
4. Lawson, W. E. et al. Endoplasmic reticulum stress enhances fibrotic remodeling in the lungs. Proc Natl Acad Sci USA 108, 10562-10567 (2011).
5. Tanjore, H., Blackwell, T. S. & Lawson, W. E. Emerging evidence for endoplasmic reticulum stress in the pathogenesis of idiopathic pulmonary fibrosis. American journal of physiology. Lung cellular and molecular physiology 302, L721-729 (2012).
6. Araya, J. et al. Insufficient autophagy in idiopathic pulmonary fibrosis. American journal of physiology. Lung cellular and molecular physiology 304, L56-69 (2013).
7. Bueno, M. et al. PINK1 deficiency impairs mitochondrial homeostasis and promotes lung fibrosis. J Clin Invest (2014).
8. Margaritopoulos, G. A. et al. Self-eating: friend or foe? The emerging role of autophagy in idiopathic pulmonary fibrosis. BioMed research international 2013, 420497 (2013).
9. Patel, A. S. et al. Autophagy in idiopathic pulmonary fibrosis. PLoS One 7, e41394 (2012).
10. Lawson, W. E. et al. Genetic mutations in surfactant protein C are a rare cause of sporadic cases of IPF. Thorax 59, 977-980 (2004).
11. Nogee, L. M. et al. A mutation in the surfactant protein C gene associated with familial interstitial lung disease. The New England journal of medicine 344, 573-579 (2001).
12. Thomas, A. Q. et al. Heterozygosity for a surfactant protein C gene mutation associated with usual interstitial pneumonitis and cellular nonspecific interstitial pneumonitis in one kindred. Am J Respir Crit Care Med 165, 1322-1328 (2002).
13. Wang, Y. et al. Genetic defects in surfactant protein A2 are associated with pulmonary fibrosis and lung cancer. American journal of human genetics 84, 52-59 (2009).
14. Armanios, M. Telomerase and idiopathic pulmonary fibrosis. Mutation research 730, 52-58 (2012).
15. Loyd, J. E. Pulmonary fibrosis in families American journal of respiratory cell and molecular biology 29, S47-50 (2003).
16. Pierson, D. M. et al. Pulmonary fibrosis in hermansky-pudlak syndrome. a case report and review. Respiration; international review of thoracic diseases 73, 382-395 (2006).
17. Mahavadi, P., Guenther, A. & Gochuico, B. R. Hermansky-Pudlak syndrome interstitial pneumonia: its the epithelium, stupid! Am J Respir Crit Care Med 186, 939-940 (2012).
18. Mahavadi, P. et al. Epithelial stress and apoptosis underlie Hermansky-Pudlak syndrome-associated interstitial pneumonia. Am J Respir Crit Care Med 182, 207-219 (2010).
19. Young, L. R. et al. The alveolar epithelium determines susceptibility to lung fibrosis in Hermansky-Pudlak syndrome. Am J Respir Crit Care Med 186, 1014-1024 (2012).
20. Young, L. R., Pasula, R., Gulleman, P. M., Deutsch, G. H. & McCormack, F. X. Susceptibility of Hermansky- 20. Pudlak mice to bleomycin-induced type II cell apoptosis and fibrosis. American journal of respiratory cell and molecular biology 37, 67-74 (2007).
21. Huizing, M., Helip-Wooley, A., Westbroek, W., Gunay-Aygun, M. & Gahl, W. A. Disorders of lysosome-related organelle biogenesis: clinical and molecular genetics. Annu Rev Genomics Hum Genet 9, 359-386 (2008).
22. Luzio, J. P., Hackmann, Y., Dieckmann, N. M. & Griffiths, G. M. The biogenesis of lysosomes and lysosome-related organelles. Cold Spring Harbor perspectives in biology 6, a016840 (2014).
23. Alder, J. K. et al. Telomere dysfunction causes alveolar stem cell failure. Proc Natl Acad Sci USA 112, 5099-5104 (2015).
24. Barkauskas, C. E. et al. Type 2 alveolar cells are stem cells in adult lung. J Clin Invest (2013).
25. Desai, T. J., Brownfield, D. G. & Krasnow, M. A. Alveolar progenitor and stem cells in lung development, renewal and cancer. Nature 507, 190-194 (2014).
26. Armanios, M. Y. et al. Telomerase mutations in families with idiopathic pulmonary fibrosis. The New England journal of medicine 356, 1317-1326 (2007).
27. Alder, J. K. et al. Short telomeres are a risk factor for idiopathic pulmonary fibrosis. Proc Natl Acad Sci USA 105, 13051-13056 (2008).
28. Alder, J. K. et al. Ancestral mutation in telomerase causes defects in repeat addition processivity and manifests as familial pulmonary fibrosis. PLoS genetics 7, e1001352 (2011).
29. Alder, J. K. et al. Exome sequencing identifies mutant TINF2 in a family with pulmonary fibrosis. Chest (2014).
30. Armanios, M. Telomerase mutations and the pulmonary fibrosis-bone marrow failure syndrome complex. The New England journal of medicine 367, 384; author reply 384 (2012).
31. Carmona-Rivera, C. et al. Clinical, molecular, and cellular features of non-Puerto Rican Hermansky-Pudlak syndrome patients of Hispanic descent. J Invest Dermatol 131, 2394-2400 (2011).
32. Wang, L. & Lyerla, T. Histochemical and cellular changes accompanying the appearance of lung fibrosis in an experimental mouse model for Hermansky Pudlak syndrome. Histochemistry and cell biology 134, 205-213 (2010).
33. Smith, L. J., Kaplan, N. B. & Brody, J. Response of normal and beige mouse alveolar type 2 cells to lung injury. The American review of respiratory disease 122, 947-957 (1980).
34. Chi, E. Y., Lagunoff, D. & Koehler, J. K. Abnormally large lamellar bodies in type II pneumocytes in Chediak-Higashi syndrome in beige mice. Laboratory investigation; a journal of technical methods and pathology 34, 166-173 (1976).
35. Clarke, R. et al. Endoplasmic reticulum stress, the unfolded protein response, autophagy, and the integrated regulation of breast cancer cell fate. Cancer research 72, 1321-1331 (2012).
36. Klionsky, D. J. et al. Guidelines for the use and interpretation of assays for monitoring autophagy. Autophagy 8, 445-544 (2012).
37. Ashrafi, G. & Schwarz, T. L. The pathways of mitophagy for quality control and clearance of mitochondria. Cell death and differentiation 20, 31-42 (2013).
38. Wolff, S., Weissman, J. S. & Dillin, A. Differential scales of protein quality control. Cell 157, 52-64 (2014).
39. Rooney, S. A. Regulation of surfactant secretion. Comparative biochemistry and physiology. Part A, Molecular & integrative physiology 129, 233-243 (2001).
40. Whitsett, J. A., Wert, S. E. & Weaver, T. E. Alveolar surfactant homeostasis and the pathogenesis of pulmonary disease. Annual review of medicine 61, 105-119 (2010).
41. Huang, S. X. et al. Efficient generation of lung and airway epithelial cells from human pluripotent stem cells. Nature biotechnology 32, 84-91 (2014).
42. Green, M. D. et al. Generation of anterior foregut endoderm from human embryonic and induced pluripotent stem cells. Nature biotechnology 29, 267-272 (2011).
43. Huang, S. X. et al. The in vitro generation of lung and airway progenitor cells from human pluripotent stem cells. Nature protocols 10, 413-425 (2015).
44. Oh, J. et al. Positional cloning of a gene for Hermansky-Pudlak syndrome, a disorder of cytoplasmic organelles. Nat Genet 14, 300-306 (1996).
45. Inoue, H., Nagata, N., Kurokawa, H. & Yamanaka, S. iPS cells: a game changer for future medicine. The EMBO journal 33, 409-417 (2014).
46. Rock, J. R. et al. Multiple stromal populations contribute to pulmonary fibrosis without evidence for epithelial to mesenchymal transition. Proc Natl Acad Sci USA 108, E1475-1483 (2011).
47. Hogan, B. L. et al. Repair and regeneration of the respiratory system: complexity, plasticity, and mechanisms of lung stem cell function. Cell Stem Cell 15, 123-138 (2014).
48. Rock, J. R. et al. Basal cells as stem cells of the mouse trachea and human airway epithelium. Proc Natl Acad Sci USA 106, 12771-12775 (2009).
49. Rawlins, E. L. & Hogan, B. L. Ciliated epithelial cell lifespan in the mouse trachea and lung. American journal of physiology. Lung cellular and molecular physiology 295, L231-234 (2008).
50. Rawlins, E. L. et al. The role of Scgb1a1+ Clara cells in the long-term maintenance and repair of lung airway, but not alveolar, epithelium. Cell Stem Cell 4, 525-534 (2009).
51. Kumar, P. A. et al. Distal airway stem cells yield alveoli in vitro and during lung regeneration following H1N1 influenza infection. Cell 147, 525-538 (2011).
52. Kim, C. F. et al. Identification of bronchioalveolar stem cells in normal lung and lung cancer. Cell 121, 823-835 (2005).
53. Zuo, W. et al. p63(+)Krt5(+) distal airway stem cells are essential for lung regeneration. Nature 517, 616-620 (2015).
54. Chapman, H. A. et al. Integrin alpha6beta4 identifies an adult distal lung epithelial population with regenerative potential in mice. J Clin Invest 121, 2855-2862 (2011).
55. Vaughan, A. E. et al. Lineage-negative progenitors mobilize to regenerate lung epithelium after major injury. Nature 517, 621-625 (2015).
56. Mulugeta, S., Nureki, S. & Beers, M. F. Lost after translation: insights from pulmonary surfactant for understanding the role of alveolar epithelial dysfunction and cellular quality control in fibrotic lung disease. American journal of physiology. Lung cellular and molecular physiology 309, L507-525 (2015).
57. Anikster, Y. et al. Mutation of a new gene causes a unique form of Hermansky-Pudlak syndrome in a genetic isolate of central Puerto Rico. Nat Genet 28, 376-380 (2001).

58. Feng, G. H., Bailin, T., Oh, J. & Spritz, R. A. Mouse pale ear (ep) is homologous to human Hermansky-Pudlak syndrome and contains a rare 'AT-AC' intron. Human molecular genetics 6, 793-797 (1997).
59. Feng, L. et al. The Hermansky-Pudlak syndrome 1 (HPS1) and HPS2 genes independently contribute to the production and function of platelet dense granules, melanosomes, and lysosomes. Blood 99, 1651-1658 (2002).
60. Li, W. et al. Hermansky-Pudlak syndrome type 7 (HPS-7) results from mutant dysbindin, a member of the biogenesis of lysosome-related organelles complex 1 (BLOC-1). Nat Genet 35, 84-89 (2003).
61. Suzuki, T. et al. Hermansky-Pudlak syndrome is caused by mutations in HPS4, the human homolog of the mouse light-ear gene. Nat Genet 30, 321-324 (2002).
62. Li, W. et al. Murine Hermansky-Pudlak syndrome genes: regulators of lysosome-related organelles. BioEssays: news and reviews in molecular, cellular and developmental biology 26, 616-628 (2004).
63. Atochina-Vasserman, E. N. et al. Early alveolar epithelial dysfunction promotes lung inflammation in a mouse model of Hermansky-Pudlak syndrome. Am J Respir Crit Care Med 184, 449-458 (2011).
64. Barbosa, M. D. et al. Identification of the homologous beige and Chediak-Higashi syndrome genes. Nature 382, 262-265 (1996).
65. Cullinane, A. R., Schaffer, A. A. & Huizing, M. The BEACH is hot: a LYST of emerging roles for BEACH-domain containing proteins in human disease. Traffic 14, 749-766 (2013).
66. Nakatani, Y. et al. Interstitial pneumonia in Hermansky-Pudlak syndrome: significance of florid foamy swelling/degeneration (giant lamellar body degeneration) of type-2 pneumocytes. Virchows Arch 437, 304-313 (2000).
67. Whitsett, J. A., Wert, S. E. & Weaver, T. E. Diseases of pulmonary surfactant homeostasis. Annual review of pathology 10, 371-393 (2015).
68. Hawkins, A. et al. A non-BRICHOS SFTPC mutant (SP-CI73T) linked to interstitial lung disease promotes a late block in macroautophagy disrupting cellular proteostasis and mitophagy. American journal of physiology. Lung cellular and molecular physiology 308, L33-47 (2015).
69. Fernandez, I. E. & Eickelberg, O. The impact of TGF-beta on lung fibrosis: from targeting to biomarkers. Proc Am Thorac Soc 9, 111-116 (2012).
70. Chilosi, M. et al. Aberrant Wnt/beta-catenin pathway activation in idiopathic pulmonary fibrosis. The American journal of pathology 162, 1495-1502 (2003).
71. Bolanos, A. L. et al. Role of Sonic Hedgehog in idiopathic pulmonary fibrosis. American journal of physiology. Lung cellular and molecular physiology 303, L978-990 (2012).
72. Crestani, B. et al. Hepatocyte growth factor and lung fibrosis. Proc Am Thorac Soc 9, 158-163 (2012).
73. Kramann, R. et al. Perivascular gli1(+) progenitors are key contributors to injury-induced organ fibrosis. Cell Stem Cell 16, 51-66 (2015).
74. Zhong, Q. et al. Role of endoplasmic reticulum stress in epithelial-mesenchymal transition of alveolar epithelial cells: effects of misfolded surfactant protein. American journal of respiratory cell and molecular biology 45, 498-509 (2011).
75. Tanjore, H. et al. Alveolar epithelial cells undergo epithelial-to-mesenchymal transition in response to endoplasmic reticulum stress. The Journal of biological chemistry 286, 30972-30980 (2011).
76. Kage, H. & Borok, Z. EMT and interstitial lung disease: a mysterious relationship. Current opinion in pulmonary medicine 18, 517-523 (2012).
77. Seibold, M. A. et al. A common MUCSB promoter polymorphism and pulmonary fibrosis. The New England journal of medicine 364, 1503-1512 (2011).
78. Peljto, A. L. et al. Association between the MUCSB promoter polymorphism and survival in patients with idiopathic pulmonary fibrosis. JAMA: the journal of the American Medical Association 309, 2232-2239 (2013).
79. Fingerlin, T. E. et al. Genome-wide association study identifies multiple susceptibility loci for pulmonary fibrosis. Nat Genet 45, 613-620 (2013).
80. Murry, C. E. & Keller, G. Differentiation of embryonic stem cells to clinically relevant populations: lessons from embryonic development. Cell 132, 661-680 (2008).
81. Hanna, J. H., Saha, K. & Jaenisch, R. Pluripotency and cellular reprogramming facts, hypotheses, unresolved issues. Cell 143, 508-525 (2010).
82. Takahashi, K. & Yamanaka, S. Induction of pluripotent stem cells from mouse embryonic and adult fibroblast cultures by defined factors. Cell 126, 663-676 (2006).
83. Yamanaka, S. A fresh look at iPS cells. Cell 137, 13-17 (2009).
84. Okita, K. & Yamanaka, S. Induced pluripotent stem cells: opportunities and challenges. Philos Trans R Soc Lond B Biol Sci 366, 2198-2207 (2011).
85. Park, I. H. et al. Reprogramming of human somatic cells to pluripotency with defined factors. Nature 451, 141-146 (2008).
86. Yu, J. et al. Induced pluripotent stem cell lines derived from human somatic cells. Science 318, 1917-1920 (2007).
87. Fox, I. J. et al. Stem cell therapy. Use of differentiated pluripotent stem cells as replacement therapy for treating disease. Science 345, 1247391 (2014).
88. Lancaster, M. A. & Knoblich, J. A. Organogenesis in a dish: modeling development and disease using organoid technologies. Science 345, 1247125 (2014).
89. Robinton, D. A. & Daley, G. Q. The promise of induced pluripotent stem cells in research and therapy. Nature 481, 295-305 (2012).
90. Mali, P., Esvelt, K. M. & Church, G. M. Cas9 as a versatile tool for engineering biology. Nature methods 10, 957-963 (2013).
91. Sternberg, S. H. & Doudna, J. A. Expanding the Biologist's Toolkit with CRISPR-Cas9. Molecular cell 58, 568-574 (2015).
92. Gonzalez, F. et al. An iCRISPR platform for rapid, multiplexable, and inducible genome editing in human pluripotent stem cells. Cell Stem Cell 15, 215-226 (2014).
93. Zhu, Z., Gonzalez, F. & Huangfu, D. The iCRISPR platform for rapid genome editing in human pluripotent stem cells. Methods in enzymology 546, 215-250 (2014).
94. Zhu, Z. & Huangfu, D. Human pluripotent stem cells: an emerging model in developmental biology. Development 140, 705-717 (2013).
95. Herriges, M. & Morrisey, E. E. Lung development: orchestrating the generation and regeneration of a complex organ. Development 141, 502-513 (2014).
96. Morrisey, E. E. & Hogan, B. L. Preparing for the first breath: genetic and cellular mechanisms in lung development. Dev Cell 18, 8-23 (2010).
97. Warburton, D. et al. Lung organogenesis. Current topics in developmental biology 90, 73-158 (2010).
98. Herring, M. J., Putney, L. F., Wyatt, G., Finkbeiner, W. E. & Hyde, D. M. Growth of alveoli during postnatal development in humans based on stereological estimation. American journal of physiology. Lung cellular and molecular physiology 307, L338-344 (2014).
99. D'Amour, K. A. et al. Efficient differentiation of human embryonic stem cells to definitive endoderm. Nature biotechnology 23, 1534-1541 (2005).
100. Kubo, A. et al. Development of definitive endoderm from embryonic stem cells in culture. Development 131, 1651-1662 (2004).
101. Wells, J. M. & Melton, D. A. Early mouse endoderm is patterned by soluble factors from adjacent germ layers. Development 127, 1563-1572 (2000).
102. Yasunaga, M. et al. Induction and monitoring of definitive and visceral endoderm differentiation of mouse ES cells. Nature biotechnology 23, 1542-1550 (2005).
103. Zorn, A. M. & Wells, J. M. Vertebrate endoderm development and organ formation. Annu Rev Cell Dev Biol 25, 221-251 (2009).
104. Nostro, M. C. & Keller, G. Generation of beta cells from human pluripotent stem cells: Potential for regenerative medicine. Seminars in cell & developmental biology (2012).
105. Nostro, M. C. et al. Stage-specific signaling through TGFbeta family members and WNT regulates patterning and pancreatic specification of human pluripotent stem cells. Development 138, 861-871 (2011).
106. Goss, A. M. et al. Wnt2/2b and beta-catenin signaling are necessary and sufficient to specify lung progenitors in the foregut. Dev Cell 17, 290-298 (2009).
107. Bellusci, S., Grindley, J., Emoto, H., Itoh, N. & Hogan, B. L. Fibroblast growth factor 10 (FGF10) and branching morphogenesis in the embryonic mouse lung. Development 124, 4867-4878 (1997).
108. Bellusci, S., Henderson, R., Winnier, G., Oikawa, T. & Hogan, B. L. Evidence from normal expression and targeted misexpression that bone morphogenetic protein (Bmp-4) plays a role in mouse embryonic lung morphogenesis. Development 122, 1693-1702 (1996).
109. Domyan, E. T. et al. Signaling through BMP receptors promotes respiratory identity in the foregut via repression of Sox2. Development 138, 971-981 (2011).
110. Li, Y., Gordon, J., Manley, N. R., Litingtung, Y. & Chiang, C. Bmp4 is required for tracheal formation: a novel mouse model for tracheal agenesis. Developmental biology 322, 145-155 (2008).
111. Chen, F. et al. A retinoic acid-dependent network in the foregut controls formation of the mouse lung primordium. J Clin Invest 120, 2040-2048 (2010).
112. Nelson, W. J. & Nusse, R. Convergence of Wnt, beta-catenin, and cadherin pathways. Science 303, 1483-1487 (2004).
113. Willert, K. & Nusse, R. Wnt proteins. Cold Spring Harbor perspectives in biology 4, a007864 (2012).
114. Gonzales, L. W., Guttentag, S. H., Wade, K. C., Postle, A. D. & Ballard, P. L. Differentiation of human pulmonary type II cells in vitro by glucocorticoid plus cAMP. American journal of physiology. Lung cellular and molecular physiology 283, L940-951 (2002).
115. Longmire, T. A. et al. Efficient derivation of purified lung and thyroid progenitors from embryonic stem cells. Cell Stem Cell 10, 398-411 (2012).
116. Kumar, M. E. et al. Mesenchymal cells. Defining a mesenchymal progenitor niche at single-cell resolution. Science 346, 1258810 (2014).
117. Hrycaj, S. M. et al. Hox5 Genes Regulate the Wnt2/2b-Bmp4-Signaling Axis during Lung Development. Cell reports 12, 903-912 (2015).
118. Liu, L. et al. Hedgehog signaling in neonatal and adult lung. American journal of respiratory cell and molecular biology 48, 703-710 (2013).
119. Yokes, S. A. et al. Genomic characterization of Gli-activator targets in sonic hedgehog-mediated neural patterning. Development 134, 1977-1989 (2007).
120. Bellusci, S. et al. Involvement of Sonic hedgehog (Shh) in mouse embryonic lung growth and morphogenesis. Development 124, 53-63 (1997).
121. Pepicelli, C. V., Lewis, P. M. & McMahon, A. P. Sonic hedgehog regulates branching morphogenesis in the mammalian lung. Current biology: CB 8, 1083-1086 (1998).
122. Que, J. et al. Multiple dose-dependent roles for Sox2 in the patterning and differentiation of anterior foregut endoderm. Development 134, 2521-2531 (2007).
123. Treutlein, B. et al. Reconstructing lineage hierarchies of the distal lung epithelium using single-cell RNA-seq. Nature 509, 371-375 (2014).
124. Sakurai, J. et al. Differential expression of the glycosylated forms of MUC1 during lung development. Eur J Histochem 51, 95-102 (2007).
125. Ban, N. et al. ABCA3 as a lipid transporter in pulmonary surfactant biogenesis. The Journal of biological chemistry 282, 9628-9634 (2007).
126. Alanis, D. M., Chang, D. R., Akiyama, H., Krasnow, M. A. & Chen, J. Two nested developmental waves demarcate a compartment boundary in the mouse lung. Nature communications 5, 3923 (2014).
127. Jain, R. et al. Plasticity of Hopx(+) type I alveolar cells to regenerate type II cells in the lung. Nature communications 6, 6727 (2015).
128. Labbadia, J. & Morimoto, R. I. The biology of proteostasis in aging and disease. Annu Rev Biochem 84, 435-464 (2015).
129. Wells, R. G. Fibrogenesis. V. TGF-beta signaling pathways. American journal of physiology. Gastrointestinal and liver physiology 279, G845-850 (2000).
130. Lindquist, J. N., Marzluff, W. F. & Stefanovic, B. Fibrogenesis. III. Posttranscriptional regulation of type I collagen. American journal of physiology. Gastrointestinal and liver physiology 279, G471-476 (2000).
131. Ishida, Y. et al. Type I collagen in Hsp47-null cells is aggregated in endoplasmic reticulum and deficient in N-propeptide processing and fibrillogenesis. Molecular biology of the cell 17, 2346-2355 (2006).
132. Hosokawa, N., Hohenadl, C., Satoh, M., Kuhn, K. & Nagata, K. HSP47, a collagen-specific molecular chaperone, delays the secretion of type III procollagen transfected in human embryonic kidney cell line 293: a possible role for HSP47 in collagen modification. Journal of biochemistry 124, 654-662 (1998).
133. Armanios, M. Syndromes of telomere shortening. Annu Rev Genomics Hum Genet 10, 45-61 (2009).
134. Park, I. H. et al. Disease-specific induced pluripotent stem cells. Cell 134, 877-886 (2008).
135. Unternaehrer, J. J. & Daley, G. Q. Induced pluripotent stem cells for modelling human diseases. Philos Trans R Soc Lond B Biol Sci 366, 2274-2285 (2011).
136. De Los Angeles, A., Loh, Y. H., Tesar, P. J. & Daley, G. Q. Accessing naive human pluripotency. Current opinion in genetics & development 22, 272-282 (2012).
137. Ferrari, F., Apostolou, E., Park, P. J. & Hochedlinger, K. Rearranging the chromatin for pluripotency. Cell Cycle 13, 167-168 (2014).
138. Kim, K. et al. Epigenetic memory in induced pluripotent stem cells. Nature 467, 285-290 (2010).

139. Hiler, D. et al. Quantification of Retinogenesis in 3D Cultures Reveals Epigenetic Memory and Higher Efficiency in iPSCs Derived from Rod Photoreceptors. Cell Stem Cell 17, 101-115 (2015).
140. Rouhani, F. et al. Genetic background drives transcriptional variation in human induced pluripotent stem cells. PLoS genetics 10, e1004432 (2014).
141. Nazarian, R. et al. An immunoblotting assay to facilitate the molecular diagnosis of Hermansky-Pudlak syndrome. Mol Genet Metab 93, 134-144 (2008).
142. Dell'Angelica, E. C., Shotelersuk, V., Aguilar, R. C., Gahl, W. A. & Bonifacino, J. S. Altered trafficking of lysosomal proteins in Hermansky-Pudlak syndrome due to mutations in the beta 3A subunit of the AP-3 adaptor. Molecular cell 3, 11-21 (1999).
143. Corral, J., Gonzalez-Conejero, R., Pujol-Moix, N., Domenech, P. & Vicente, V. Mutation analysis of HPS1, the gene mutated in Hermansky-Pudlak syndrome, in patients with isolated platelet dense-granule deficiency. Haematologica 89, 325-329 (2004).
144. Oh, J. et al. Mutation analysis of patients with Hermansky-Pudlak syndrome: a frameshift hot spot in the HPS gene and apparent locus heterogeneity. American journal of human genetics 62, 593-598 (1998).
145. Huizing, M. et al. Nonsense mutations in ADTB3A cause complete deficiency of the beta3A subunit of adaptor complex-3 and severe Hermansky-Pudlak syndrome type 2. Pediatr Res 51, 150-158 (2002).
146. Morgan, N. V. et al. A germline mutation in BLOC1S3/ reduced pigmentation causes a novel variant of Hermansky-Pudlak syndrome (HPS8). American journal of human genetics 78, 160-166 (2006).
147. Cullinane, A. R. et al. A BLOC-1 mutation screen reveals a novel BLOC1S3 mutation in Hermansky-Pudlak Syndrome type 8. Pigment Cell Melanoma Res 25, 584-591 (2012).
148. Nagle, D. L. et al. Identification and mutation analysis of the complete gene for Chediak-Higashi syndrome. Nat Genet 14, 307-311 (1996).
149. Fukai, K. et al. Homozygosity mapping of the gene for Chediak-Higashi syndrome to chromosome 1q42-q44 in a segment of conserved synteny that includes the mouse beige locus (bg). American journal of human genetics 59, 620-624 (1996).
150. Karim, M. A. et al. Apparent genotype-phenotype correlation in childhood, adolescent, and adult Chediak-Higashi syndrome. Am J Med Genet 108, 16-22 (2002).
151. Winkler, T. et al. Defective telomere elongation and hematopoiesis from telomerase-mutant aplastic anemia iPSCs. J Clin Invest 123, 1952-1963 (2013).
152. Batista, L. F. et al. Telomere shortening and loss of self-renewal in dyskeratosis congenita induced pluripotent stem cells. Nature 474, 399-402 (2011).
153. Gonzalez, R. F., Allen, L., Gonzales, L., Ballard, P. L. & Dobbs, L. G. HTII-280, a biomarker specific to the apical plasma membrane of human lung alveolar type II cells. The journal of histochemistry and cytochemistry: official journal of the Histochemistry Society 58, 891-901 (2010).
154. Chilosi, M. et al. Abnormal re-epithelialization and lung remodeling in idiopathic pulmonary fibrosis: the role of deltaN-p63. Laboratory investigation; a journal of technical methods and pathology 82, 1335-1345 (2002).
155. Luchsinger, L. L., de Almeida, M. J., Corrigan, D. J., Mumau, M. & Snoeck, H. W. Mitofusin 2 maintains haematopoietic stem cells with extensive lymphoid potential. Nature (2016).
156. Barth, S., Glick, D. & Macleod, K. F. Autophagy: assays and artifacts. The Journal of pathology 221, 117-124 (2010).
157. Zhu, J., Dagda, R. K. & Chu, C. T. Monitoring mitophagy in neuronal cell cultures. Methods Mol Biol 793, 325-339 (2011).
158. Narendra, D., Tanaka, A., Suen, D. F. & Youle, R. J. Parkin is recruited selectively to impaired mitochondria and promotes their autophagy. The Journal of cell biology 183, 795-803 (2008).
159. Pickrell, A. M. & Youle, R. J. The roles of PINK1, parkin, and mitochondrial fidelity in Parkinson's disease. Neuron 85, 257-273 (2015).
160. Youle, R. J. & van der Bliek, A. M. Mitochondrial fission, fusion, and stress. Science 337, 1062-1065 (2012).
161. Lamb, C. A., Yoshimori, T. & Tooze, S. A. The autophagosome: origins unknown, biogenesis complex. Nature reviews. Molecular cell biology 14, 759-774 (2013).
162. Santaguida, S., Vasile, E., White, E. & Amon, A. Aneuploidy-induced cellular stresses limit autophagic degradation. Genes Dev 29, 2010-2021 (2015).
163. Korfei, M. et al. Epithelial endoplasmic reticulum stress and apoptosis in sporadic idiopathic pulmonary fibrosis. Am J Respir Crit Care Med 178, 838-846 (2008).
164. Han, J. & Kaufman, R. J. Measurement of the unfolded protein response to investigate its role in adipogenesis and obesity. Methods in enzymology 538, 135-150 (2014).
165. Shang, J. Quantitative measurement of events in the mammalian unfolded protein response. Methods in enzymology 491, 293-308 (2011).
166. Carroll, T. P., Greene, C. M. & McElvaney, N. G. Measurement of the unfolded protein response (UPR) in monocytes. Methods in enzymology 489, 83-95 (2011).
167. Moeller, A., Ask, K., Warburton, D., Gauldie, J. & Kolb, M. The bleomycin animal model: a useful tool to investigate treatment options for idiopathic pulmonary fibrosis? The international journal of biochemistry & cell biology 40, 362-382 (2008).
168. Moore, B. B. & Hogaboam, C. M. Murine models of pulmonary fibrosis. American journal of physiology. Lung cellular and molecular physiology 294, L152-160 (2008).
169. Matute-Bello, G., Frevert, C. W. & Martin, T. R. Animal models of acute lung injury. American journal of physiology. Lung cellular and molecular physiology 295, L379-399 (2008).
170. Morimoto, R. I. & Cuervo, A. M. Proteostasis and the aging proteome in health and disease. The journals of gerontology. Series A, Biological sciences and medical sciences 69 Suppl 1, S33-38 (2014).
171. Raghu, G. et al. An official ATS/ERS/JRS/ALAT statement: idiopathic pulmonary fibrosis: evidence-based guidelines for diagnosis and management. Am. J. Respir. Crit. Care Med. 183, 788-824 (2011).
172. Loh, Y. H. et al. Reprogramming of T cells from human peripheral blood. Cell Stem Cell 7, 15-19 (2010).
173. Staerk, J. et al. Reprogramming of human peripheral blood cells to induced pluripotent stem cells. Cell Stem Cell 7, 20-24 (2010).
174. Brown, M. E. et al. Derivation of induced pluripotent stem cells from human peripheral blood T lymphocytes. PLoS One 5, e11373 (2010).
175. Seki, T., Yuasa, S. & Fukuda, K. Generation of induced pluripotent stem cells from a small amount of human peripheral blood using a combination of activated T cells and Sendai virus. Nature protocols 7, 718-728 (2012).

What is claimed is:

1. A method for making a branched lung bud organoid (BLBO) from mammalian pluripotent stem cells in a 3D matrix, comprising:
   a) selecting at least one lung bud organoid (LBO) with folding structures from anterior foregut endoderm cells, wherein the anterior foregut endoderm cells have been produced from the pluripotent stem cells, wherein the at least one LBO comprises lung epithelial and mesenchymal progenitors, and
   b) embedding the at least one LBO within a 3D matrix and culturing the at least one LBO in the presence of a branching medium that induces branching for a duration of time and under conditions that permit at least one branched LBO (BLBO) to form from the at least one LBO, wherein the branching medium comprises CHIR99021, FGF7, FGF10, BMP4 and retinoic acid, wherein the culturing in step b) is conducted for at least 1 week,
   wherein embedding in step b) comprises (i) solidifying a first amount of the 3D matrix in a container to form a lower portion of solidified 3D matrix, (ii) solidifying a mixture of the at least one LBO with folding structures and a second amount of the 3D matrix on top of the lower portion to form a solidified center portion; and (iii) solidifying a third amount of the 3D matrix on the solidified center portion to form a top portion,
   wherein the second amount of the 3D matrix has a concentration of about 100%, wherein the 3D matrix is a solubilized basement membrane preparation from the Engelbreth-Holm-Swarm (EHS) mouse sarcoma.

2. The method of claim 1, wherein the pluripotent stem cells are embryonic stem cells (ESCs) or induced pluripotent stem cells (iPSCs).

3. The method of claim 2, wherein the ESCs or iPSCs have been mutated to have a lung disease related mutation.

4. The method of claim 2, wherein the iPSC cells are from a subject having a lung disease gene mutation.

5. The method of claim 1, wherein the pluripotent stem cells harbor a mutation related to surfactant secretion defects.

6. The method of claim 1, wherein the pluripotent stem cells harbor an HPS1, HPS2, HPS4, LYST, hTERT, hTERC, dyskerin, CFTR, DKC1, SFTPB, SFTPC, SFTPA1, SFTPA2, MUC5B, SHH, PTCH, SMO gene mutation, or polymorphism in ABCA3, or a combination of any of the foregoing.

7. The method of claim 6, wherein the LBO or BLBO develops one or more fibrosis characteristics selected from the group consisting of increased presence of EPCAM negative mesenchymal cells, increased expression of mesenchymal cell markers, and/or enhanced extracellular matrix deposition compared to non-mutated LBO or BLBO.

8. The method of claim 1, wherein culturing in step b) is conducted for 20-270 days.

9. The method of claim 1, wherein culturing in step b) is conducted for at least 100 days.

10. The method of claim 1, wherein the culturing in step b) is conducted for at least 2 weeks.

11. The method of claim 1, wherein the culturing in step b) is conducted for at least 20 days.

12. A cell-based assay for identification of agents that treat a lung disease, comprising providing a control sample of one or more mutated BLBOs generated by the method of claim 6 and a test sample of one or more mutated BLBOs of claim 6; contacting the test sample with a test agent; determining the level of (a) expression of at least one lung and airway epithelial cell marker, (b) extracellular matrix deposition, (c) metabolism, (d) endosome trafficking, (e) cellular stress response, (f) unfolded protein response, (g) mitophagy, (h) autophagy, (i) surfactant secretion or (j) recycling, or a combination thereof, in the control and the test samples; and selecting the test agent if any determined level in the test sample is significantly different from the control sample.

13. The assay of claim 12, further comprising a second control sample of mutated BLBOs, wherein the mutated BLBOs harbor a LYST, HPS3, HPS5, and/or HPS8 mutation.

14. The assay of claim 12, wherein the one or more mutated BLBOs have one or more characteristics of fibrosis, the characteristics comprising: 1) increased presence of mesenchymal cells; 2) increased deposition of extracellular matrix; 3) increased epithelial stress; or 4) abnormal organoid morphology.

* * * * *

SEQUENCE LISTING

```
<160> NUMBER OF SEQ ID NOS: 4

<210> SEQ ID NO 1
<211> LENGTH: 41
<212> TYPE: DNA
<213> ORGANISM: Artificial Sequence
<220> FEATURE:
<223> OTHER INFORMATION: Human primer sequence (Forward)

<400> SEQUENCE: 1
aattaaccct cactaaaggg acagctcgga agtcatcagt t                 41

<210> SEQ ID NO 2
<211> LENGTH: 42
<212> TYPE: DNA
<213> ORGANISM: Artificial Sequence
<220> FEATURE:
<223> OTHER INFORMATION: Human primer sequence (Reverse)

<400> SEQUENCE: 2
taatacgact cactataggg gcctctgagt ggtggccatc tt                42

<210> SEQ ID NO 3
<211> LENGTH: 23
<212> TYPE: DNA
<213> ORGANISM: Artificial Sequence
<220> FEATURE:
<223> OTHER INFORMATION: HPS1-specific PCR primers HPS1-F-1

<400> SEQUENCE: 3
gtagaggcag cagatccaag agg                                    23

<210> SEQ ID NO 4
<211> LENGTH: 19
<212> TYPE: DNA
<213> ORGANISM: Artificial Sequence
<220> FEATURE:
<223> OTHER INFORMATION: HPS1-R-1

<400> SEQUENCE: 4
gaacaaggtg gtccacaca                                          19
```